(12) United States Patent
Shimizukawa et al.

(10) Patent No.: US 8,742,354 B2
(45) Date of Patent: Jun. 3, 2014

(54) RADIATION IMAGE CAPTURING DEVICE AND RADIATION IMAGE CAPTURING METHOD

(75) Inventors: Sho Shimizukawa, Kanagawa (JP); Kouichi Kitano, Kanagawa (JP); Yasunori Ohta, Kanagawa (JP); Naoto Iwakiri, Kanagawa (JP); Naoyuki Nishino, Kanagawa (JP); Makoto Sugizaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 208 days.

(21) Appl. No.: 13/181,532

(22) Filed: Jul. 13, 2011

(65) Prior Publication Data

US 2012/0018640 A1 Jan. 26, 2012

(30) Foreign Application Priority Data

Jul. 26, 2010 (JP) .................................. 2010-167020
Dec. 27, 2010 (JP) .................................. 2010-291106

(51) Int. Cl.
*G01J 1/42* (2006.01)
*G01T 1/00* (2006.01)
*A61B 6/00* (2006.01)

(52) U.S. Cl.
CPC ................. *A61B 6/4233* (2013.01); *A61B 6/00* (2013.01)
USPC .................................... 250/354.1; 250/363.02

(58) Field of Classification Search
CPC ............................. A61B 6/4233; A61B 6/00
USPC ............................ 250/354.1, 363.02, 370.09
See application file for complete search history.

(56) References Cited

U.S. PATENT DOCUMENTS

| 7,728,964 B2 * | 6/2010 | Feinsod et al. ................. 356/149 |
| 2002/0165687 A1 * | 11/2002 | Goto et al. ..................... 702/146 |
| 2004/0031928 A1 * | 2/2004 | Smith ............................ 250/380 |

(Continued)

FOREIGN PATENT DOCUMENTS

| JP | 2008-132216 | 6/2008 |
| JP | 2009-195612 | 9/2009 |

(Continued)

OTHER PUBLICATIONS

Partial English language translation of the following: Office action dated Feb. 28, 2014 from the Japanese Patent Office in a Japanese patent application corresponding to the instant patent application. This office action translation is submitted now in order to supplement the understanding of patent document JP 2008-132216, JP2009-195612, JP2010-167134 and JP2010-233965 which are cited in the office action and are being disclosed in the instant Information Disclosure Statement.

*Primary Examiner* — David Porta
*Assistant Examiner* — Abra Fein
(74) *Attorney, Agent, or Firm* — SOLARIS Intellectual Property Group, PLLC

(57) ABSTRACT

A radiation image capturing device includes: an image capturing unit that captures a radiation image using irradiated radiation; a radiation detection unit that detects the radiation; a determination unit that determines whether image capturing preparation is completed; and a control unit that starts detection of the radiation by the radiation detection unit, in a case in which the determination unit determines that the image capturing preparation is completed, and controls the image capturing unit to capture a radiation image, in a case in which the radiation detection unit detects the radiation.

10 Claims, 37 Drawing Sheets

(56) References Cited

U.S. PATENT DOCUMENTS

| | | |
|---|---|---|
| 2006/0208156 A1* | 9/2006 | Anderson .................. 250/208.1 |
| 2010/0061509 A1* | 3/2010 | D'Ambrosio et al. .......... 378/62 |
| 2010/0072379 A1* | 3/2010 | Nishino et al. ........... 250/363.08 |
| 2010/0084562 A1* | 4/2010 | Angell et al. ............ 250/363.01 |

FOREIGN PATENT DOCUMENTS

| | | |
|---|---|---|
| JP | 2010-081960 A | 4/2010 |
| JP | 2010-167134 | 8/2010 |
| JP | 2010-233965 | 10/2010 |
| JP | 2010-264181 A | 11/2010 |

* cited by examiner

| IMAGE CAPTURING PART | DIAGNOSIS PART | IRRADIATION TIME | TUBE VOLTAGE | TUBE CURRENT |
|---|---|---|---|---|
| CHEST | CIRCULATORY ORGAN | 200msec | 100kV | 10mA |
| CHEST | RIB | — | — | — |
| CHEST | HEART | — | — | — |
| CHEST | ... | ... | ... | ... |
| LOWER ABDOMINAL PART | LUMBAR VERTEBRA | 600msec | 100kV | 5mA |
| LOWER ABDOMINAL PART | ... | ... | ... | ... |
| ... | ... | ... | ... | ... |

RADIATION IMAGE CAPTURING DEVICE AND RADIATION IMAGE CAPTURING METHOD

CROSS-REFERENCE TO RELATED APPLICATIONS

This application claims priority under 35 USC 119 from Japanese patent application No. 2010-167020 filed on Jul. 26, 2010, and No. 2010-291106 filed on Dec. 27, 2010, the disclosure of which is incorporated by reference herein.

BACKGROUND OF THE INVENTION

1. Field of the Invention

The invention relates to a radiation image capturing device that captures an image of radiation transmitted though a human body and a radiation image capturing method.

2. Description of the Related Art

In the medical treatment field, a portable radiation image capturing device such as a flat panel detector (FPD) that detects strength of radiation transmitted through a human body and captures an image of an inner part of the human body has been used. Since the FPD (hereinafter, referred to as an electronic cassette) can capture an image in a state in which a patient is laid on a bed and adjust an image capturing location by changing the position of the electronic cassette, image capturing can be executed with flexibility with respect to a patient who cannot move.

Meanwhile, in the electronic cassette, even in a state in which radiation is not irradiated, charge is generated by a dark current and the charge is accumulated in each pixel. Since the dark current may appear as noise of a radiation image, the electronic cassette generally performs an operation of removing the charge accumulated in each pixel of the electronic cassette, immediately before a radiation image is captured. When the radiation image is captured, a control device instructs the electronic cassette and a radiation device to irradiate radiation to capture the radiation image. When capturing of the radiation image is requested, the radiation device starts radiation irradiation, and the electronic cassette starts exposure. If the radiation irradiation ends, the electric cassette reads the charge that is accumulated by the radiation irradiation. At this time, irradiation timing of the radiation by the radiation device and exposure timing of the electronic cassette are synchronized with each other. That is, synchronization of image capturing timing is carried out.

Japanese Patent Application Laid-Open (JP-A) No. 2010-081960 discloses technology in which a first measurement unit to measure time is provided in a console (control device), a second measurement unit to measure time synchronized with the first measurement unit is provided in an electronic cassette, a radiation device irradiates radiation during a predetermined period in a case in which the time becomes an exposure start time preset by the console, and the electronic cassette reads the charge generated in a radiation detector, after the predetermined period passes from the exposure start time.

The control device and the radiation device need to be electrically connected to carry out the synchronization of the image capturing timing. In order to electrically connect the control device and the radiation device to each other, a service person of a manufacture needs to perform connection work at the time of installing a system, and a service cost and a maintenance cost are needed. In a case in which a manufacture of the control device and a manufacture of the radiation device are different from each other, electric connection may not be performed in a lot of cases, in terms of safety. In contrast, in a case in which the control device and the radiation device are not electrically connected, the synchronization of the image capturing timing is not carried out. In this case, the electronic cassette is made to perform exposure for a time longer than an irradiation time of radiation, the radiation is irradiated while the electronic cassette performs the exposure, and the electronic cassette completely exposes the irradiated radiation and can capture a radiation image.

As such, in a case in which the control device and the radiation device are not electrically connected, the synchronization of the image capturing timing is not carried out. In this case, an operation of removing the unnecessary charge accumulated in each pixel of the electronic cassette may not be executed at an appropriate timing such as immediately before image capturing. At this time, a radiation image that includes a lot of noise occurring due to the dark current may be obtained.

Therefore, in order to remove a disadvantage due to the noise, the operation of removing the accumulated unnecessary charge may be repeated, regardless of the image capturing timing. Meanwhile, even in an electronic cassette in which image capturing is not scheduled in the near future (in a so-called standby state), the operation needs to be continuously executed. In particular, in a portable electronic cassette where battery capacity is restricted, if the operation is frequently executed, power is wasted, and the number of radiation images that can be obtained decreases. For this reason, convenience of the electronic cassette is lowered.

In recent years, a radiation detector such as a flat panel detector (FPD), in which a radiation-sensitive layer is disposed on a thin film transistor (TFT) active matrix substrate and radiation can be directly converted into digital data, has been put into practice. A radiation image capturing device that captures radiation images expressed by irradiated radiation using the radiation detector has also been put into practice. As methods of converting radiation in the radiation detector used in the radiation image capturing device, an indirect-conversion method that converts radiation into light in a scintillator and converts the light into charge in a semiconductor layer made of a photodiode and a direct-conversion method that converts radiation into charge in a semiconductor layer made of amorphous selenium are known. In these respective methods, there are various materials that can be used in the semiconductor layer.

Meanwhile, in the radiation detector, since a dark current causing noise exists, an image capturing time cannot be increased at random. For this reason, the radiation image capturing device that uses the radiation detector according to the related art exchanges various signals with a radiation generating device to irradiate radiation, and an irradiation operation of irradiating the radiation from the radiation generating device and an operation of capturing an image by the radiation image capturing device are synchronized with each other.

However, in a case in which the radiation irradiation operation by the radiation generating device and the image capturing operation by the radiation image capturing device need to be synchronized with each other, the radiation generating device and the radiation image capturing device need to be constructed as one integrated system. In a case in which the system is constructed by a combination with an existing radiation generating device, modification to carry out the synchronization needs to be executed at the side of the radiation generating device.

As technology that can be applied to enable capturing of a radiation image without synchronizing the radiation irradiation operation by the radiation generating device and the image capturing operation by the radiation image capturing device, Japanese Patent Application Laid-Open No. 2010-264181 describes technology for detecting a start of irradiation of radiation, on the basis of a bias current.

However, according to the technology that is described in Japanese Patent Application Laid-Open No. 2010-264181, detection of the radiation irradiation needs to be performed at all times to detect the start of irradiation of radiation and perform image capturing. In a case in which the radiation irradiation is detected at all times, power consumption increases. In particular, in a portable radiation image capturing device (hereinafter, referred to as an "electronic cassette") in which a radiation detector is incorporated and capturing of a radiation image is performed with power driven by a battery, if the power consumption increases, driving time may be shortened.

Therefore, in a case in which a radiographer instructs the radiation image capturing device to transit to an image capturing mode in which a start of irradiation of radiation is detected and a radiation image is captured, this causes more trouble for the radiographer.

SUMMARY OF THE INVENTION

The present invention has been made in view of the above circumstances and provides a radiation image capturing device and a radiation image capturing method.

According to an aspect of the invention, there is provided a radiation image capturing device which includes: an image capturing panel including a plurality of pixels that convert radiation, which is emitted from a radiation source and is transmitted through a subject, into electric signals and accumulate the electric signals, and that are arranged in a matrix; a movement amount measurement unit that measures a movement amount of the image capturing panel; and a read control unit that starts a read mode which reads the electric signals accumulated in the pixels, according to the movement amount measured by the movement amount measurement unit, ends reading of the electric signals in a case in which values of the electric signals read in the read mode become more than a threshold value which is arbitrarily set, and transits the image capturing panel to an exposure state.

BRIEF DESCRIPTION OF THE DRAWINGS

Preferred embodiments of the invention will be described in detail based on the following figures, wherein:

FIG. 11 is a diagram illustrating an example of a table of FIG. 10;

DESCRIPTION OF THE PREFERRED EMBODIMENTS

First Exemplary Embodiment

Hereinafter, exemplary embodiments of a radiation image capturing device and a radiation image capturing system having the radiation image capturing device according to the invention will be described in detail with reference to the accompanying drawings.

Figure 1:
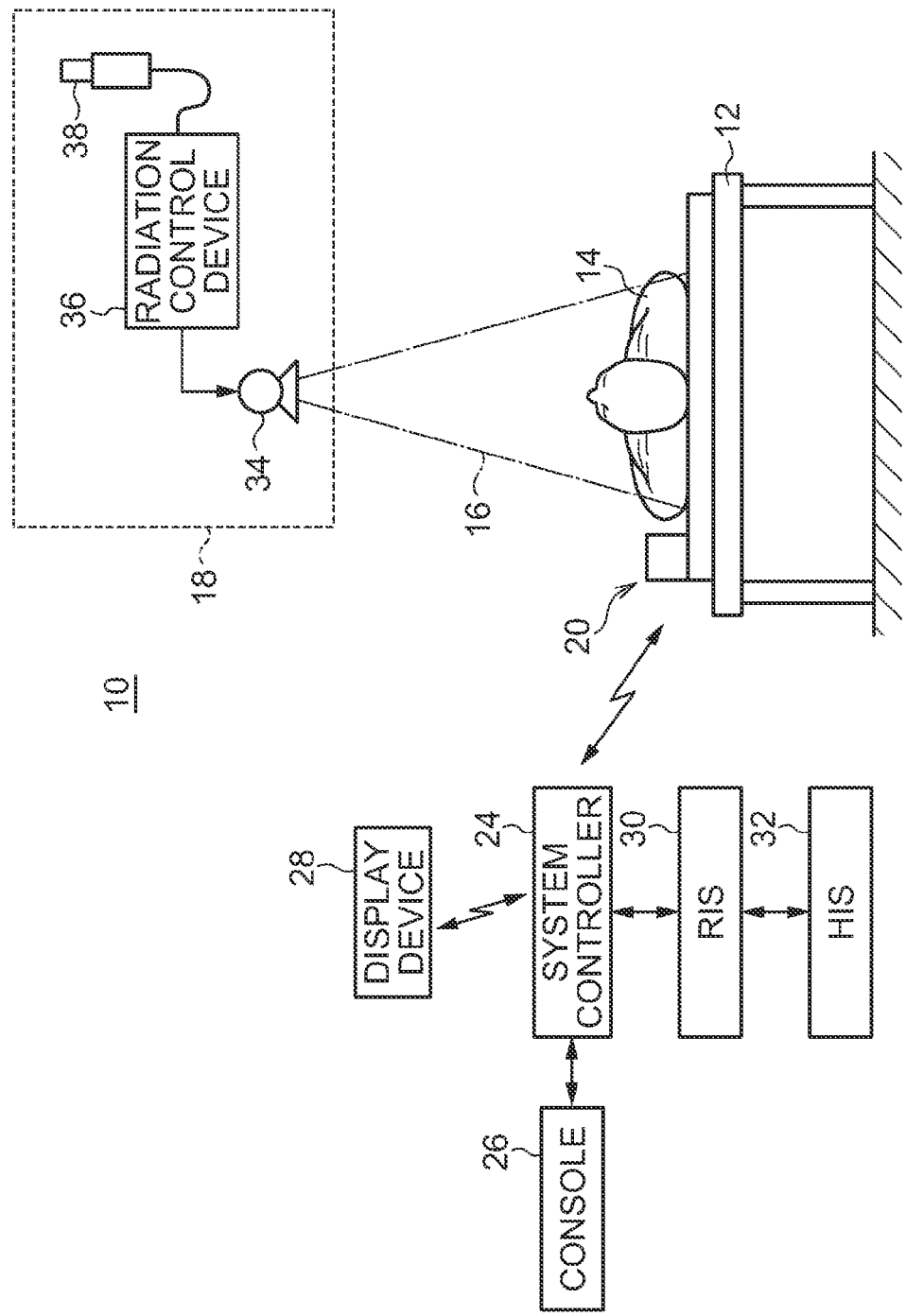
FIG. 1 is a diagram illustrating the configuration of a radiation image capturing system according to a first exemplary embodiment.

FIG. 1 is a diagram illustrating the configuration of a radiation image capturing system 10 according to the first exemplary embodiment. The radiation image capturing system 10 includes a radiation device 18 that irradiates radiation 16 onto a patient who is an subject 14 lying on an object table 12 such as a bed, an electronic cassette (radiation image capturing device) 20 that detects the radiation 16 transmitted through the subject 14 and converts the radiation into a radiation image, a system controller 24 that wholly controls the radiation image capturing system 10, a console 26 that receives an input operation from a doctor or an engineer (hereinafter, referred to as user), and a display device 28 that displays a captured radiation image.

Among the system controller 24, the electronic cassette 20, and the display device 28, signals are transmitted and received through wireless communication using a ultra-wide band (UWB), a wireless LAN such as IEEE802.11. a/b/g/n, or millimeter waves. The signals may be transmitted and received through wired communication using a cable.

To the system controller 24, a radiology information system (RIS) 30 that wholly manages radiation image or other information handled in a radiology department in a hospital is connected. To the RIS 30, a hospital information system (HIS) 32 that wholly manages hospital information in the hospital is connected.

The radiation device 18 includes a radiation source 34 that irradiates the radiation 16, a radiation control device 36 that controls the radiation source 34, and a radiation switch 38. The radiation source 34 irradiates the radiation 16 onto the electronic cassette 20. The radiation 16 that is irradiated by the radiation source 34 may be X-rays, alpha rays, beta rays, gamma rays, or electron rays. The radiation switch 38 is configured to have strokes of two steps, and the radiation control device 36 prepares for irradiation of the radiation 16, when the radiation switch 38 is semi-pushed by the user, and irradiates the radiation 16 from the radiation source 34, when the radiation switch 38 is completely pushed. The radiation control device 36 has an input device that is not illustrated in the drawings, and the user can set an irradiation time of the radiation 16, a tube voltage, and a tube current by operating the input device. The radiation control device 36 irradiates the radiation 16 from the radiation source 34, on the basis of the set irradiation time.

Figure 2:
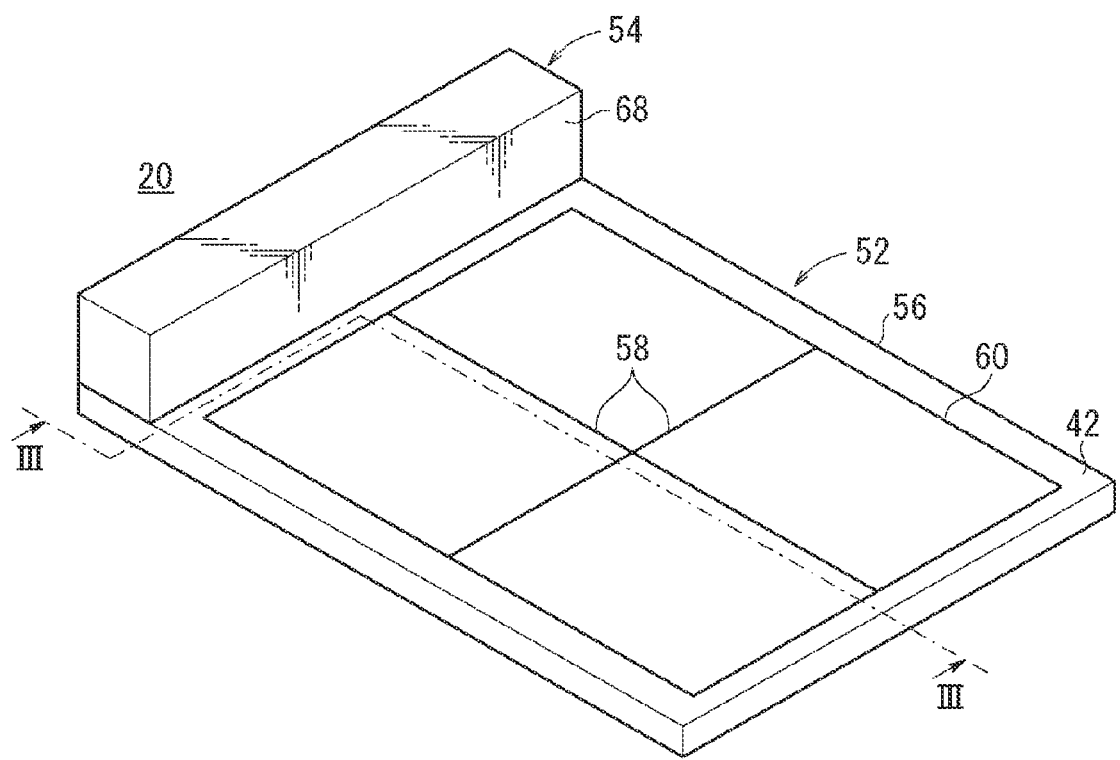
FIG. 2 is a perspective view illustrating an electronic cassette of FIG. 1.
Figure 3:
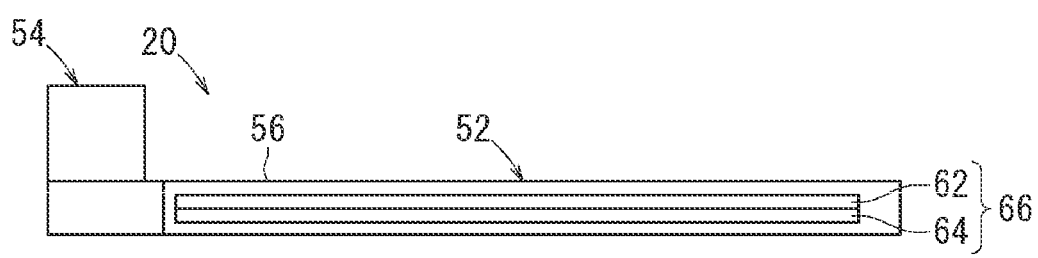
FIG. 3 is a cross-sectional view taken along the line III-III of the electronic cassette of FIG. 2.

FIG. 2 is a perspective view illustrating the electronic cassette 20 of FIG. 1 and FIG. 3 is a cross-sectional view taken along the line III-III of the electronic cassette 20 of FIG. 2. The electronic cassette 20 includes a panel unit 52 and a control unit 54 that is disposed on the panel unit 52. The thickness of the panel unit 52 is set to be smaller than the thickness of the control unit 54.

The panel unit 52 has an approximately rectangular casing 56 that is made of a material transmitting the radiation 16, and the radiation 16 is irradiated onto an image capturing surface 42 of the panel unit 52. In about a central portion of the image capturing surface 42, a guide line 58 that indicates an image capturing region and an image capturing position of the subject 14 is formed. An outer frame of the guide line 58 becomes an image capturing enabled region 60 that indicates an irradiation field of the radiation 16. The central position of the guide line 58 (intersection where the guide line 58 crosses) is the central position of the image capturing enabled region 60.

The panel unit 52 includes a radiation detector (image capturing panel) 66 that has a scintillator 62 and a radiation conversion panel 64 and a driving circuit unit 106 (refer to FIG. 6) to be descried below that drives the radiation conversion panel 64. The scintillator 62 converts the radiation 16 transmitted through the subject 14 into fluorescent light included in a visible light range. The radiation conversion panel 64 is an indirect-conversion-type radiation conversion panel that converts the fluorescent light converted by the scintillator 62 into an electric signal. The scintillator 62 and the radiation conversion panel 64 are disposed in the casing 56, sequentially from the image capturing surface 42 where the radiation 16 is irradiated. When the radiation conversion panel 64 is a direct-conversion-type radiation conversion panel to directly convert the radiation into an electric signal, the radiation conversion panel 64 becomes the radiation detector 66, because the scintillator 62 is not needed.

The control unit 54 has an approximately rectangular casing 68 that is made of a material not transmitting the radiation 16. The casing 68 extends along one end of the image capturing surface 42, and the control unit 54 is disposed outside the image capturing enabled region 60 in the image capturing surface 42. In this case, in the casing 68, a cassette control unit 122 that controls the panel unit 52 to be described below, a memory 124 that functions as a buffer memory to store image data of a captured radiation image, a communication unit 126 that can exchange a signal with the system controller 24 through wireless communication, and a power supply unit 128 such as a battery are disposed (refer to FIG. 6). The power supply unit 128 supplies power to the cassette control unit 122 and the communication unit 126.

Figure 4:
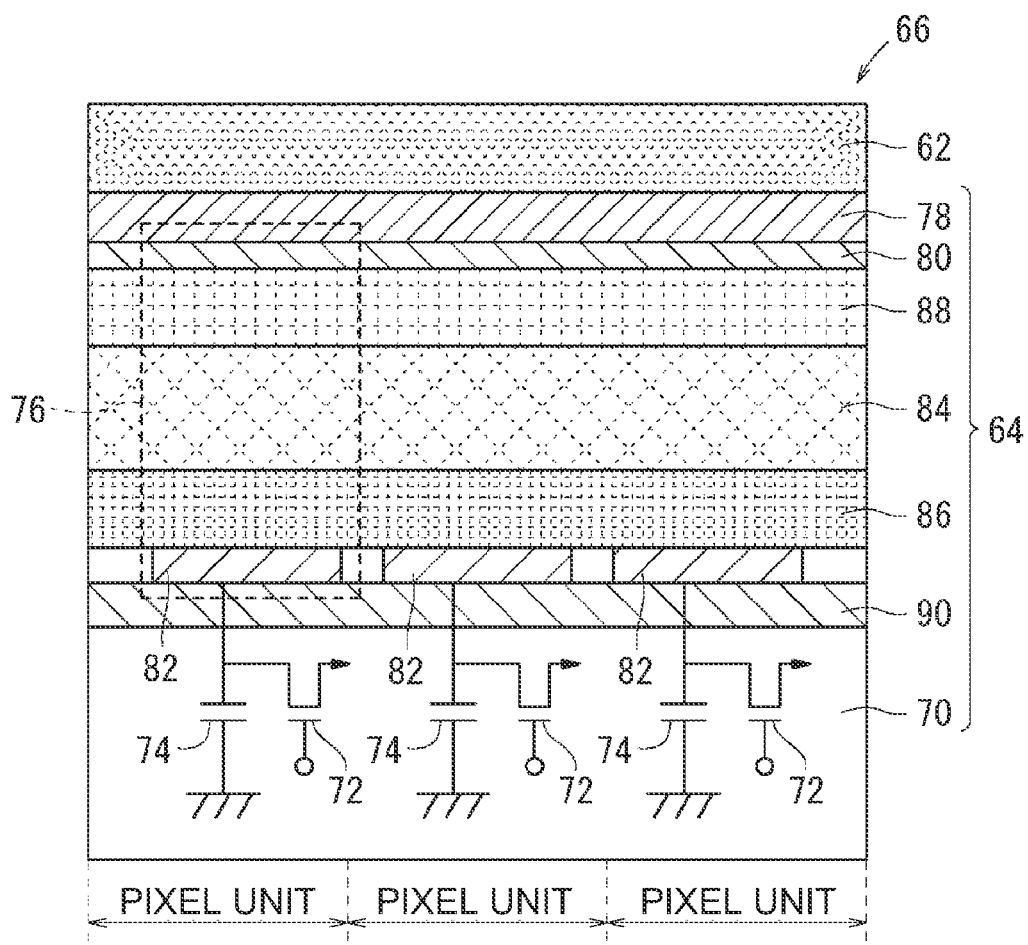
FIG. 4 is a schematic diagram illustrating the configuration of three pixels of a radiation detector of FIG. 3.

FIG. 4 is a schematic diagram illustrating the configuration of three pixels of the radiation detector 66. In the radiation detector 66, a thin film transistor (TFT) 72 which is a field effect thin film transistor, a charge accumulation unit 74, a sensor unit 76, and a scintillator 62 are sequentially laminated on a substrate 70, and each pixel is configured by the charge accumulation unit 74 and the sensor unit 76. The pixels are disposed on the substrate 70 in a matrix and each TFT (switching element) 72 outputs charge of the charge accumulation unit 74 of the pixel that is connected to each TFT. The scintillator 62 is formed on the sensor unit 76 with a transparent insulating film 78 interposed therebetween, and is configured by forming a film of a phosphor that converts the radiation 16 incident from the upper side (side opposite to the substrate 70) into light and emits the light.

It is preferable that a wavelength range of light emitted by the scintillator 62 be a visible light range (wavelength of 360 nm to 830 nm). It is more preferable that the wavelength range of light include a green wavelength range in order to capture a monochromatic image using the radiation detector 66. In a case in which an image is captured using X-rays as the radiation 16, it is preferable that the phosphor used in the scintillator 62 include gadolinium oxide sulfa (GOS) or cesium iodide (CsI). It is more preferable to use CsI(Ti) (CsI including added titanium) having an emission spectrum of 420 nm to 600 nm during the irradiation of X-rays. The emission peak wavelength of CsI(Ti) in the visible light range is 565 nm.

The sensor unit 76 has an upper electrode 80, a lower electrode 82, and a photoelectric conversion film 84 disposed between the upper and lower electrodes 80 and 82. The upper electrode 80 needs to make light generated by the scintillator 62 incident on the photoelectric conversion film 84. Therefore, it is preferable that the upper electrode 80 be made of a conductive material that is at least transparent with respect to the emission wavelength of the scintillator 62.

The photoelectric conversion film 84 includes an organic photoconductor (OPC), and absorbs light emitted from the scintillator 62 and generates charge according to the absorbed light. When the photoelectric conversion film 84 includes the organic photoconductor, the photoelectric conversion film 84 has a sharp absorption spectrum in a visible light range, electromagnetic waves other than the light emitted from the scintillator 62 is hardly absorbed by the photoelectric conversion film 84, and noise that is generated by absorbing the radiation 16 by the photoelectric conversion film 84 can be effectively suppressed.

It is preferable that the absorption peak wavelength of the organic photoconductor forming the photoelectric conversion film 84 be close to the emission peak wavelength of the scintillator 62 in order to most effectively absorb light emitted from the scintillator 62. It is ideal that the absorption peak wavelength of the organic photoconductor is matched with the emission peak wavelength of the scintillator 62. However, when the difference between the absorption peak wavelength and the emission peak wavelength is small, the light that is emitted from the scintillator 62 can be sufficiently absorbed. Specifically, the difference between the absorption peak wavelength of the organic photoconductor and the emission peak wavelength of the scintillator 62 with respect to the radiation 16 is preferably 10 nm or less and more preferably, 5 nm or less.

Examples of the organic photoconductor that can satisfy the above-described conditions include a quinacridone-based organic compound and a phthalocyanine-based organic compound. For example, the absorption peak wavelength of quinacridone in the visible light range is 560 nm, and therefore, when quinacridone is used as the organic photoconductor and CsI(Ti) is used as the material forming the scintillator 62, the difference between the peak wavelengths can be decreased to 5 nm or less and the amount of charge generated by the photoelectric conversion film 84 can be substantially maximized.

An electromagnetic wave absorption/photoelectric conversion portion can be formed by an organic layer including a pair of the upper electrode 80 and the lower electrode 82 and the organic photoelectric conversion film 84 interposed between the upper electrode 80 and the lower electrode 82. Specifically, the organic layer can be formed by laminating or mixing, for example, an electromagnetic wave absorption portion, a photoelectric conversion portion, an electron transport portion, a hole transport portion, an electron blocking portion, a hole blocking portion, a crystallization prevention portion, an electrode, and an interlayer contact improvement portion. It is preferable that the organic layer include an organic p-type compound or an organic n-type compound.

The organic p-type compound (semiconductor) is a donor-type organic compound (semiconductor) whose representative example is a hole-transport-type organic compound and means an organic compound which readily donates electrons. Specifically, in a case in which two organic materials contact each other during use, one organic compound with low ionization potential is the organic p-type compound. Therefore, any organic compound may be used as the donor-type organic compound, as long as it has an electron donating property.

The organic n-type compound (semiconductor) is an acceptor-type organic compound (semiconductor) whose representative example is an electron-transport-type organic compound and means an organic compound which readily accepts electrons. Specifically, in a case in which two organic compounds contact each other during use, one organic compound with high electron affinity is the organic n-type compound. Therefore, any organic compound may be used as the acceptor-type organic compound, as long as it has an electron accepting property. Materials applicable to the organic p-type compound and the organic n-type compound and the configuration of the photoelectric conversion film 84 have been described in detail in JP-A No. 2009-32854 and thus a detailed description thereof will not be repeated here. The disclosure of JP-A No. 2009-32854 is incorporated by reference herein.

The lower electrode 82 is a thin film that is divided for each pixel unit. The lower electrode 82 may be appropriately made of a transparent or opaque conductive material, such as aluminum or silver. In the sensor unit 76, a predetermined bias voltage can be applied between the upper electrode 80 and the lower electrode 82 to move one of the charges (a hole and an electron) generated from the photoelectric conversion film 84 to the upper electrode 80 and move the other charge to the lower electrode 82. In the radiation detector 66 according to this exemplary embodiment, a wiring line is connected to the upper electrode 80 and the bias voltage is applied to the upper electrode 80 through the wiring line. It is assumed that the polarity of the bias voltage is determined such that the electron generated in the photoelectric conversion film 84 is moved to the upper electrode 80 and the hole is moved to the lower electrode 82. However, the polarity may be reversed.

The sensor unit 76 forming each pixel may include at least the lower electrode 82, the photoelectric conversion film 84, and the upper electrode 80. In order to prevent an increase in dark current, it is preferable that at least one of the electron blocking film 86 and the hole blocking film 88 be provided, and it is more preferable that both the electron blocking film 86 and the hole blocking film 88 be provided.

The electron blocking film 86 may be provided between the lower electrode 82 and the photoelectric conversion film 84. In a case in which the bias voltage is applied between the lower electrode 82 and the upper electrode 80, it is possible to suppress an increase in the dark current due to the injection of electrons from the lower electrode 82 into the photoelectric conversion film 84. The electron blocking film 86 may be made of an electron donating organic material. In actuality, the material used for the electron blocking film 86 may be selected according to a material forming the adjacent lower electrode 82 and a material forming the adjacent photoelectric conversion film 84. It is preferable that the material used for the electron blocking film 86 have an electron affinity (Ea) that is at least 1.3 eV higher than the work function (Wf) of the material forming the adjacent lower electrode 82 and have an ionization potential (Ip) equal to or less than that of the material forming the adjacent photoelectric conversion film 84. Materials applicable as the electron donating organic material have been described in detail in JP-A No. 2009-32854 and thus a detailed description thereof will not be repeated here.

The thickness of the electron blocking film 86 is preferably from 10 nm to 200 nm, more preferably from 30 nm to 150 nm, and most preferably from 50 nm to 100 nm in order to reliably obtain the effect of suppressing the dark current and prevent a decrease in the photoelectric conversion efficiency of the sensor unit 76.

The hole blocking film 88 may be provided between the photoelectric conversion film 84 and the upper electrode 80. In a case in which the bias voltage is applied between the lower electrode 82 and the upper electrode 80, it is possible to suppress an increase in the dark current due to the injection of holes from the upper electrode 80 into the photoelectric conversion film 84.

The hole blocking film 88 may be made of an electron accepting organic material. The thickness of the hole blocking film 88 is preferably from 10 nm to 200 nm, more preferably from 30 nm to 150 nm, and most preferably from 50 nm to 100 nm in order to reliably obtain the effect of suppressing the dark current and prevent a decrease in the photoelectric conversion efficiency of the sensor unit 76.

In actuality, the material used for the hole blocking film 88 may be selected according to a material forming the adjacent upper electrode 80 and a material forming the adjacent photoelectric conversion film 84. It is preferable that the material used for the hole blocking film 88 have an ionization potential (Ip) that is at least 1.3 eV higher than the work function (Wf) of the material forming the adjacent upper electrode 80 and have an electron affinity (Ea) equal to or more than that of the material forming the adjacent photoelectric conversion film 84. Materials applicable as the electron accepting organic material have been described in detail in JP-A No. 2009-32854 and thus a detailed description thereof will not be repeated here.

Figure 5:
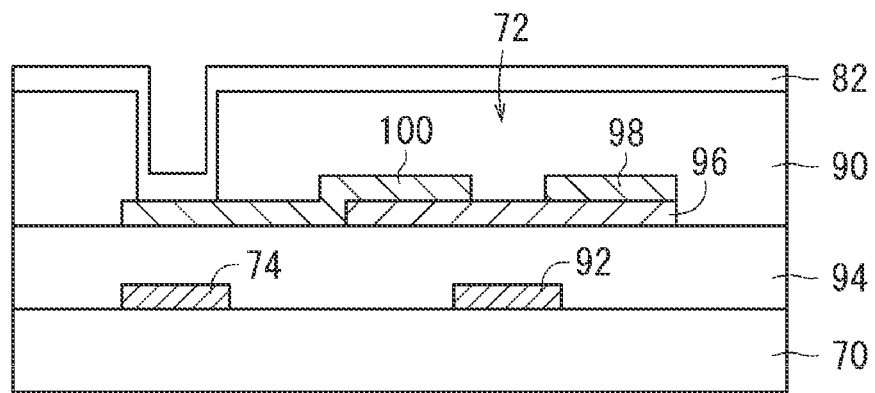
FIG. 5 is a schematic diagram illustrating the configuration of a TFT and a charge accumulation unit of FIG. 4.

FIG. 5 is a schematic diagram illustrating the configuration of the TFT 72 and the charge accumulation unit 74. The charge accumulation unit 74 that accumulates the charge moved to the lower electrode 82 and the TFT 72 that converts the charge accumulated in the charge accumulation unit 74 into an electric signal and outputs the electric signal are formed. A region in which the charge accumulation unit 74 and the TFT 72 are formed has a portion that overlaps the lower electrode 82 in plan view. By this configuration, the TFT 72 and the sensor unit 76 in each pixel overlap each other in the thickness direction. In order to minimize a plane area of the radiation detector 66, it is preferable that the region in which the charge accumulation unit 74 and the TFT 72 are formed is completely covered with the lower electrode 82.

The charge accumulation unit 74 is electrically connected to the corresponding lower electrode 82 through a conductive wiring line that is formed so as to pass through the insulating film 90 provided between the substrate 70 and the lower electrode 82. In this way, the charge captured by the lower electrode 82 can be moved to the charge accumulation unit 74.

The TFT 72 is formed by laminating a gate electrode 92, a gate insulating film 94, and an active layer (channel layer) 96 and providing a source electrode 98 and a drain electrode 100 on the active layer 96 with a predetermined gap therebetween. The active layer 96 may be made of an amorphous oxide. An oxide (for example, an In—O-based oxide) including at least one of In, Ga, and Zn is preferable as the amorphous oxide that can form the active layer 96. An oxide (for example, an In—Zn—O-based oxide, an In—Ga-based oxide, or a Ga—Zn—O-based oxide) including at least two of In, Ga, and Zn is more preferable as the amorphous oxide. An oxide including In, Ga, and Zn is most preferable as the amorphous oxide. As an In—Ga—Zn—O-based amorphous oxide, an amorphous oxide having a composition represented by $InGaO_3(ZnO)_m$ (m is a natural number smaller than 6) in a crystalline state is preferable, and $InGaZnO_4$ is more preferable.

When the active layer 96 of the TFT 72 is made of an amorphous oxide, the radiation 16, such as X-rays, is not absorbed. Even though the radiation 16 is absorbed, a very small amount of radiation is absorbed. Therefore, the generation of noise in the TFT 72 can be effectively suppressed. In this case, both the amorphous oxide that forms the active layer 96 of the TFT 72 and the organic photoconductor that forms the photoelectric conversion film 84 may be formed at the low temperature. Therefore, the substrate 70 is not limited to a substrate with high heat resistance, such as a semiconductor substrate, a quartz substrate, or a glass substrate, but a flexible substrate, such as a plastic substrate, an aramid substrate, or a bio-nanofiber substrate may be used as the substrate 70. Specifically, a flexible substrate made of the following materials may be used: polyester, such as polyethylene terephthalate, polyethylene phthalate, or polyethylene naphthalate, polystyrene, polycarbonate, polyether sulfone, polyarylate, polyimide, polycycloolefin, norbornene resin, and poly(chlorotrifluoroethylene). When the flexible substrate made of plastic is used, the weight of the substrate can be decreased. For example, this structure has an advantage in portability.

Since aramid can be applied to a high-temperature processing of 200 degrees or more, a transparent electrode material can be cured at a high temperature to have low resistance, and the aramid can respond to the automatic mounting of a driver IC including a solder reflow processing. In addition, the thermal expansion coefficient of aramid is close to that of indium tin oxide (ITO) and a glass substrate. Therefore, after an aramid substrate is manufactured, the warping of the aramid substrate is small and the aramid substrate is less likely to be cracked. In addition, the aramid can form the substrate 70 thinner than the glass substrate. The aramid may be laminated on a super-thin glass substrate to form the substrate 70.

The bio-nanofiber is a composite of a cellulose microfibril bundle generated by bacteria (Acetobacter Xylinum) (bacterial cellulose) and a transparent resin. The cellulose microfibril bundle has a width of 50 nm, a size of one-tenth of the visible light wavelength, high strength, high elasticity, and a low thermal expansion coefficient. A transparent resin, such as an acrylic resin or an epoxy resin, is impregnated into the bacterial cellulose and is then cured to obtain bio-nanofiber that has light transmittance of about 90% at a wavelength of 500 nm while including 60 to 70% of fiber. The bio-nanofiber has a low thermal expansion coefficient (3 to 7 ppm) equal to that of a silicon crystal, strength (460 MPa) similar to that of iron, high elasticity (30 GPa), and flexibility. Therefore, the bio-nanofiber can form the substrate 70 thinner than the glass substrate.

In this exemplary embodiment, the TFT 72, the charge accumulation unit 74, the sensor unit 76, and the transparent insulating film 78 are sequentially formed on the substrate 70 and the scintillator 62 is bonded to the substrate 70 by an adhesive resin with low light absorptance, thereby forming the radiation detector 66. Hereinafter, the substrate 70 including the films up to the transparent insulating film 78 formed thereon is referred to as the radiation conversion panel 64.

In the radiation detector 66, the photoelectric conversion film 84 is made of an organic photoconductor and the radiation 16 is hardly absorbed by the photoelectric conversion film 84. Therefore, in the radiation detector 66 according to this exemplary embodiment, even in a case in which the radiation 16 passes through the radiation conversion panel 64 by back surface irradiation, the amount of radiation 16 absorbed by the photoelectric conversion film 84 can be decreased. Therefore, a decrease in sensitivity for the radiation 16 can be suppressed. In the back surface irradiation, the radiation 16 passes through the radiation conversion panel 64 and reaches the scintillator 62. However, in a case in which the photoelectric conversion film 84 of the radiation conversion panel 64 is made of an organic photoconductor, the radiation 16 is hardly absorbed by the photoelectric conversion film 84 and the attenuation of the radiation 16 can be suppressed. The radiation detector 66 is suitable for the back surface irradiation.

Figure 6:
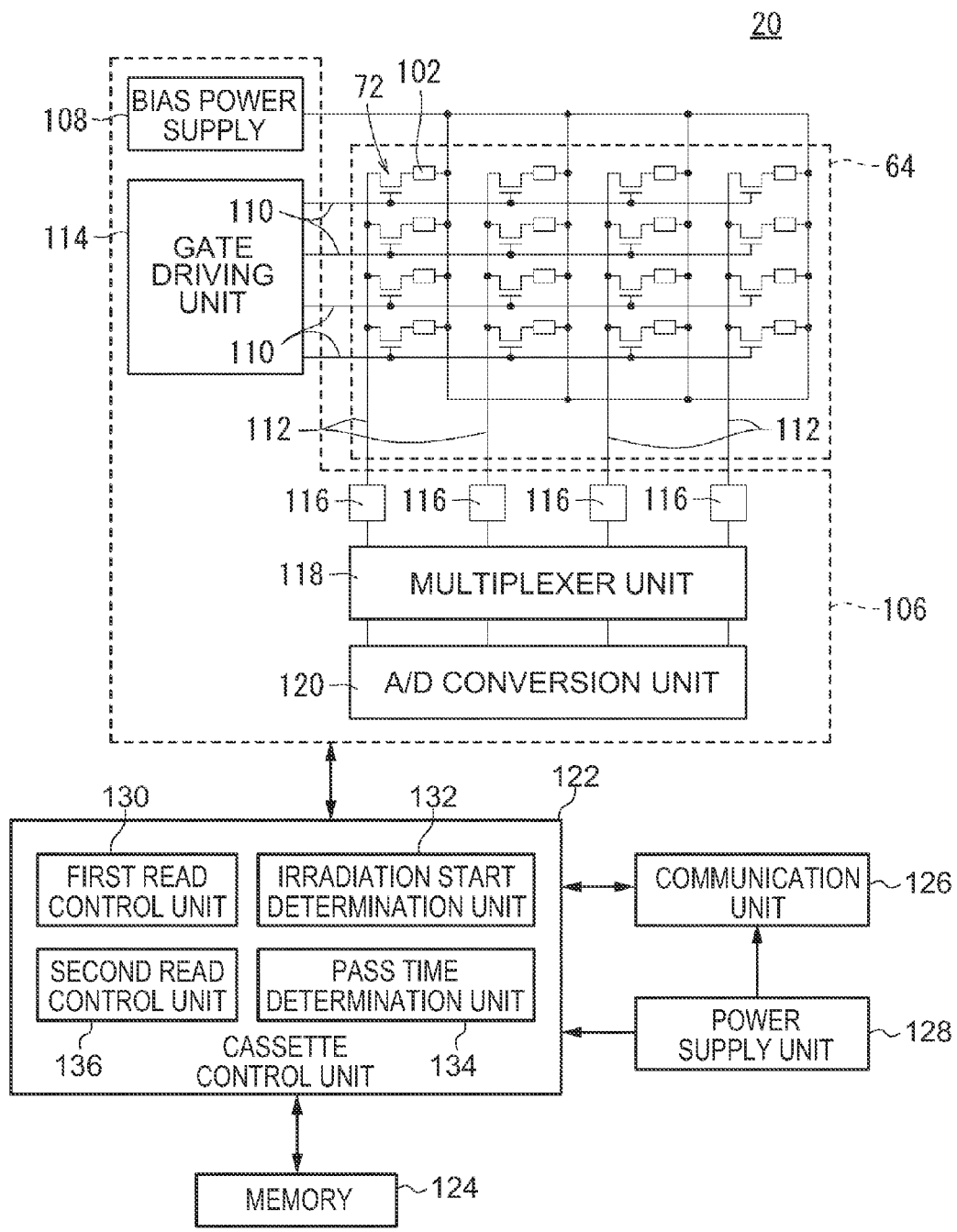
FIG. 6 is the schematic diagram illustrating the electric configuration of the electronic cassette of FIG. 1.

FIG. 6 is a schematic diagram illustrating the electric configuration of the electronic cassette 20 of FIG. 1. The electronic cassette 20 has a structure in which the pixels 102 are arranged on the TFTs 72 in a matrix. Each of the pixels 102 is arranged in a matrix and has a photoelectric conversion element (not illustrated in the drawings). In each pixel 102 that is applied with a bias voltage from the bias power supply 108 forming the driving circuit unit 106, the charge that is generated by executing photoelectric conversion of visible light is accumulated. By sequentially turning on the TFTs 72 for each column, a charge signal (electric signal) can be read as a pixel value of an analog signal through each signal line 112. In FIG. 6, in order to simplify the description, the pixels 102 and the TFTs 72 are arranged in a matrix of 4×4 in vertical and horizontal directions. However, in actuality, the pixels 102 and the TFTs 72 are arranged in a matrix of 2880×2304 in vertical and horizontal directions.

The TFT 72 that is connected to each pixel 102 is connected to a gate line 110 that extends in a row direction and a signal line 112 that extends in a column direction. Each gate line 110 is connected to the gate driving unit 114 forming the driving circuit unit 106 and each signal line 112 is connected to the multiplexer unit 118 forming the driving circuit unit 106, through the charge amplifier 116. The multiplexer unit 118 is connected to an A/D conversion unit 120 that converts an electric signal of an analog signal into an electric signal of a digital signal. The A/D conversion unit 120 outputs the electric signal (pixel value of the digital signal, hereinafter, it may be called a digital value) that is converted into the digital signal, to the cassette control unit 122.

The cassette control unit 122 wholly controls the electronic cassette 20, and includes a clock circuit (not illustrated in the drawings) and functions as a timer. If a predetermined program is read by an information processing device such as a computer, the computer can function as the cassette control unit 122 according to this exemplary embodiment.

The cassette control unit 122 is connected to a memory 124 and a communication unit 126. The memory 124 stores a pixel value of a digital signal and the communication unit 126 exchanges a signal with the system controller 24. The communication unit 126 transmits one image (image of one frame) that is formed by arranging the plural pixels in a matrix, to the system controller 24 in a form of packets, in a row unit. The power supply unit 128 supplies power to the cassette control unit 122, the memory 124, and the communication unit 126. The bias power supply 108 supplies the power transmitted from the cassette control unit 122, to each pixel 102.

The cassette control unit 122 has a first read control unit 130, an irradiation start determination unit 132, a passage time determination unit 134, and a second read control unit 136. The first read control unit 130 executes a scan mode (first read mode or simply called read mode) in which the charge accumulated in the pixels 102 is simultaneously read in a unit of plural rows (lines) and the charge accumulated in each pixel 102 is read. The first read control unit 130 controls the gate driving unit 114, the charge amplifier 116, the multiplexer unit 118, and the A/D conversion unit 120, and executes the scan mode.

The scan mode that corresponds to the first read mode is a high-speed read mode in which image data of one frame can be read in short time, as compared with a sequential read mode corresponding to a second read mode to be described below.

Hereinafter, a concept of the scan mode will be described. If the scan mode is executed, the gate driving unit 114 outputs gate signals to the gate lines 110 of the zero-th row and the second row, turns on the TFTs 72 of the zero-th row and the second row (activates the TFTs 72 of the zero-th row and the second row), and simultaneously reads the charge that is accumulated in the pixels 102 of the zero-th row and the second row through the signal lines 112. The read charge of each column is output as charge signals (pixel values) to the charge amplifier 116 of each column. In this case, since the charge accumulated in the pixels 102 of the zero-th row and the second row is simultaneously read, the electric signal that is input to the charge amplifier 116 is an electric signal that is obtained by adding the electric signals accumulated in the pixels 102 of the zero-th row and the second row. That is, the electric signals that are accumulated in the pixels 102 of the zero-th row and the second row are added for each column and the added electric signal is output to the charge amplifier 116 for each column. Thereby, the charge of the pixels 102 of the zero-th row and the second row can be added and read.

The charge amplifier 116 coverts the input charge signal into a voltage signal and outputs the voltage signal to the multiplexer unit 118. The multiplexer unit 118 sequentially selects the input voltage signal and outputs the voltage signal to the A/D conversion unit 120, and the A/D conversion unit 120 converts the input voltage signal into a digital signal and outputs the digital signal. Thereby, the electric signals (pixel values) that are accumulated in the pixels 102 of the zero-th row and the second row are added for each column and are output as an electric signal (pixel value) of the digital signal from the A/D conversion unit 120. The electric signal (pixel value) of the digital signal that is output from the A/D conversion unit 120 is transmitted to the cassette control unit 122 and the cassette control unit 122 stores the transmitted digital value in the memory 124. That is, in the memory 124, image data where the image data of the zero-th row and the second row are added for each column is stored.

If the gate driving unit 114 reads the charge accumulated in the pixels 102 of the zero-th row and the second row as described above, the gate driving unit 114 transmits gate signals to the gate lines 110 of the first and third rows, turns on the TFTs 72 of the first and third rows (activates the TFTs 72 of the first and third rows), and simultaneously reads the charge (electric signals) that is accumulated in the pixels 102 of the first and third rows through the signal lines 112. The read electric signals are transmitted as digital signals to the cassette control unit 122 through the above-described operation and are stored in the memory 124.

If the irradiation start determination unit 132 to be described below determines that irradiation of the radiation 16 starts, the first read control unit 130 ends execution of the scan mode. At this time, in a case in which read of the image data of one frame does not end, the first read control unit 130 ends the execution of the scan mode after the read of the image data of one frame ends.

As such, since the charge accumulated in the pixels 102 is read in the scan mode, the image data of one frame can be read in short time and the noise charge that is accumulated in the pixels 102 can be removed in short time. The charge accumulated in the pixels 102 is read in the scan mode. Therefore, even in a case in which it is determined that the irradiation of the radiation 16 starts, a state can be immediately transited to an exposure state and the radiation 16 having image information is not wasted. In contrast, in a case in which the noise charge accumulated in the pixels 102 in the sequential read mode to be described below is removed, time may be needed to read image data of one frame. In a case in which it is determined that the irradiation of the radiation 16 starts during read of the image data of one frame, the state cannot be immediately transited to the exposure state and the radiation 16 having the image information may be wasted.

The irradiation start determination unit 132 determines whether the digital value read by the first read control unit 130 and stored in the memory 124 is more than a threshold value. In a case in which the digital value is more than the threshold value, the irradiation start determination unit 132 determines that the irradiation of the radiation 16 starts. That is, the irradiation start determination unit 132 detects the radiation 16 according to whether the obtained digital value is more than the threshold value. In a case in which the radiation 16 is not irradiated, the charge that is accumulated in the pixels 102 is the noise and is very small. If the radiation 16 is irradiated and is incident on the electronic cassette 20, the amount of charge that is accumulated in the pixels 102 becomes more than the amount of charge in a case in which the radiation 16 is not irradiated. Therefore, in a case in which a value of the electric signal read in the scan mode and converted into the digital signal is more than the threshold value, it can be determined that the irradiation of the radiation 16 starts.

Since the charge accumulated in the pixels 102 is simultaneously read in a unit of plural rows in the scan mode, the start of irradiation of the radiation 16 can be determined early and accurately. That is, if the charge of the pixels 102 is added and the radiation 16 is irradiated, the electric signal of the obtained digital signal greatly increases and thus the start of irradiation of the radiation 16 can be determined early. In contrast, if the charge accumulated in the pixels 102 is not added and the threshold value is decreased, the start of irradiation of the radiation 16 can be detected early. However, a ratio of the noise of the electric signal with respect to the threshold value increases, and the start of irradiation of the radiation 16 cannot be detected accurately. The threshold value may be arbitrarily set by the user.

The passage time determination unit 134 determines whether a predetermined time passes after the irradiation of the radiation 16 starts. The predetermined time may be time when the radiation source 34 irradiates the radiation 16 or exposure time of the radiation 16 to capture a radiation image by the electronic cassette 20. The predetermined time is stored in the memory 124.

The second read control unit 136 executes the sequential read mode (second read mode) in which the electric signals accumulated in the pixels 102 are sequentially read in a row unit. The second read control unit 136 controls the gate driving unit 114, the charge amplifier 116, the multiplexer unit 118, and the A/D conversion unit 120, and executes the sequential read mode.

Hereinafter, a concept of the sequential read mode will be described. If the sequential read mode is executed, the gate driving unit 114 outputs a gate signal to the gate line 110 of the zero-th row, turns on the TFT 72 of the zero-th row (activates the TFT 72 of the zero-th row), and reads the charge that is accumulated in the pixels 102 of the zero-th row through each signal line 112. The read charge of each column is output as a charge signal (pixel value) to the charge amplifier 116 of each column and is converted into a voltage signal. The converted voltage signal is output to the multiplexer unit 118, and the electric signal (pixel value) that is accumulated in the pixels 102 of the zero-th row is transmitted as the digital signal to the cassette control unit 122 by the A/D conversion unit 120, and is stored in the memory 124. That is, image data of the zero-th row is stored in the memory 124.

If the gate driving unit 114 reads the charge accumulated in the pixels 102 of the zero-th row, the gate driving unit 114 transmits a gate signal to the gate line 110 of the first row, turns on the TFT 72 of the first row (activates the TFT 72 of the first row), and simultaneously reads the charge (electric signal) that is accumulated in the pixels 102 of the first row through each signal line 112. The read electric signal is transmitted as a digital signal to the cassette control unit 122 through the above-described operation and is stored in the memory 124.

If the gate driving unit 114 reads the charge accumulated in the pixels 102 of the first row, the gate driving unit 114 reads the charge that is accumulated in the pixels 102 of the second row and reads the charge that is accumulated in the pixels 102 of the third row.

The cassette control unit 122 sequentially transmits image data of one row stored in the memory 124, to the system controller 24 through the communication unit 126. That is, the cassette control unit 122 sequentially transmits the image data of one row in a row unit. The cassette control unit 122 may collectively transmit image data of one frame, instead of the row unit.

Figure 7:
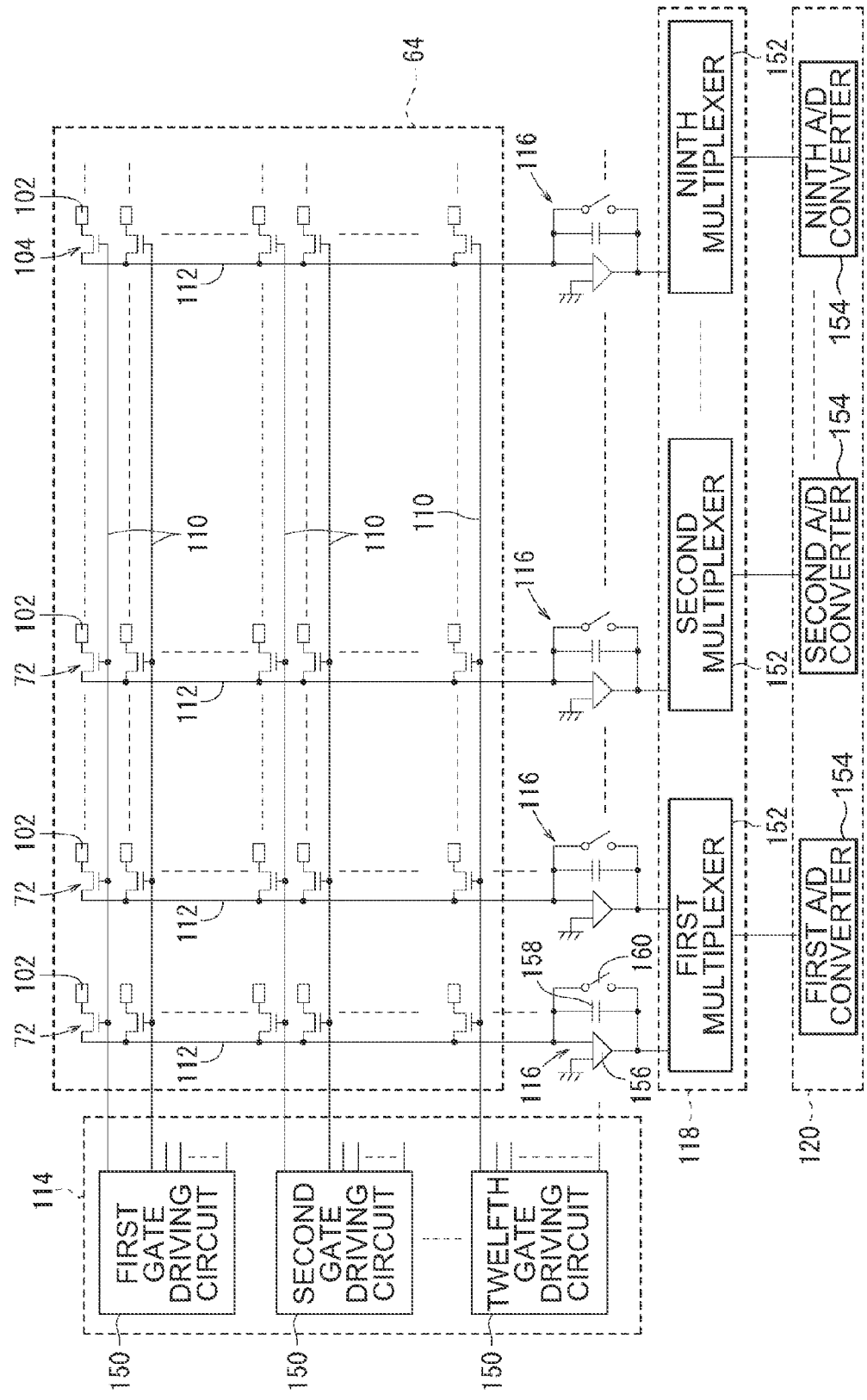
FIG. 7 is a diagram illustrating the detailed configuration of a radiation conversion panel, a gate driving unit, a charge amplifier, and a multiplexer unit of FIG. 6.

FIG. 7 is a diagram illustrating the detailed configuration of the radiation conversion panel 64, the gate driving unit 114, the charge amplifier 116, and the multiplexer unit 118 of FIG. 6. The gate driving unit 114 has 12 gate driving circuits 150 (first to twelfth gate driving circuits 150) and each gate driving circuit 150 is connected to 240 gate lines 110. Each gate driving circuit 150 reads the charge that is accumulated in the pixels 102 connected to the 240 gate lines 110 connected to each gate driving circuit through the TFTs 72. That is, each gate driving circuit 150 reads the charge that is accumulated in the pixels 102 of a read region (zero-th to 239-th rows) of each gate driving circuit. The first to twelfth gate driving circuits 150 are collectively called the gate driving circuit 150.

The multiplexer unit 118 has 9 multiplexers 152 (first to ninth multiplexers 152) and each multiplexer 152 is connected to 256 signal lines 112. To each multiplexer 152, charge signals of the pixels 102 of a management region (first to 255-th columns) of each multiplexer are input through the charge amplifier 116. The first to ninth multiplexers 152 are collectively called the multiplexer 152. As such, the radiation conversion panel 64 has the pixels 102 and the TFTs 72 that are arranged in a matrix of 2880 (240×12)×2304 (256×9) in vertical and horizontal directions.

The A/D conversion unit 120 has 9 A/D converters 154 (first to ninth A/D converters 154), and the voltage signal that is output by each multiplexer 152 is output to each A/D converter 154. Specifically, the voltage signal that is output by the first multiplexer 152 is output to the first A/D converter 154 and the voltage signal that is output by the second multiplexer 152 is output to the second A/D converter 154. As such, the voltage signal that is output by each multiplexer 152 is output to the A/D converter 154 that corresponds to each multiplexer 152. The A/D converter 154 converts the input voltage signal into a voltage signal of a digital signal. The first to ninth A/D converters 154 are collectively called the A/D converter 154.

Each gate driving circuit 150 sequentially turns on the TFTs 72 in a row unit. Thereby, the charge that is accumulated in the pixels 102 is sequentially read in a row unit and is output as the charge signal to the charge amplifier 116 through the signal line 112. Specifically, each gate driving circuit 150 selects the gate line 110 of the zero-th row (row to be first read), among the plural gate lines 110 connected to each gate driving circuit. Each gate driving circuit 150 outputs a gate signal to the selected gate line 110, turns on the TFTs 72 of the zero-th row, and reads the charge accumulated in the pixels 102 of the zero-th row. If the charge accumulated in the pixels 102 of the zero-th row is read, each gate driving circuit 150 selects the gate line 110 of the first row (row to be second read), outputs a gate signal to the selected gate line 110, turns on the TFTs 72 of the first row, and reads the charge accumulated in the pixels 102 of the first row. Each gate driving circuit 150 sequentially selects the gate lines 110 of the second, third, . . . , and 239-th rows (row to be finally read), outputs the gate signal to the selected gate lines 110, sequentially turns on the TFTs 72 in a row unit, and reads the charge accumulated in the pixels 102 of each row.

The read charge of each row is input to the charge amplifier 116 of each column through each signal line 112. Each charge amplifier 116 includes an operational amplifier 156, a capacitor 158, and a switch 160. In a case in which the switch 160 is turned off, the charge amplifier 116 converts the charge signal input to the operational amplifier 156 into a voltage signal and outputs the voltage signal. The charge amplifier 116 amplifies an electric signal with gain set by the cassette control unit 122 and outputs the electric signal. In a case in which the switch 160 is turned on, the charge that is accumulated in the capacitor 158 is discharged by a closed circuit of the capacitor 158 and the switch 160, and the charge that is accumulated in the pixels 102 is discharged to the ground potential (GND) through the closed switch 160 and the operational amplifier 156. The operation of turning on the switch 160 and discharging the charge accumulated in the pixels 102 to the GND is called a reset operation (idle read operation). That is, in a case of the reset operation, the voltage signal that corresponds to the charge signal accumulated in the pixels 102 is removed without being output to the multiplexer unit 118 and the A/D conversion unit 120. In this exemplary embodiment, in a case of "read of the charge accumulated in the pixels 102", the voltage signal that corresponds to the charge accumulated in the pixels 102 is output to the multiplexer unit 118 and the A/D conversion unit 120.

The voltage signal that is converted by each charge amplifier 116 is output to each multiplexer 152. The multiplexer 152 sequentially selects the plural input voltage signals and outputs the voltage signals, according to a control signal from the cassette control unit 122. Each A/D converter 154 converts the voltage signal output from each multiplexer 152 into a digital signal, and outputs the converted digital signal to the cassette control unit 122.

Figure 8:
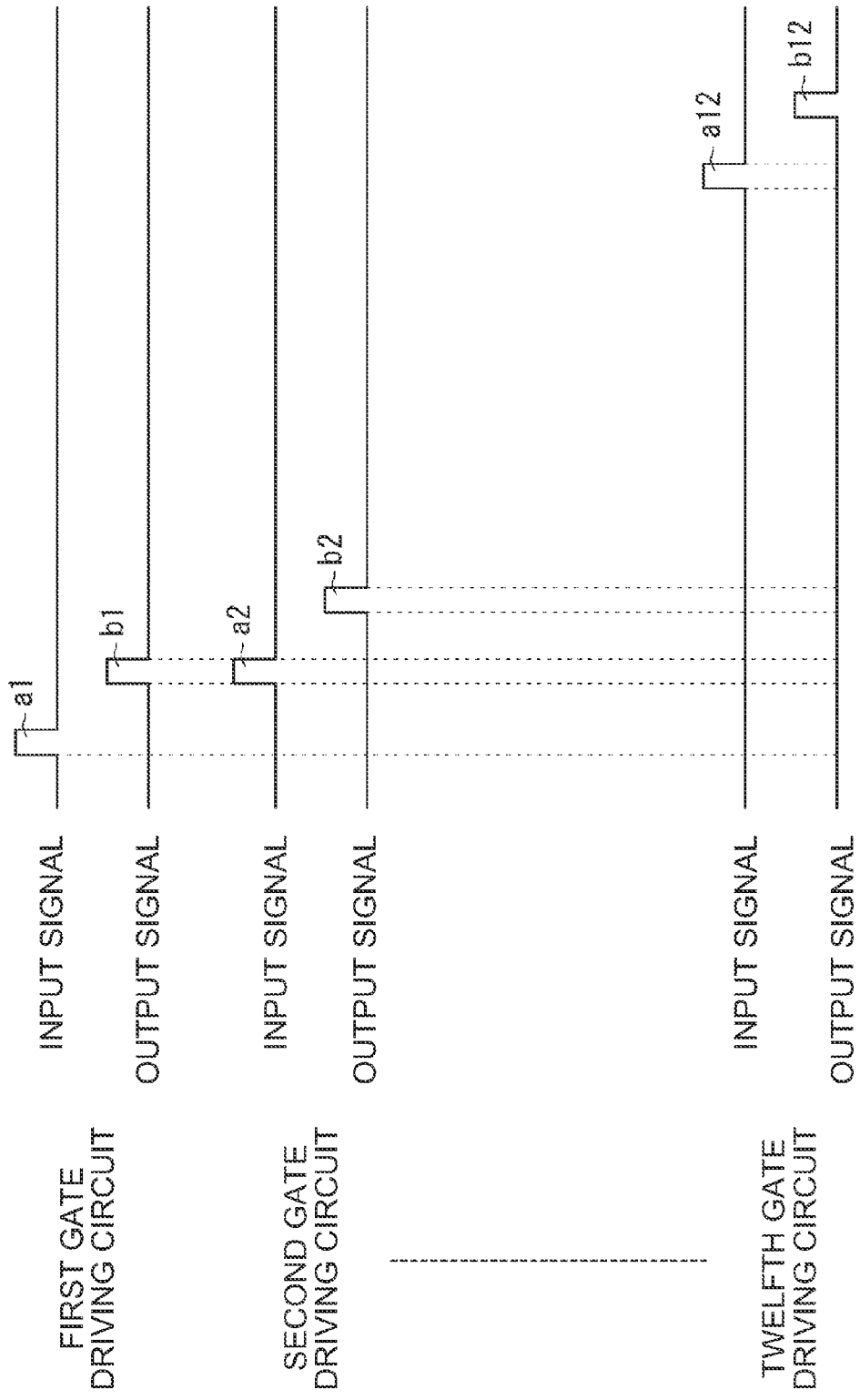
FIG. 8 is a time chart of an input signal input from a cassette control unit to a gate driving unit and an output signal output from the gate driving unit to the cassette control unit, in a sequential read mode.

FIG. 8 is a diagram illustrating a time chart of an input signal input from the cassette control unit 122 to the gate driving unit 114 and an output signal output from the gate driving unit 114 to the cassette control unit 122, in the sequential read mode. In a normal read mode, the cassette control unit 122 outputs an input signal (driving signal) a1 to the first gate driving circuit 150. If the driving signal a1 is input to the first gate driving circuit 150, the first gate driving circuit 150 sequentially selects the gate lines 110 managed by the first gate driving circuit from the zero-th row, and outputs a gate signal to the selected gate line 110. Thereby, the TFTs 72 are sequentially turned on in a row unit and the charge that is accumulated in the pixels 102 is read in a row unit. If the first gate driving circuit 150 selects the final row (239-th row), the first gate driving circuit 150 outputs an output signal (end signal) b1 to the cassette control unit 122. If the cassette control unit 122 receives the end signal b1, the cassette control unit 122 outputs an input signal (driving signal) a2 to the second gate driving circuit 150.

If the input signal a2 is input to the second gate driving circuit 150, the second gate driving circuit 150 sequentially selects the gate lines 110 managed by the second gate driving circuit from the zero-th row, and outputs a gate signal to the selected gate line 110. Thereby, the TFTs 72 are sequentially turned on in a row unit and the charge that is accumulated in the pixels 102 is read in a row unit. If the second gate driving circuit 150 selects the final row (239-th row), the second gate driving circuit 150 outputs an output signal (end signal) b2 to the cassette control unit 122. If the cassette control unit 122 receives the end signal b2, the cassette control unit 122 inputs an input signal (driving signal) a3 to the third gate driving circuit 150. This operation is executed up to the twelfth gate driving circuit 150.

As such, the driving signals a1 to a12 are input from the first gate driving circuit 150 to the twelfth gate driving circuit 150 to sequentially drive the individual gate driving circuits 150, and the charge that is accumulated in the pixels 102 is sequentially read in a row unit. Thereby, the charge that is accumulated in the pixels 102 of the zero-th to 2879-th rows of the radiation conversion panel 64 is sequentially read in a row unit from the zero-th row. In the sequential read mode, if an image quality of the captured radiation image is considered, time of about 173 μsec is needed to read the charge accumulated in the pixels 102 of one row. Therefore, in the sequential read mode, time of about 500 msec (173 μsec/1× 2880 lines) is needed to read the charge accumulated in the pixels 102 of all rows (2880 rows).

Figure 9:
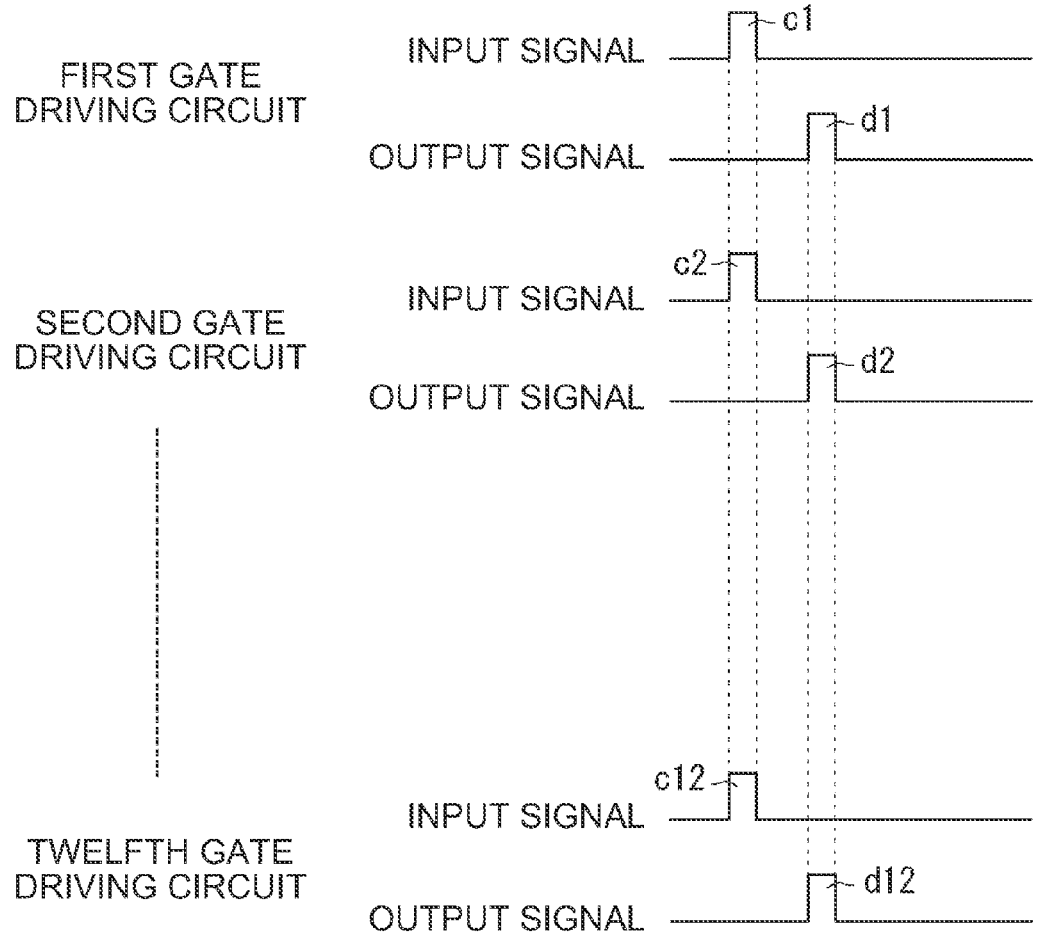
FIG. 9 is a time chart of an input signal input from the cassette control unit to the gate driving unit and an output signal output from the gate driving unit to the cassette control unit, in a scan mode.

FIG. 9 is a time chart of an input signal input from the cassette control unit 122 to the gate driving unit 114 and an output signal output from the gate driving unit 114 to the cassette control unit 122, in the scan mode. In the scan mode, the cassette control unit 122 simultaneously outputs the input signals c1 to c12 to the first to twelfth gate driving circuits 150. If the driving signals c1 to c12 are input to the first to twelfth gate driving circuits 150, the first to twelfth gate driving circuits 150 sequentially select the gate lines 110 managed by the first to twelfth gate driving circuits from the zero-th row, and output gate signals to the selected gate lines 110. Thereby, the TFTs 72 of regions that are managed by the gate driving circuits 150 are sequentially turned on in a row unit and the charge that is accumulated in the pixels 102 of the regions managed by the gate driving circuits 150 is sequentially read in a row unit.

Specifically, the charge that is accumulated in the pixels 102 of the zero-th row of the region managed by each gate driving circuit 150 is simultaneously read and the charge that is accumulated in the pixels 102 of the first row is simultaneously read. As such, the charge that is accumulated in the pixels 102 of the region managed by each gate driving circuit 150 is simultaneously read in a row unit. Therefore, the charge of the pixels 102 read by each gate driving circuit 150 is added for each column. For example, in a case in which each gate driving circuit 150 simultaneously reads the charge of the pixels 102 of the zero-th row, the read charge of the pixels 102 of the zero-th row is added for each column. The charge that is added for each column is input to the charge amplifier 116 of each column. If each gate driving circuit 150 selects the final row (239-th row), each gate driving circuit 150 outputs the output signals (end signals) d1 to d12 to the cassette control unit 122.

In the scan mode, time that is needed to read the charge accumulated in the pixels 102 needs to be decreased. If the time needed to read the charge is excessively decreased, the surplus charge that is accumulated in the pixels 102 cannot be removed, and a radiation image that has a superior image quality cannot be captured. In order to satisfy both the requests, the charge that is accumulated in the pixels 102 is read for one row, in time of 21 μsec. Therefore, in the scan mode, time of about 5 msec (21 μsec×2880 lines×(1/12)) is needed to read the charge accumulated in the pixels 102 of all rows (2880 rows). This means that the charge accumulated in all of the pixels 102 can be read in about 1/100 time of the time needed in the sequential read mode. In this case, 21 μsec× 2880 lines is multiplied with (1/12), because the charge accumulated in the pixels 102 is simultaneously read in a unit of 12 rows, in the scan mode.

That is, the electronic cassette 20 includes at least the plural pixels 102 that are arranged in a matrix, the plural TFTs 72 that are arranged in a matrix to read the electric signals accumulated in the plural pixels 102, the plural gate lines 110 that are connected to the TFTs 72 of each row and are arranged in parallel to a row direction, the plural gate driving circuits 150 that are connected to the plural gate lines 110, outputs the gate signals to the TFTs 72 of each row through the gate lines 110, and are arranged in parallel along a column direction, and the plural signal lines 112 that read the electric signals accumulated in the plural pixels 102 and are arranged in parallel to the column direction.

A gate of the TFT 72 is connected to the gate line 110 and a source thereof is connected to the pixel 102. A drain of the TFT 72 is connected to the signal line 112. If the driving signal a or c is input to each gate driving circuit 150, each gate driving circuit 150 sequentially selects the gate lines 110 connected to each gate driving circuit, outputs a gate signal to the selected gate line 110, turns on the TFT 72, and sequentially reads the electric signal accumulated in the pixels 102 connected to each gate driving circuit through the plural signal lines 112, in a row unit.

The first read control unit 130 executes the scan mode in which the driving signal c is simultaneously input to each gate driving circuit 150 and the electric signals accumulated in the plural pixels 102 are simultaneously read in a unit of plural rows.

The second read control unit 136 of the cassette control unit 122 executes the sequential read mode in which the driving signal a is sequentially input to each gate driving circuit 150 to drive each gate driving circuit 150 and the electric signals of the plural pixels 102 are sequentially read in a unit of one row.

Figure 10:
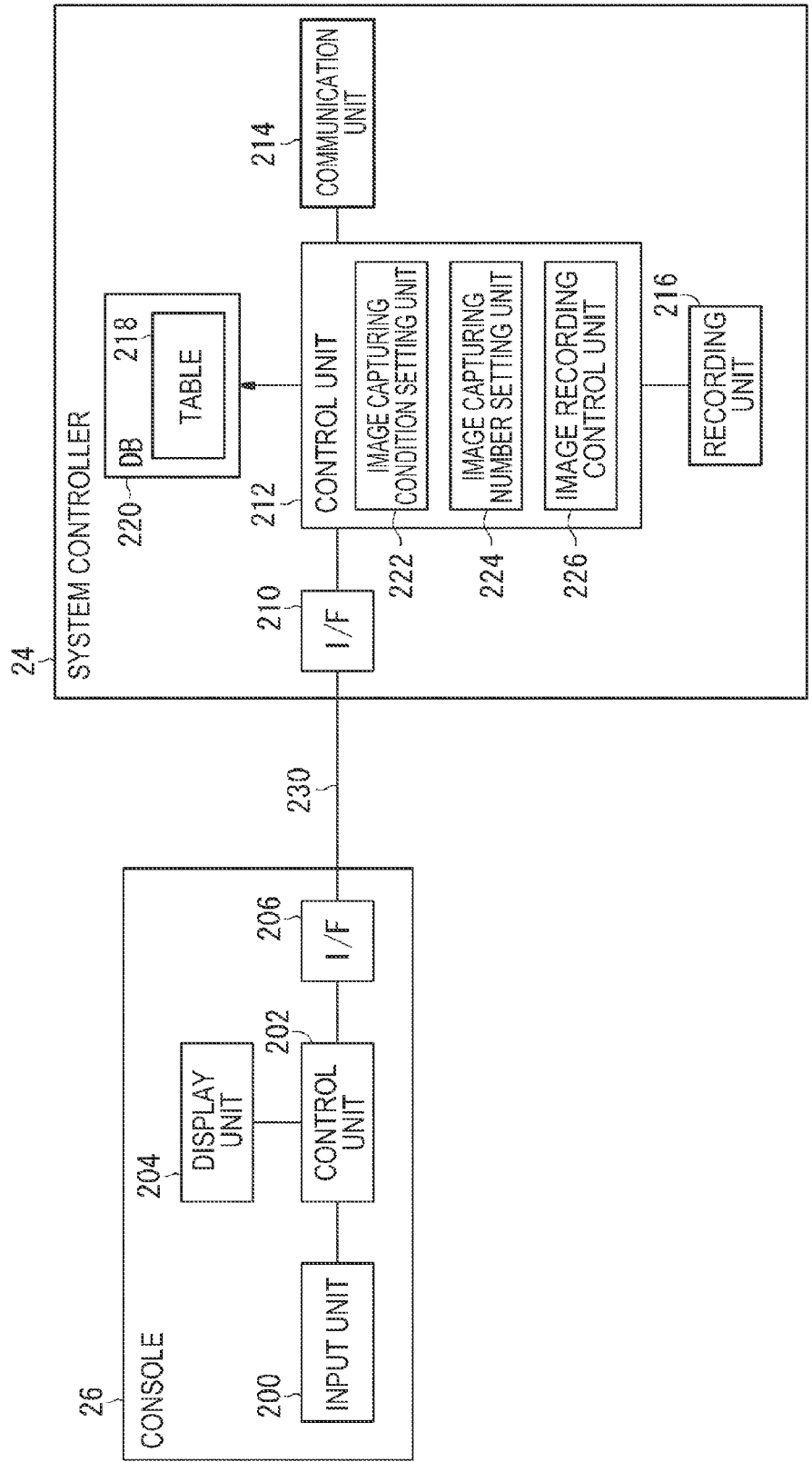
FIG. 10 is a schematic diagram illustrating the electric configuration of a system controller and a console.

FIG. 10 is a schematic diagram illustrating the electric configuration of the system controller 24 and the console 26. The console 26 has an input unit 200 that receives an input operation of the user, a control unit 202 that wholly controls the console 26, a display unit 204 that displays an image to support the input operation of the user, and an interface I/F 206 that exchanges a signal with the system controller 24.

The system controller 24 has an interface I/F 210 that exchanges a signal with the console 26, a control unit 212 that wholly controls the radiation image capturing system 10, a communication unit 214 that exchanges a signal with the electronic cassette 20 and the display unit 28 through wireless communication, a recording unit 216 that records image data and a program transmitted from the electronic cassette 20 through the communication unit 214, and a database 220 that has a table 218 where image capturing conditions including irradiation time of the radiation 16 are stored and associated with an image capturing part and a diagnosis part. The interface I/F 206 and the interface I/F 210 are connected by a cable 230. The input unit 200 includes a mouse and a keyboard (not illustrated in the drawings), and outputs the operation signal input by the user to the control unit 202.

The control unit 202 displays a screen to allow the user to input the image capturing part, the diagnosis part, and the image capturing number and makes the display unit 204 function as a graphical user interface (GUI). The doctor operates the input unit 200 and selects the image capturing part, the diagnosis part, and the image capturing number, while viewing an image (screen of the display unit 204) displayed on the display unit 204. In this case, the image capturing part is a part of a body of a patient on which a radiation image is captured. Examples of the image capturing part include a chest, a lower abdominal part, or feet. The diagnosis part indicates a part that is diagnosed using an image obtained by radiation image capturing. For example, even though the image capturing part is the same as the chest, the diagnosis parts are different from each other, like a circulatory organ, a rib, and a heart.

The control unit 202 outputs the image capturing part, the diagnosis part, and the image capturing number selected by the user to the control unit 212 of the system controller 24 through the interfaces I/F 206 and 210. An image capturing condition setting unit (irradiation time setting unit) 222 of the control unit 212 sets image capturing conditions corresponding to the image capturing part and the diagnosis part (selected by the user) transmitted from the console 26. Specifically, the image capturing condition setting unit 222 reads the image capturing conditions corresponding to the image capturing part and the diagnosis part selected by the user from the table 218, and sets the read image capturing conditions as image capturing conditions of radiation image capturing to be executed in the future. The image capturing condition setting unit 222 transmits at least irradiation time among the set image capturing conditions to the electronic cassette 20 through the communication unit 214. The electronic cassette 20 stores the transmitted irradiation time in the memory 124. The stored irradiation time becomes the predetermined time.

The image capturing number setting unit 224 of the control unit 212 sets the image capturing number that is transmitted from the console 26 (selected by the user). The image capturing number setting unit 224 transmits the set image capturing number to the electronic cassette 20 through the communication unit 214. The electronic cassette 20 stores the transmitted image capturing number in the memory 124. The image recording control unit 226 of the control unit 212 records image data of one frame transmitted from the electronic cassette 20 through the communication unit 214, in the recording unit 216.

FIG. 11 is a diagram illustrating an example of the table 218. In the table 218, image capturing conditions, such as an irradiation time, a tube voltage, and a tube current, are recorded to correspond to the image capturing part and the diagnosis parts. The plural diagnosis parts exist in the image capturing part and the image capturing conditions are recorded to correspond to the diagnosis parts. For example, in a case in which the image capturing part is the chest, plural diagnosis parts such as a circulatory organ, a rib, and a heart are set, and image capturing conditions are recorded to correspond to the diagnosis parts. In a case in which the image capturing part is the chest and the diagnosis part is the circulatory organ, an irradiation time 200 msec, a tube voltage becomes 100 kV, and a tube current becomes 10 mA. The user may operate the input unit 200 of the console 26 and arbitrarily change information that is recorded in the table 218.

Figure 12:
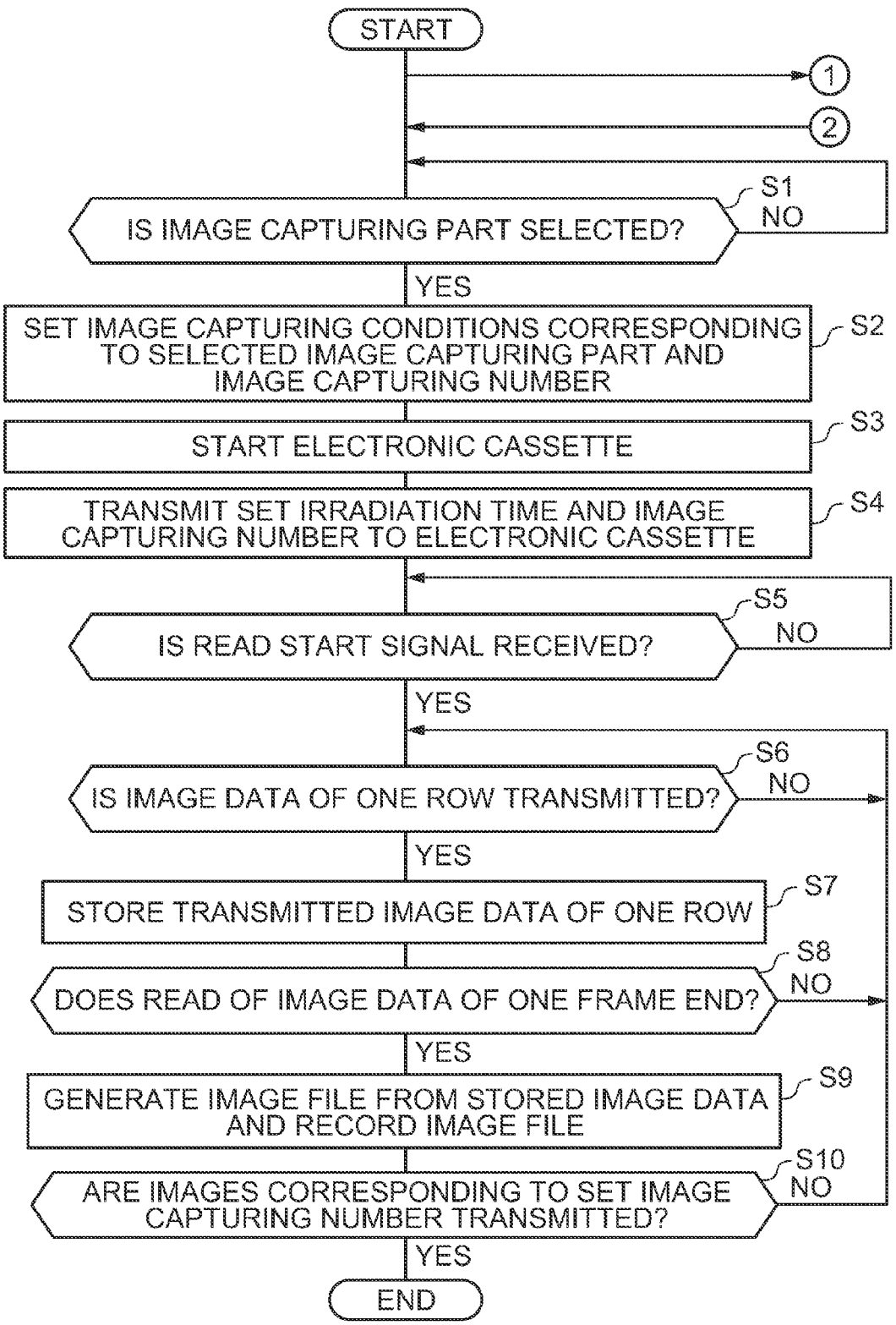
FIG. 12 is a flowchart illustrating an operation of a system controller and a console of a radiation image capturing system.
Figure 13:
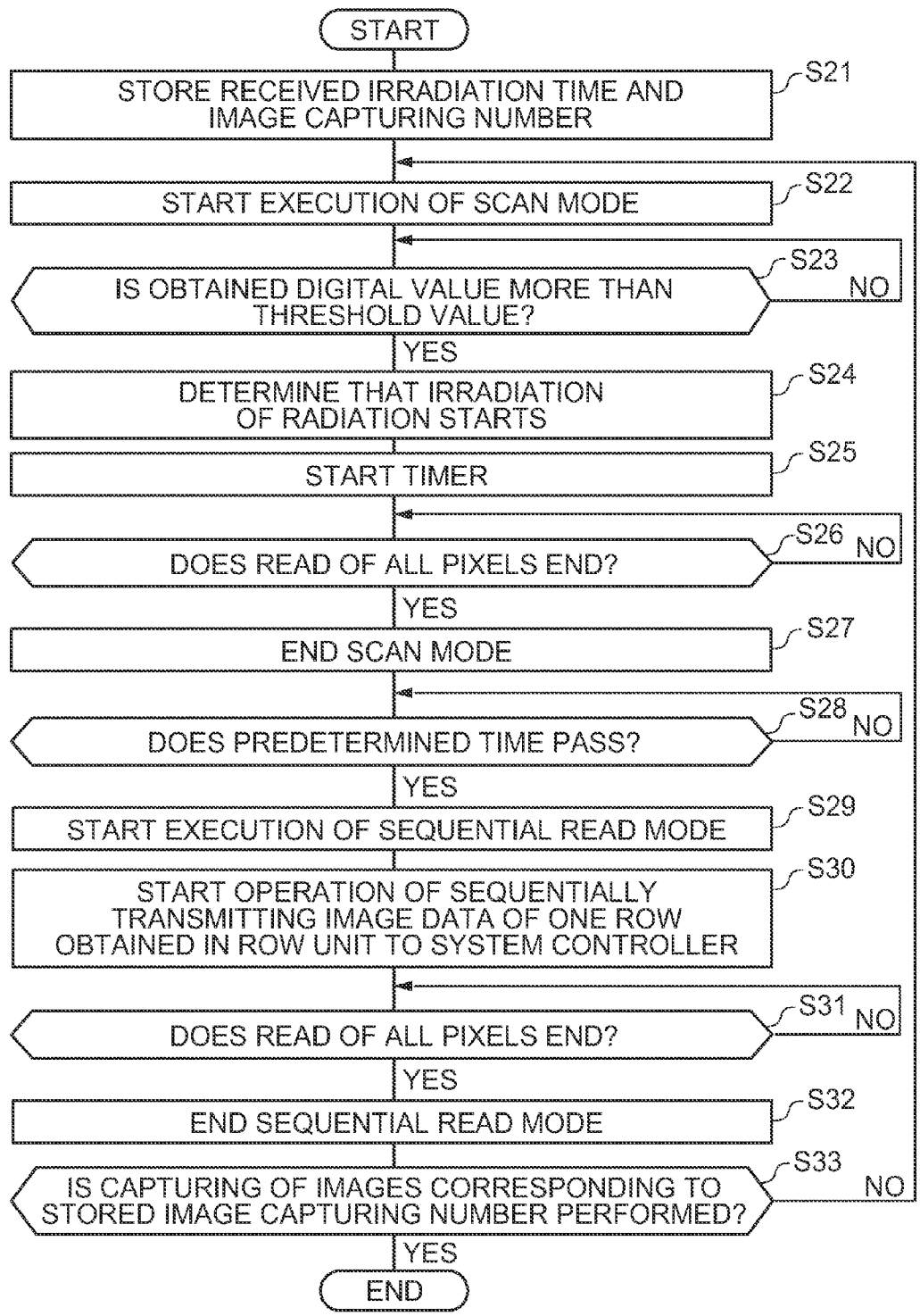
FIG. 13 is a flowchart illustrating an operation of the cassette control unit.

Next, an operation of the radiation image capturing system 10 will be described with reference to flowcharts of FIGS. 12 and 13. FIG. 12 is a flowchart illustrating operations of the system controller 24 and the console 26 of the radiation image capturing system 10 and FIG. 13 is a flowchart illustrating an operation of the cassette control unit 122. After the operations of the system controller 24 and the console 26 are first described, the operation of the cassette control unit 122 will be described.

The control unit 202 of the console 26 determines whether the image capturing part, the diagnosis part, and the image capturing number are selected by the operation of the input unit 200 from the user (step S1). At this time, the control unit 202 displays an image to allow the user to select the image capturing part, the diagnosis part, and the image capturing number, on the display unit 204. The user can select the image capturing part and the diagnosis part of the patient who becomes a radiation image capturing object, while viewing the displayed image.

In step S1, when it is determined that the image capturing part, the diagnosis part, and the image capturing number are not selected, the processing remains in step S1 until the image capturing part, the diagnosis part, and the image capturing number are selected.

Meanwhile, when it is determined that the image capturing part, the diagnosis part, and the image capturing number are selected by the user in step S1, the image capturing condition setting unit 222 reads the image capturing conditions according to the image capturing part and the diagnosis part selected by the user, from the table 218, and sets the read image capturing conditions as image capturing conditions of radiation image capturing to be executed in the future, and the image capturing number setting unit 224 sets the image capturing number that is selected by the user (step S2). Specifically, when the image capturing part is selected by the operation of the input unit 200 from the user, the control unit 202 outputs the selected image capturing part to the control unit 212 of the system controller 24 through the interfaces I/F 206 and 210. The image capturing condition setting unit 222 of the control unit 212 sets the image capturing conditions as the image capturing conditions corresponding to the image capturing part and the diagnosis part transmitted from the console 26 and sets the image capturing number as the image capturing number transmitted from the console 26. The system controller 24 may output the set image capturing conditions to the control unit 202 through the interfaces I/F 210 and 206 and the control unit 202 may display the set image capturing conditions and image capturing number on the display unit 204. Thereby, the user can view contents of the set image capturing conditions.

In order to irradiate the radiation 16 from the radiation source 34 under the set image capturing conditions, the user operates the input device that is provided in the radiation control device 36 and sets the same image capturing conditions as the image capturing conditions set at the side of the system controller 24 to the radiation control device 36. For example, the radiation device 18 may be configured to have the same table as the table 218, the user may select the image capturing part and the diagnosis part to set the same image capturing conditions, and the user may directly input the irradiation time, the tube voltage, and the tube current.

If the image capturing conditions are set, the control unit 212 transmits a start signal to the electronic cassette 20 through the communication unit 214 and starts the electronic cassette 20 (step S3). The electronic cassette 20 maintains a sleep state, until the start signal is transmitted. The sleep state means a state in which power is not supplied to the radiation conversion panel 64 and the driving circuit unit 106. If the electronic cassette 20 starts, the electronic cassette 20 executes the scan mode. After the start, the electronic cassette 20 may execute a reset operation before executing the scan mode.

Next, the image capturing condition setting unit 222 and the image capturing number setting unit 224 transmit the set irradiation time and image capturing number to the electronic cassette 20 through the communication unit 214 (step S4).

Next, the control unit 212 determines whether a read start signal is received from the electronic cassette 20 (step S5). The read start signal is a signal that indicates that read of the charge accumulated in the pixel 102 starts in the sequential read mode.

In step S5, when it is determined that the read start signal is not received, the processing remains in step S5 until the read start signal is received. When it is determined that the read start signal is received, the image recording control unit 226 determines whether image data of one row is transmitted (step S6). Since the electronic cassette 20 sequentially outputs the image data of one row sequentially read in a row unit to the system controller 24, the image data of one row is sequentially transmitted to the system controller 24.

In step S6, when it is determined that the image data of one row is transmitted, the image recording control unit 226 stores the transmitted image data of one row in a buffer memory (not illustrated in the drawings) of the control unit 212 (step S7).

Next, the image recording control unit 226 determines whether read of image data of one frame ends (step S8). In a case in which it is determined that the read of the image data of one frame ends, the electronic cassette 20 outputs a read end signal to the system controller 24. In a case in which the image recording control unit 226 receives the read end signal, the image recording control unit 226 determines that the read of the image data of one frame ends.

In step S8, in a case in which it is determined that the read of the image data of one frame does not end, the processing returns to step S6 and the above operation is repeated.

In step S8, when it is determined that the read of the image data of one frame ends, the image recording control unit 226 generates an image file from the image data of one frame stored in the buffer memory and records the image file in the recording unit 216 (step S9).

Next, the image recording control unit 226 determines whether image data corresponding to image capturing number set in step S2 is transmitted (step S10). In step S10, when it is determined that the image data corresponding to the set image capturing number is not transmitted, the processing returns to step S6. When it is determined that the image data corresponding to the set image capturing number is transmitted, the image recording control unit 226 ends the processing.

Next, an operation of the electronic cassette 20 will be described with reference to a flow chart illustrated in FIG. 13 and a time chart illustrated in FIG. 14. If a start signal is transmitted from the system controller 24, the electronic cassette 20 starts and the cassette control unit 122 stores the irradiation time and the image capturing number that are transmitted from the system controller 24, in the memory 124 (step S21).

Next, the first read control unit 130 of the cassette control unit 122 starts execution of the scan mode (step S22). If the execution of the scan mode starts, the first read control unit 130 outputs the driving signal c to each gate driving circuit 150. If each gate driving circuit 150 receives the driving signal c, each gate driving circuit 150 sequentially selects the gate lines 110 managed by each gate driving circuit from the zero-th row, outputs a gate signal to the selected gate line 110, and sequentially reads the charge accumulated in the pixels 102 of the region managed by each gate driving circuit, from the zero-th row in a row unit. Thereby, the charge that is accumulated in the pixels 102 of the region managed by each gate driving circuit 150 is simultaneously read in a row unit and the read charge is added for each column.

Specifically, the charge that is accumulated in the pixels 102 of the zero-th row of the region managed by each gate driving circuit 150 is simultaneously read, is added for each column, and is output to the charge amplifier 116 of each column. The charge that is accumulated in the pixels 102 of the first row of the region managed by each gate driving circuit 150 is simultaneously read, is added for each column, and is output to the charge amplifier 116 of each column. This operation is repeated up to the 239-th row.

The charge of one row that is sequentially read in a row unit and is added for each column is transmitted to the charge amplifier 116 and is stored as an electric signal of a digital signal in the memory 124 through the multiplexer unit 118 and the A/D conversion unit 120. Thereby, in the memory 124, the added image data of one row is sequentially stored. If each gate driving circuit 150 reads the charge accumulated in the pixels 102 of the 239-th row, each gate driving circuit 150 outputs an end signal d to the cassette control unit 122.

The first read control unit 130 controls a state of the switch 160 of each charge amplifier 116 to become an OFF state, while the scan mode is executed. Thereby, each charge amplifier 116 can output the input charge signal as a voltage signal. Before executing the scan mode after the start, the cassette control unit 122 may execute a reset operation. After a constant time (for example, 10 sec.) passes from the start, the first read control unit 130 may start the execution of the scan mode.

Next, the irradiation start determination unit 132 determines whether the value of the electric signal of the digital signal stored in the memory 124 is more than a threshold value (step S23). If the radiation 16 is irradiated from the radiation source 34 to the electronic cassette 20, the value of the electric signal of the digital signal that is stored in the memory 124 becomes more than the threshold value. That is, the irradiation start determination unit 132 detects whether the radiation 16 is irradiated according to whether the value of the electric signal of the digital signal is more than the threshold value. In step S23, when it is determined that the value of the electric signal of the digital signal is not more than the threshold value, the processing remains in step S23 until it is determined that the value of the electric signal is more than the threshold value. In a case in which the end signals d1 to d12 are transmitted from the individual gate driving circuits 150 to the cassette control unit 122 (charge of one frame is read), the first read control unit 130 outputs the driving signals c1 to c12 to the individual gate driving circuits 150 again. A period until the end signals d1 to d12 are output after the driving signals c1 to c12 are input to the individual gate driving circuits 150 is set as one cycle of the scan mode. The end signals d1 to d12 are transmitted from the individual gate driving circuits 150 at the same timing.

Meanwhile, in step S23, in a case in which it is determined that the value of the electric signal of the digital signal stored in the memory 124 is more than the threshold value, the irradiation start determination unit 132 determines that the irradiation of the radiation 16 by the radiation source 34 starts (step S24).

That is, if the user semi-presses the radiation switch 38 during the execution of the scan mode, the radiation control device 36 prepares for irradiation of radiation 16. Then, when the user completely presses the radiation switch 38, the radiation control device 36 irradiates the radiation 16 from the radiation source 34 for a predetermined time. As described above, since the radiation control device 36 irradiates the radiation 16 under the image capturing conditions corresponding to the image capturing part and the diagnosis part selected by the user, the predetermined time is an irradiation time according to the image capturing part and the diagnosis part selected by the user. In a case in which plural images are captured, the user operates the radiation switch 38 at a predetermined time interval and irradiates the radiation 16 from the radiation source 34.

In step S24, when it is determined that the irradiation of the radiation 16 starts, the cassette control unit 122 starts the timer (step S25), and the first read control unit 130 determines whether read of the charge accumulated in all of the pixels 102 ends (read of the charge of one frame ends), by the execution of the scan mode (step S26). That is, the first read control unit 130 determines whether one cycle of the scan mode ends, after it is determined that the irradiation of the radiation 16 starts. Specifically, the first read control unit 130 determines whether the end signals d1 to d12 are transmitted from the individual gate driving circuits 150, after the determination of the start of the irradiation of the radiation 16.

In step S26, in a case in which it is determined that the reading of the charge accumulated in all of the pixels 102 does not end, the processing remains in step S26 until it is determined that the reading of the charge ends. In a case in which it is determined that the reading of the charge accumulated in all of the pixels 102 ends, capturing of a radiation image is executed. That is, the first read control unit 130 exposures the radiation 16 and reads the charge accumulated in the pixels 102 by the exposure of the radiation 16. Specifically, the first read control unit 130 ends the execution of the scan mode to start exposure and transits the operation state to an exposure state (step S27). That is, even if the end signals d1 to d12 are transmitted, the first read control unit 130 does not output the driving signals c1 to c12 to the individual gate driving circuits 150. The first read control unit 130 turns on the switch 160 of the charge amplifier 116 when the scan mode ends. Thereby, the unnecessary charge that is accumulated in the capacitor 158 can be discharged and an image quality of a radiation image can be improved.

Figure 14:
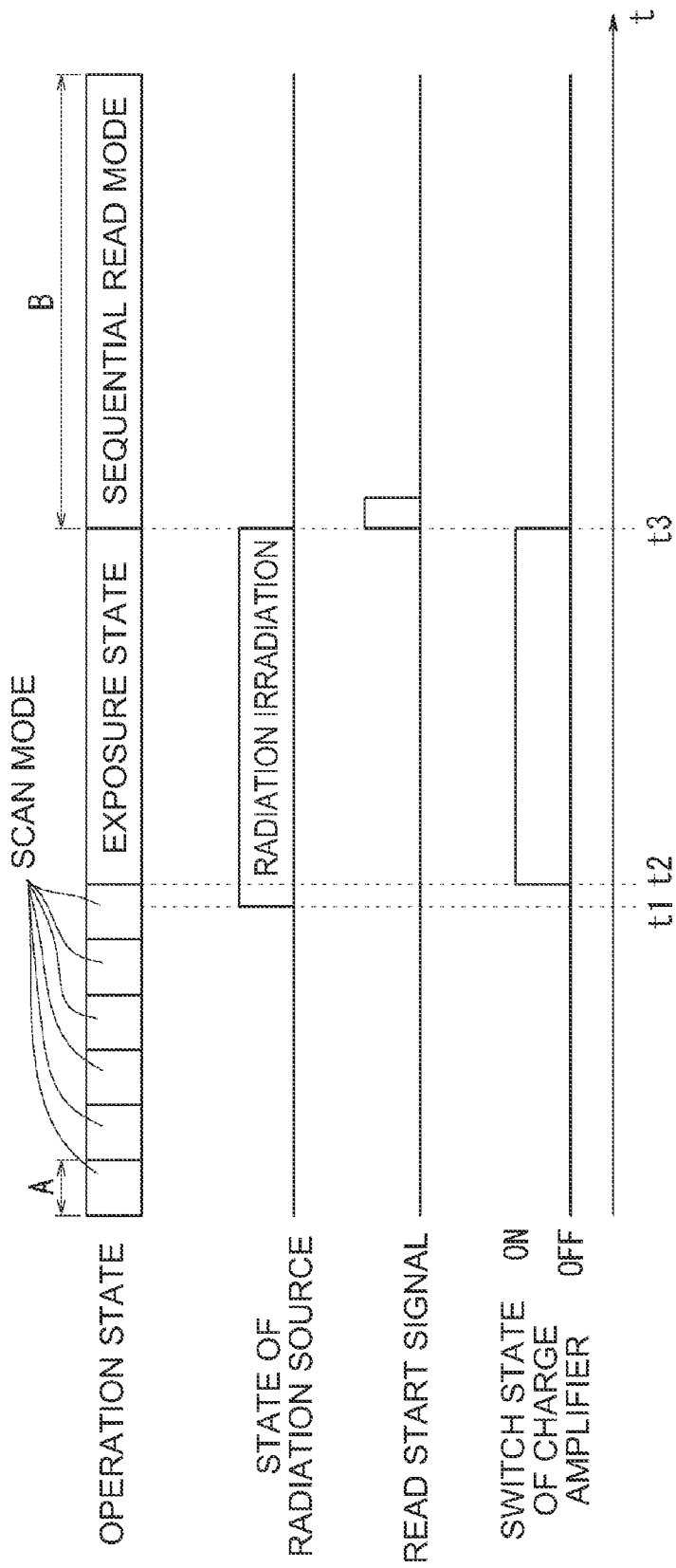
FIG. 14 is a time chart illustrating an operation of the electronic cassette.

As illustrated in FIG. 14, the scan mode is repetitively executed until it is determined that the irradiation of the radiation 16 by the radiation source 34 starts. A timing t1 indicates a timing when it is determined that the irradiation of the radiation 16 starts. An arrow A indicates one cycle of the scan mode and time thereof is about 5 msec. In a case in which it is determined that the irradiation of the radiation 16 starts, if the cycle of the currently executed scan mode ends, the execution of the scan mode ends and the operation state transits to the exposure state.

In step S27, if the execution of the scan mode ends, the passage time determination unit 134 determines whether predetermined time passes from the determination of the start of irradiation of the radiation 16 (step S28). In step S28, when it is determined that the predetermined time does not pass from the start of irradiation of the radiation 16, the processing remains in step S28 until the predetermined time passes. Since the predetermined time is irradiation time corresponding to the image capturing part and the diagnosis purpose selected by the user, the passage time determination unit 134 determines whether the irradiation of the radiation 16 ends, in step S28. Therefore, the exposure is executed to capture a radiation image, until the predetermined time passes from the end of the execution of the scan mode.

Meanwhile, in step S28, when it is determined that the predetermined time passes from the start of irradiation of the radiation 16, the exposure ends. In order to read the charge obtained by the exposure of the radiation 16, the second read control unit 136 starts the execution of the sequential read mode (step S29). At this time, the second read control unit 136 outputs the read start signal to the system controller 24 through the communication unit 126, before the start of the execution of the sequential read mode, at the time of the start, or after the start. Thereby, the system controller 24 can recognize that the image data of the radiation image is transmitted from the electronic cassette 20, and can prepare for receiving the image data.

If the sequential read mode is executed, the second read control unit 136 outputs the driving signal a1 to the first gate driving circuit 150. If the first gate driving circuit 150 receives the driving signal a1, the first gate driving circuit 150 sequentially selects the gate lines 110 managed by the first gate driving circuit from the zero-th row, outputs the gate signal to the selected gate line 110, and sequentially reads the charge accumulated in the pixels 102 of the region managed by the first gate driving circuit from the zero-th row, in a row unit. Thereby, the charge that is accumulated in the pixels 102 of the region managed by the first gate driving circuit 150 is sequentially read from the zero-th row to the 239-th row, in a row unit. If the first gate driving circuit 150 selects the 239-th row, the first gate driving circuit 150 outputs the end signal b1 to the cassette control unit 122.

If the second read control unit 136 receives the end signal b1, the second read control unit 136 outputs the driving signal a2 to the second gate driving circuit 150. This operation is executed up to the twelfth gate driving circuit 150. Thereby, the charge that is accumulated in the pixels 102 of the zero-th to 2879-th rows of the radiation conversion panel 64 is sequentially read in a row unit. The charge that is sequentially read in a row unit is input to the charge amplifier 116 of each column. Then, the charge is stored as an electric signal of a digital signal in the memory 124 through the multiplexer unit 118 and the A/D conversion unit 120. That is, in the memory 124, image data of one row that is obtained in a row unit is sequentially stored.

Timing t3 illustrated in FIG. 14 indicates timing when it is determined that the predetermined time passes in step S28, and the execution of the sequential read mode starts almost at the same time as the timing t3 or immediately after the timing t3. At the same time as the time when the sequential read mode starts, a read start signal is output from the second read control unit 136 to the system controller 24. An arrow B indicates one cycle of the sequential read mode and time thereof is about 500 msec. That is, a period until the twelfth gate driving circuit 150 outputs the end signal b12 after the driving signal a1 is input to the first gate driving circuit 150 is set as one cycle of the sequential read mode.

The cassette control unit 122 controls a state of the switch 160 of each charge amplifier 116 to become an OFF state, during the execution of the sequential read mode. Thereby, each charge amplifier 116 can output the input charge signal as a voltage signal.

If the execution of the sequential read mode starts, the cassette control unit 122 starts an operation of sequentially transmitting image data of one row obtained in a row unit to the system controller 24 (step S30). That is, if the image data of one row is stored in the memory 124, the cassette control unit 122 transmits the stored image data to the system controller 24 through the communication unit 126.

Next, the second read control unit 136 determines whether read of the charge accumulated in all of the pixels 102 ends (read of the charge of one frame ends), by the execution of the sequential read mode (step S31). That is, the second read control unit 136 determines whether one cycle of the sequential read mode ends. Specifically, the second read control unit 136 determines whether the end signal b12 is transmitted form the twelfth gate driving circuit 150.

In step S31, in a case in which it is determined that the read of the charge accumulated in all of the pixels 102 does not end, the processing remains in step S31, until it is determined that the read of the charge ends. In a case in which it is determined that the read of the charge accumulated in all of the pixels 102 ends, the second read control unit 136 ends the execution of the sequential read mode (step S32). At this time, the second read control unit 136 outputs the read end signal to the system controller 24 through the communication unit 126.

Next, the cassette control unit 122 determines whether capturing of images of the image capturing number stored in step S21 (image capturing number set by the user) is performed (whether exposure corresponding to the image capturing number and sequential read are executed) (step S33). In step S33, when it is determined that the images of the stored image capturing number are not captured, the processing returns to step S22 and the above operation is repeated. When it is determined that the images of the stored image capturing number are captured, the processing ends.

Figure 15:
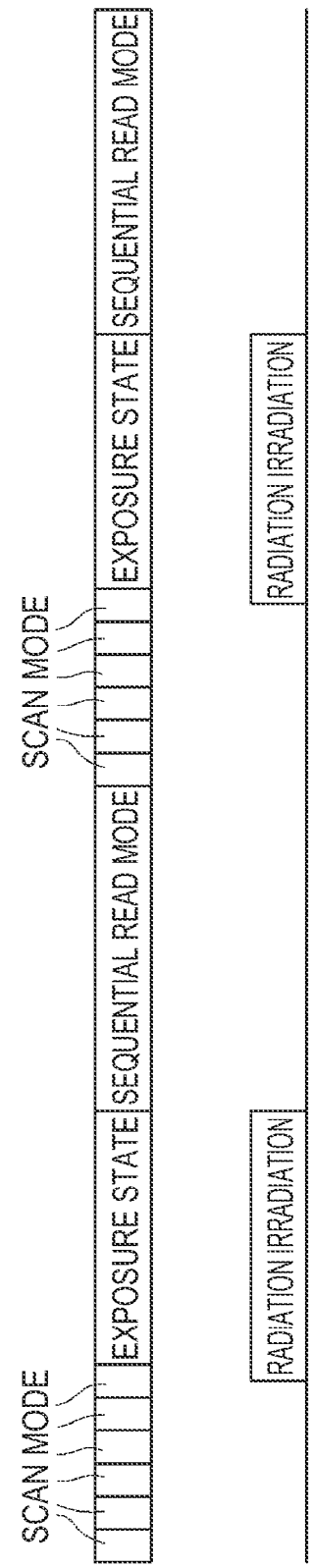
FIG. 15 is a time chart illustrating an operation of the electronic cassette in a case in which the image capturing number is set to 2.

FIG. 15 is a time chart illustrating an operation of the electronic cassette 20 in a case in which the image capturing number is set to 2. The first read control unit 130 of the electronic cassette 20 repetitively executes the scan mode, until the first irradiation of the radiation 16 is executed. The irradiation of the radiation 16 by the radiation source 34 starts, and it is determined by the irradiation start determination unit 132 that the irradiation of the radiation 16 starts. If one cycle of the currently executed scan mode ends, the operation state transits to the exposure state. Then, if the predetermined time passes (irradiation of the radiation 16 ends), the second read control unit 136 executes the sequential read mode and reads the charge that is accumulated in the pixels 102 by the irradiation of the radiation 16. Then, the first read control unit 130 repetitively executes the scan mode again. It is determined by the irradiation start determination unit 132 that the irradiation of the radiation 16 starts. If one cycle of the currently executed scan mode ends, the operation state transits to the exposure state. Then, if the predetermined time passes (irradiation of the radiation 16 ends), the second read control unit 136 reads the charge that is accumulated in the pixels 102 and ends the processing. At this time, the user can operate the radiation switch 38 two times at the predetermined time interval and irradiate the radiation 16 onto the subject 14 two times.

As such, before the radiation 16 is irradiated, the charge that is accumulated in the pixels 102 is read in the scan mode in which the charge can be read at the speed higher than the speed in the sequential read mode. When the digital value obtained by reading the charge is more than the threshold value, it is determined that the irradiation of the radiation 16 starts and the exposure starts. Therefore, synchronization of image capturing timing (synchronization of irradiation timing of the radiation 16 and exposure timing of the electronic cassette 20) does not need to be carried out, and a radiation image that has a high image quality can be captured.

In the scan mode, since the charge accumulated in the pixels 102 is simultaneously read in a unit of plural rows, the start of irradiation of the radiation 16 can be determined early and accurately. That is, since the charge accumulated in the pixels 102 is added and read, the obtained digital value greatly increases, and the start of irradiation of the radiation 16 can be determined early, in a case in which the radiation 16 is irradiated, as compared with in a case in which the radiation 16 is not irradiated. In contrast, if the threshold value is decreased without adding the charge, the start of irradiation of the radiation 16 can be detected early by the decrease. However, a ratio of the noise with respect to the threshold value increases, and the start of irradiation of the radiation 16 cannot be detected accurately.

In the scan mode, since the charge is read in a unit of plural rows, the read speed of an image of one frame can be increased (one cycle of the scan mode can be shortened). Even when it is determined that the irradiation of the radiation 16 starts, time that is needed to transit to the exposure state can be decreased.

In the scan mode, since each gate driving circuit 150 simultaneously reads the charge accumulated in the pixels 102 of the region managed by each gate driving circuit sequentially from the zero-th row in a row unit, it can be detected early that the irradiation of the radiation 16 starts, even though the radiation 16 is irradiated onto a certain region of the radiation conversion panel 64. In a case in which the charge accumulated in the pixels 102 is read in the sequential read mode to detect the start of irradiation of the radiation 16 and the radiation 16 is irradiated onto the region from the 2000-th row to the 2879-th row, the irradiation of the radiation 16 cannot be detected during a read period of the charge that is accumulated in the pixels 102 of the zero-th to 1999-th rows. However, since each gate driving circuit 150 reads the charge accumulated in the pixels 102 in a row unit from the zero-th to 239-th rows, that is, the charge accumulated in the pixels 102 is simultaneously read at an interval of 240 rows, an irradiation region of the radiation 16 can be quickly detected, even though the radiation 16 is irradiated onto the certain region.

The electronic cassette 20 executes the scan mode until it is determined that the irradiation of the radiation 16 starts. When it is determined that the irradiation of the radiation 16 starts, the operation state transits to the exposure state. Therefore, synchronization of the image capturing timing does not need to be carried out, the radiation device 18 and the system controller 24 are not electrically connected, and a cost is decreased. Since the scan mode is executed until it is determined that the irradiation of the radiation 16 starts, the unnecessary charge accumulated in the pixels 102 can be removed and the noise of the radiation image can be decreased.

When it is determined that the irradiation of the radiation 16 starts, the scan mode ends and the operation state transits to the exposure state, and thus the radiation 16 having image information is not wasted. If the irradiation time (predetermined time) passes after the irradiation of the radiation 16 starts, the sequential read mode is executed. Therefore, an exposure period of the pixels can be minimized and the noise of the radiation image can be further decreased. A sensor for radiation detection does not need to be separately provided and a manufacturing cost is decreased.

The above exemplary embodiment can be modified as follows.

(First Modification)

In the exemplary embodiment described above, in a case in which it is determined that the radiation 16 is irradiated during the execution of the scan mode, the state does not transit to the exposure state, until one cycle ends. However, in a case in which it is determined that the radiation 16 is irradiated during the execution of the scan mode, the state may immediately transit to the exposure state.

Figure 16:
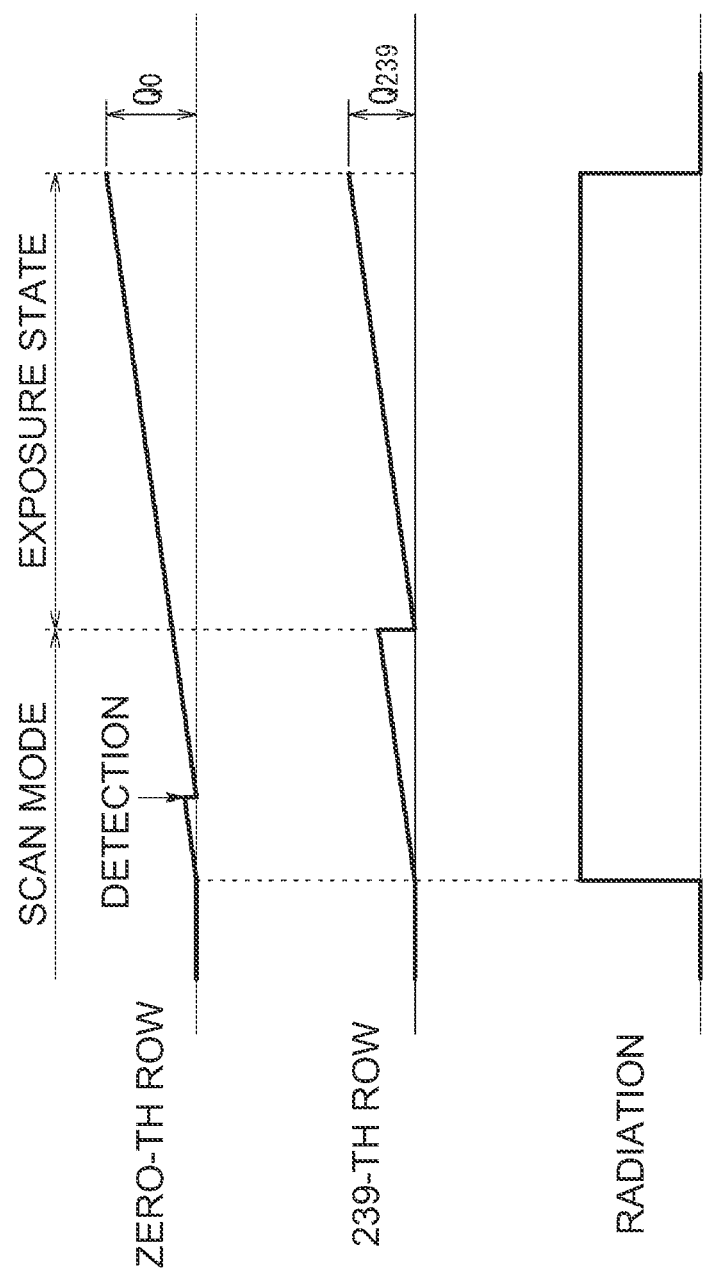
FIG. 16 is a diagram illustrating an aspect of charge accumulated in pixels of each row in a case in which an operation state transits to an accumulation state after one cycle of the scan mode ends, in a case where radiation is detected in a case in which charge accumulated in pixels of a zero-th row is read.
Figure 17:
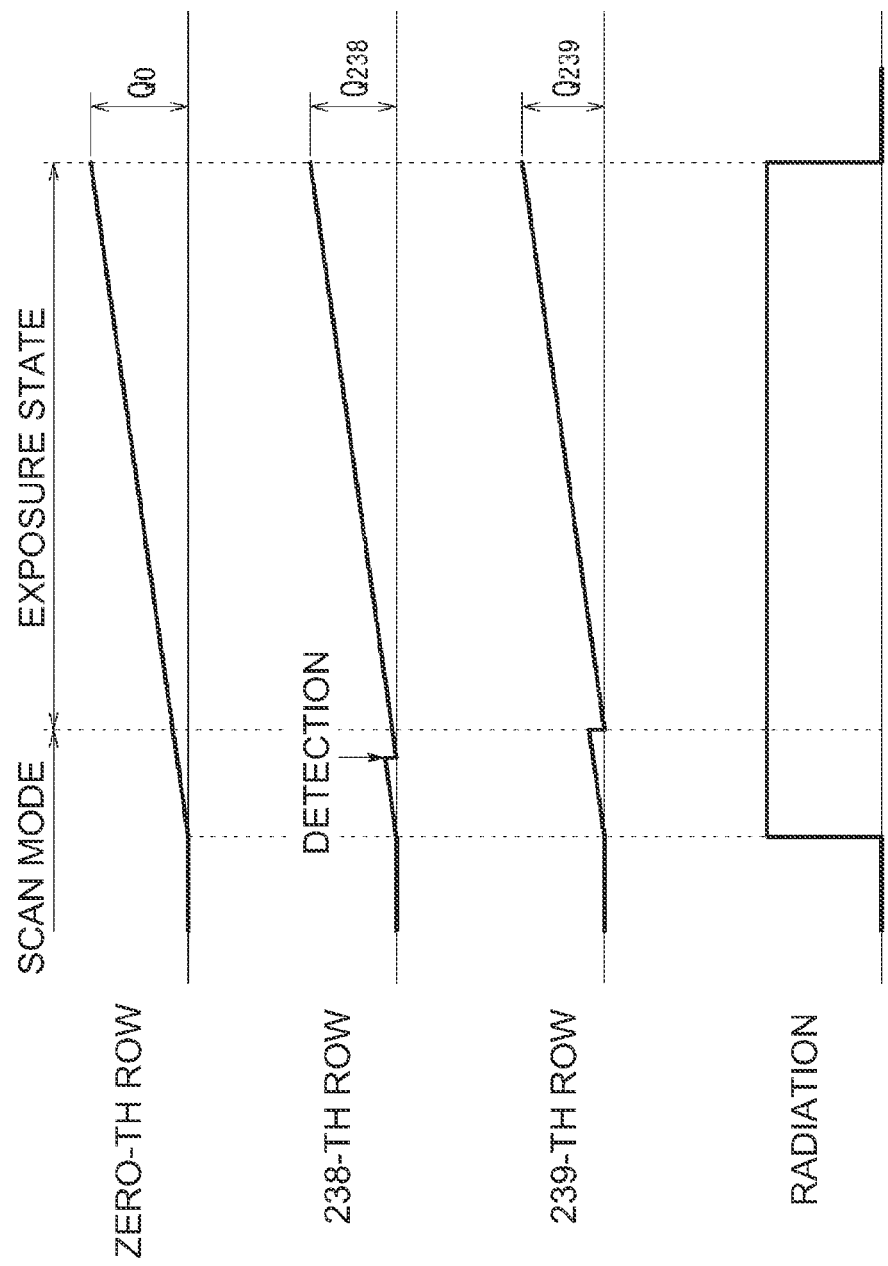
FIG. 17 is a diagram illustrating an aspect of charge accumulated in pixels of each row in a case in which an operation state transits to an accumulation state after one cycle of the scan mode ends, in a case where radiation is detected in a case in which charge accumulated in pixels of a 238-th row is read.

FIGS. 16 and 17 are diagrams illustrating an aspect of charge accumulated in the pixels 102 of each row in a case in which the radiation 16 is detected and the operation state transits to an accumulation state after one cycle of the scan mode ends. During the execution of the scan mode, each gate driving circuit 150 sequentially reads the charge accumulated in the pixels 102 from the zero-th row, in a row unit. In this case, for example, even if it is determined that a digital value obtained by reading the charge accumulated in the pixels 102 of the zero-th row is more than the threshold value and the radiation 16 is detected, the scan mode cannot transit to the exposure state, until the charge accumulated in the pixels 102 of the 239-th row is read.

Therefore, by executing the scan mode after the radiation 16 is detected, the charge that is accumulated in the pixels 102 by the irradiation of the radiation 16 is read (abandoned), and the radiation 16 that has image information is wasted. In a case in which the radiation 16 is detected at a stage before one cycle in the scan mode, the radiation is further wasted. That is, if a timing when it is detected that the radiation 16 is irradiated is close to a timing when the charge accumulated in the pixels 102 of the 239-th row is read, the radiation 16 is not wasted.

Specifically, as illustrated in FIG. 16, in a case in which the radiation 16 is detected by the read of the charge of the pixels 102 of the zero-th row, the charge that is accumulated in the pixels 102 of the first to 239-th rows is sequentially read in a row unit by the execution of the scan mode, and thus the charge that is accumulated in the pixels 102 of the first to 239-th rows by the irradiation of the radiation 16 may be abandoned. For this reason, the charge that is accumulated by the irradiation of the radiation 16 may be wasted. A relationship of the amount of charge Q0 accumulated in the pixels 102 of the zero-th row that is obtained by the exposure to capture the radiation image and the amount of charge Q239 accumulated in the pixels 102 of the 239-th row becomes Q0>Q239, the difference thereof is large, and the variation of the amount of charge that is accumulated in the pixels 102 of each row is large.

Meanwhile, as illustrated in FIG. 17, in a case in which the radiation 16 is detected by the read of the charge of the pixels 102 of the 238-th row, the charge that is accumulated in the pixels 102 of the 239-th row is only read, and thus only the charge that is accumulated in the pixels 102 of the 239-th row by the irradiation of the radiation 16 may be abandoned. In this case, a relationship of the amount of charge Q0 accumulated in the pixels 102 of the zero-th row that is obtained by the exposure to capture the radiation image, the amount of charge Q238 accumulated in the pixels 102 of the 238-th row, and the amount of charge Q239 accumulated in the pixels 102 of the 239-th row becomes Q0>Q238>Q239, the difference thereof is small, and the variation of the amount of charge that is accumulated in the pixels 102 of each row is small.

As such, the amount of charge accumulated in the pixels 102 of each row that is obtained by the exposure to capture the radiation image depends on timing when the radiation 16 is irradiated and the variation may be generated.

Therefore, in the first modification, if the irradiation of the radiation 16 is detected, the operation state transits to the accumulation state without reading the charge accumulated in the pixels 102, after the radiation 16 is detected. Specifically, if the cassette control unit 122 detects the start of irradiation of the radiation 16, the cassette control unit 122 transmits a stop signal to stop the read to each gate driving circuit 150. If the driving signals c1 to c12 are transmitted, each gate driving circuit 150 sequentially selects the gate lines 110, outputs the gate signal to the selected gate line 110, and sequentially reads the charge accumulated in the pixels 102 in a row unit. If the stop signal is transmitted, a mask processing is executed and the gate signal is not output from the gate driving circuit 150. That is, the first read control unit 130 prohibits read of the charge accumulated in the pixels 102 by the execution of the scan mode. In this case, if the stop signal is transmitted, each gate driving circuit 150 continuously executes the operation of sequentially selecting the gate lines 110 (scan mode is continuously executed). However, since the mask processing is executed, the gate signal is not output to the selected gate line 110. Thereby, the state can transit to the exposure state, after the radiation 16 is detected.

For example, in a case in which the stop signal is transmitted after the gate signal is output to the gate line 110 of the zero-th row, each gate driving circuit 150 sequentially selects the gate lines 110 of each row like the first row and the second row, even after the stop signal is transmitted. However, the gate signal is not output to the selected gate line 110. In this case, even in a case in which the stop signal is transmitted, each gate driving circuit 150 sequentially selects the gate lines 110. Therefore, each gate driving circuit 150 outputs each of the end signals d1 to d12, after the gate line 110 of the 239-th row is selected. The first read control unit 130 ends the scan mode, when the end signals d1 to d12 are transmitted from the individual gate driving circuits 150.

Figure 18:
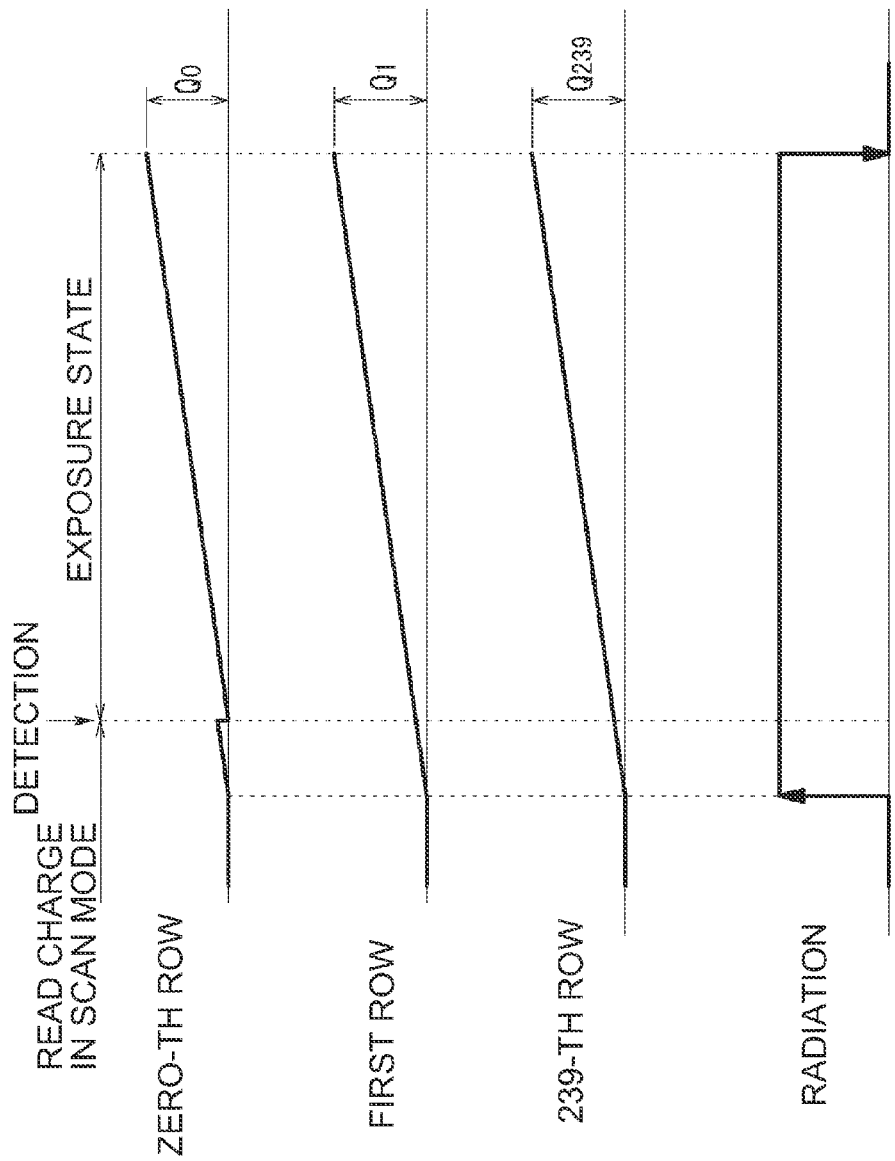
FIG. 18 is a diagram illustrating an aspect of charge accumulated in pixels of each row in a case in which an operation state transits to an accumulation state by immediately ending read of charge accumulated in pixels in a scan mode at the time of detecting radiation.

FIG. 18 is a diagram illustrating an aspect of charge accumulated in the pixels 102 of each row in a case in which an operation state transits to an accumulation state by immediately ending reading of charge accumulated in the pixels 102 in the scan mode at the time of detecting the radiation 16.

In FIG. 18, the aspect of charge that is accumulated in the pixels 102 of each row in a case in which the radiation 16 is detected by reading the charge accumulated in the pixels 102 of the zero-th row is illustrated. When the cassette control unit 122 detects the radiation 16, the cassette control unit 122 transmits the stop signal to each gate driving circuit 150. Therefore, the charge that is accumulated in the pixels 102 of the second and following rows is not read and the charge is accumulated by the irradiation of the radiation 16. In this case, a relationship of the amount of charge Q0 accumulated in the pixels 102 of the zero-th row that is obtained by the exposure to capture the radiation image, the amount of charge Q1 accumulated in the pixels 102 of the first row, and the amount of charge Q239 accumulated in the pixels 102 of the 239-th row satisfies the relationships of Q0<Q1=Q239, and the difference of the charge amounts of Q0 and Q1 and Q239 is small. Therefore, the exposure can be executed without wasting the radiation 16 having the image information, and the variation can be decreased.

The operation of the cassette control unit 122 according to the first modification is almost the same as the operation according to the flowchart illustrated in FIG. 13. In step S24 of FIG. 13, in a case in which it is determined by the irradiation start determination unit 132 that the irradiation of the radiation 16 starts, the first read control unit 130 transmits a stop signal to each gate driving circuit 150 and proceeds to an operation of step S25. Thereby, the operation state can be transited to the exposure state. In step S26, the first read control unit 130 determines whether the end signals d1 to d12 are transmitted from the individual gate driving circuits 150. If it is determined that the end signals d1 to d12 are transmitted, the execution of the scan mode ends in step S27.

As such, if it is determined that the irradiation of the radiation 16 starts, the electronic cassette 20 outputs the stop signal to each gate driving circuit 150, and the scan mode is continuously executed until one cycle ends. However, since the charge accumulated in the pixels 102 is not read, an image of the radiation 16 can be captured without wasting the radiation 16 having the image information.

(Second Modification)

In the exemplary embodiment and the first modification, the image capturing number setting unit 224 of the system controller 24 sets the image capturing number that is input by the operation of the input unit 200 from the user, and transmits the image capturing number to the electronic cassette 20. However, the image capturing number according to the image capturing part and the diagnosis purpose may be recorded in the table 218. In this case, the image capturing condition setting unit 222 reads the image capturing number according to the image capturing part and the diagnosis purpose selected by the user from the table 218, sets the image capturing number, and transmits the set image capturing number to the electronic cassette 20.

(Third Modification)

In the exemplary embodiment and the first and second modifications, in a case in which the radiation image capturing is executed many times, the radiation source 34 irradiates the radiation 16 many times, by the operation of the radiation switch 38 from the user. In a case in which the radiation image capturing is executed many times, the radiation source 34 may irradiate the radiation 16 continuously for a constant time, and the electronic cassette 20 may execute the radiation image capturing many times, for the constant time. The constant time can be set by operating the input device of the radiation control device 36 by the user, and the radiation control device 36 controls the radiation source 34 to irradiate the radiation 16 for the set constant time.

Figure 19:
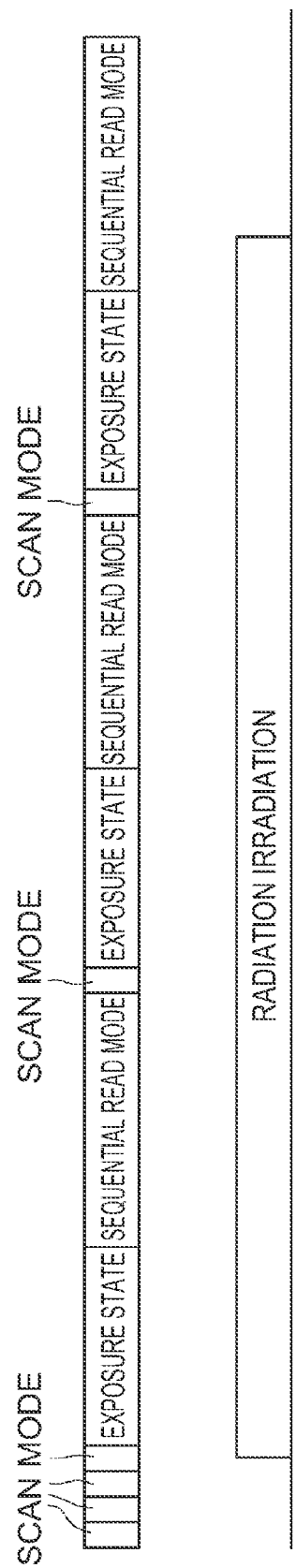
FIG. 19 is a time chart illustrating an operation of an electronic cassette in a third modification.

FIG. 19 is a time chart illustrating an operation of the electronic cassette 20 according to the third modification. The first read control unit 130 of the electronic cassette 20 repetitively executes the scan mode, until the radiation 16 is irradiated. If the irradiation of the radiation 16 by the radiation source 34 starts, the irradiation start determination unit 132 determines that the irradiation of the radiation 16 starts and transits to the exposure state. Then, if the predetermined time passes, the second read control unit 136 executes the sequential read mode and reads the charge accumulated in the pixels 102 by the irradiation of the radiation 16. Then, the first read control unit 130 executes the scan mode again. However, since the radiation 16 is continuously irradiated, the irradiation start determination unit 132 immediately determines that the irradiation of the radiation 16 starts and transits to the exposure state. Then, if the predetermined time passes, the second read control unit 136 executes the sequential read mode and reads the charge accumulated in the pixels 102 by the irradiation of the radiation 16. As such, the radiation image capturing may be executed many times during the irradiation of the radiation 16. The predetermined time may be an irradiation time that corresponds to the image capturing part and the diagnosis object selected by the user, a default value, or an irradiation time that is set individually by the user.

(Fourth Modification)

In the exemplary embodiment and the first to third modifications, in the scan mode, the operation of simultaneously reading the charge in a unit of plural rows is sequentially executed, and the charge that is accumulated in all of the pixels 102 is read. However, only the pixels of the predetermined row may be read. Hereinafter, the fourth modification will be described in detail.

Figure 20:
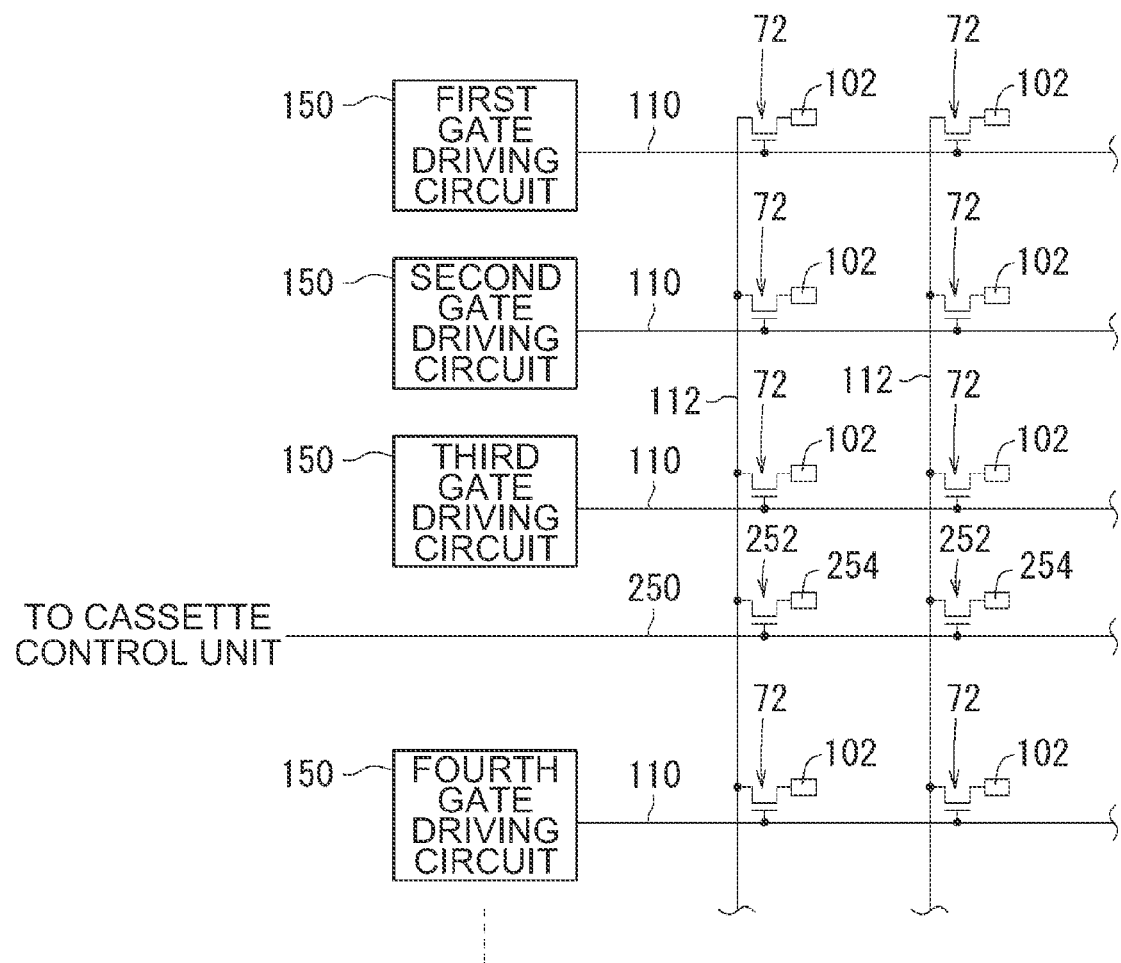
FIG. 20 is a diagram illustrating the detailed configuration of a part of a radiation conversion panel according to a fourth modification.

FIG. 20 is a diagram illustrating the detailed configuration of a part of the radiation conversion panel 64 according to the fourth modification. The radiation conversion panel 64 has gate lines 250, and the gate lines 250 are connected directly to the cassette control unit 122. The gate line 250 is connected to the pixel 254 through the TFT 252, and when the TFT 252 is turned on, the charge accumulated in the pixels 254 is read from the signal line 112. The gate line 250 supplies the gate signal to read the charge accumulated in the pixels 254 in the scan mode to the TFT 252. That is, the gate line 250, the TFT 252, and the pixel 254 are provided for the scan mode, separately from the gate line 110, the TFT 72, and the pixel 102. One gate line 250 may be provided in the radiation conversion panel 64 or one gate line may be provided between the gate driving circuits 150. The plural gate lines 250 may be provided at an equivalent interval over an entire region of the radiation conversion panel 64. For example, the gate lines 250 may be provided between the first gate driving circuit 150 and the second gate driving circuit 150, between the sixth gate driving circuit 150 and the seventh gate driving circuit 150, and the eleventh gate driving circuit 150 and the twelfth gate driving circuit 150, and the certain pixel 254 can receive the radiation 16, even in a case in which the radiation 16 is irradiated onto the certain region. The pixels 254 that are connected to the gate line 250 become the pixels of the predetermined row.

Although not illustrated in the drawings, the 240 gate lines 110 are connected to each gate driving circuit 150 and the pixels 102 are connected to each gate line 110 through the TFT 72.

In the scan mode according to the fourth modification, the first read control unit 130 outputs the gate signal directly to the gate line 250 and repetitively reads the charge accumulated in the pixels 254 in a row unit. For example, in a case in which only one gate line 250 exists, if the gate signal is output to the gate line 250, one cycle of the scan mode ends, the gate signal is output to the gate line 250 again at a next cycle, and the charge accumulated in the pixels 254 is repetitively read.

If the plural gate lines 250 exist, the first read control unit 130 repeats the operation of sequentially outputting the gate signal directly to the gate line 250 and sequentially reading the charge accumulated in the pixels 254 in a row unit. For example, in a case in which the three gate lines 250 exist, the first read control unit 130 outputs the gate signal to the gate line 250 of the zero-th row and reads the charge accumulated in the pixels 254 connected to the gate line 250 of the zero-th row. Next, the first read control unit 130 outputs the gate signal to the gate line 250 of the first row and reads the charge accumulated in the pixels 254 connected to the gate line 250 of the first row. Finally, the first read control unit 130 outputs the gate signal to the gate line 250 of the second row and reads the charge accumulated in the pixels 254 connected to the gate line 250 of the second row. If the gate signal is output to the gate line 250 of the second row, one cycle of the scan mode ends and the gate signal is output to the gate line 250 of the zero-th row at a next cycle.

In a case in which it is determined by the irradiation start determination unit 132 that the irradiation of the radiation 16 starts, the execution of the scan mode immediately ends and the operation state transits to the exposure state. After it is determined by the irradiation start determination unit 132 that the irradiation of the radiation 16 starts, the gate driving circuit 150 does not output the gate signal to the gate line 250. For example, in a case in which the three gate lines 250 exist and it is determined that the digital value obtained by outputting the gate signal to the gate line 250 of the zero-th row is more than the threshold value, the gate driving circuit 150 immediately ends the execution of the scan mode without outputting the gate signal to the gate lines 250 of the first and second rows. Thereby, power consumption by the scan mode can be suppressed.

If the predetermined time passes (irradiation of the radiation 16 ends) after the radiation 16 is detected (it is determined that the irradiation of the radiation 16 starts), the second read control unit 136 executes the sequential read mode.

That is, the electronic cassette 20 includes at least the plural pixels (first pixels) 102 that are arranged in a matrix, the plural TFTs (first switching elements) 72 that are arranged in a matrix to read the electric signals accumulated in the plural pixels 102, the plural gate lines (first gate lines) 110 that are connected to the TFTs 72 and are arranged in parallel to the row direction, the plural gate driving circuits 150 that are connected to the plural gate lines 110, output the gate signals to the TFTs 72 of each row through the gate lines 110, and are arranged along a column direction, and the plural signal lines 112 that are arranged in parallel to the column direction to read the electric signals accumulated in the plural pixels 102.

The electronic cassette 20 includes the plural pixels (second pixels) 254 that are arranged along a row direction in a plane in which the plural pixels 102 are arranged, the plural TFTs (second switching elements) 252 that are arranged along the row direction to read the electric signals accumulated in the pixels 102, and at least one gate line 250 that is connected to the TFTs 252 and is arranged in the row direction.

Gates of the TFTs 72 and 252 are connected to the gate lines 110 and 250 and sources thereof are connected to the pixels 102 and 254. Drains of the TFTs 72 and 252 are connected to the signal lines 112. If the driving signal a is input to each gate driving circuit 150, each gate driving circuit 150 sequentially selects the gate lines 110 connected to each gate driving circuit, outputs a gate signal to the selected gate line 110, turns on the TFT 72, and sequentially reads the electric signal accumulated in the pixels 102 connected to each gate driving circuit through the plural signal lines 112, in a row unit.

The first read control unit 130 executes the scan mode in which the gate signals are sequentially input to the gate lines 250 and the electric signals accumulated in the pixels 254 are sequentially read in a unit of one row. The second read control unit 136 executes the sequential read mode in which the driving signal a is sequentially input to each gate driving circuit 150 to sequentially drive each gate driving circuit 150 and the electric signals of the plural pixels 102 are sequentially read in a unit of one row.

The operation of the cassette control unit 122 in the fourth modification is almost the same as the operation according to the flowchart illustrated in FIG. 13. In step S24 of FIG. 13, in a case in which it is determined by the irradiation start determination unit 132 that the irradiation of the radiation 16 starts, the first read control unit 130 immediately stops an output of the gate signal to the gate line 250 (ends the execution of the scan mode) and proceeds to an operation of step S25. In step S25, if the timer starts, the processing proceeds to step S28 without executing the operations of steps S26 and S27.

In the fourth modification, since the charge is not read from the pixels 102 during the execution of the scan mode, the operation state transits to the exposure state during the execution of the scan mode. Therefore, the charge according to the irradiated radiation 16 can be accumulated without wasting the radiation 16 having the image information. Since the charge accumulated in the pixels 254 is read and the start of irradiation of the radiation 16 is determined, timing when the irradiation of the radiation 16 starts can be known. If the irradiation time passes from the timing when the irradiation of the radiation 16 starts, the mode transits to the sequential read mode. Therefore, the noise of the radiation image can be decreased without executing the unnecessary exposure after the irradiation of the radiation 16 ends. Since the start of irradiation of the radiation 16 is determined by reading the charge accumulated in the pixels 254, power consumption by the scan mode can be suppressed.

Similar to the sequential scan mode, in the scan mode in the fourth modification, the charge accumulated in the pixels 102 of one row may be read in time of 173 μsec. As such, since the charge accumulated in the pixels 102 may be read in time of 173 μsec, determination precision of the start of irradiation of the radiation 16 is not lowered, even though the charge accumulated in the pixels 102 is not added. Since the number of gate lines 250 for the scan mode is smaller than the number of gate lines 110 for radiation image capturing, time of one cycle of the scan mode can be decreased, even though the charge accumulated in the pixels 102 of one row is read in the same time as that of the sequential read mode. For example, if the number of gate lines 250 is 29, the time of one cycle of the scan mode becomes about 5 msec and becomes the same time as one cycle of the scan mode according to the exemplary embodiment.

In a case in which the plural gate lines 250 are provided, the user operates the input unit 200 of the console 26 and may select one or more gate lines 250 used during the execution of the scan mode, from the plural gate lines 250. Since the user can previously recognize a region of the electronic cassette 20 where the radiation 16 is irradiated by the radiation source 34, the user can select the gate line 250 that corresponds to the irradiation region of the radiation 16. Information that indicates the selected gate line 250 is transmitted from the console 26 to the electronic cassette 20 through the system controller 24. In a case in which the scan mode is executed, the first read control unit 130 outputs the gate signal to only the selected gate line 250.

Thereby, the irradiation start determination unit 132 can determine the start of irradiation of the radiation 16 early and surely. Since the gate signal is not output to the gate line 250 of the region where the radiation 16 is not irradiated, power consumption by the execution of the scan mode can be further suppressed.

If the plural gate lines 250 are provided, the large number of gate lines 250 of the region where the possibility of the radiation 16 being irradiated is high or of the region where the radiation is irradiated may be selected, and the small number of gate lines 250 of the region where the possibility of the radiation 16 being irradiated is low or of the region where the radiation is not irradiated may be selected. In a case in which the scan mode is executed, the gate signal is output to only the selected gate lines 250. The region where the possibility of the radiation 16 being irradiated is high or the region where the radiation is irradiated may be designated by operating the input unit 200 of the console 26 by the user. In this case, the region where the possibility of the radiation 16 being irradiated is high or the region where the radiation is irradiated may be designated directly by the user or the control unit 212 of the system controller 24 may read the region according to the image capturing part and the diagnosis purpose selected by the user, from the table 218, and designate the region. The control unit 212 of the system controller 24 selects the gate lines 110 used in the execution of the scan mode, on the basis of the designated region, and transmits information indicating the selected gate line 110 to the electronic cassette 20.

(Fifth Modification)

In the fourth modification, the gate line 250, the TFT 252, and the pixel 254 for the scan mode are provided separately from the gate line 110, the TFT 72, and the pixel 102. However, the predetermined gate line 110, TFT 72, and pixel 102 may be used for the scan mode.

Figure 21:
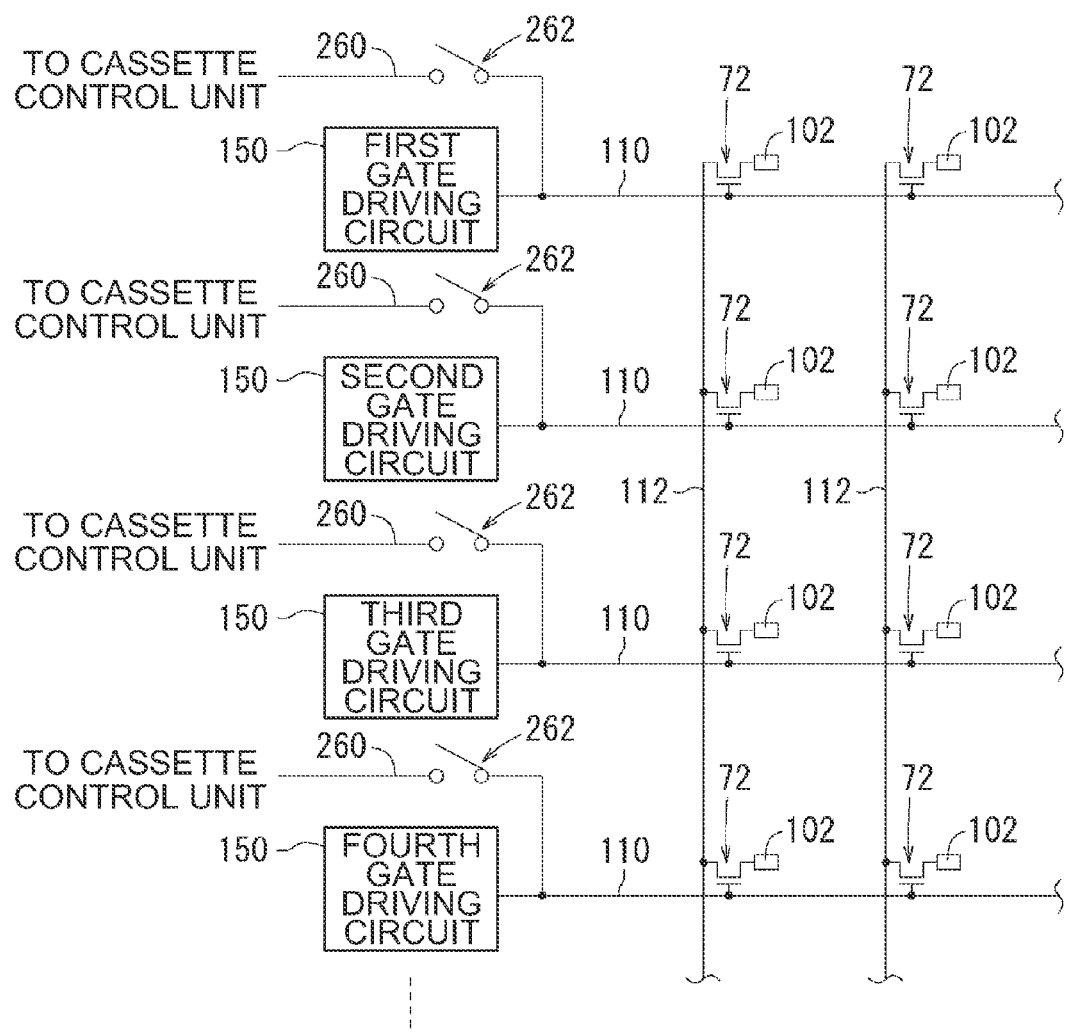
FIG. 21 is a diagram illustrating the detailed configuration of a part of a radiation conversion panel according to a fifth modification.

FIG. 21 is a diagram illustrating the detailed configuration of a part of the radiation conversion panel 64 according to the fifth modification. Although not illustrated in the drawings, the 240 gate lines 110 are connected to each gate driving circuit 150 and each gate line 110 is connected to the pixels 102 through the TFTs 72. One of the 240 gate lines 110 that are connected to each gate driving circuit 150 is connected to the cassette control unit 122 through a bypass line 260. In the bypass line 260, a switching element 262 is provided.

In this case, the bypass line 260 that is connected to the gate line 110 of the first gate driving circuit 150 is called a first bypass line 260 and the bypass line that is connected to the gate line 110 of the second gate driving circuit 150 is called a second bypass line 260. Likewise, the bypass lines that are connected to the gate lines 110 of the third to twelfth gate driving circuits 150 are called third to twelfth bypass lines 260. In order to simplify the description, the gate line 110 that is connected to the first bypass line 260 is called a first scanning gate line 110 and the gate line 110 that is connected to the second bypass line 260 is called as a second scanning gate line 110. Likewise, the gate lines 110 that are connected to the third to twelfth bypass lines 260 are called third to twelfth scanning gate lines 110. In the fifth modification, in order to simplify the description, one of the 240 gate lines 110 that are connected to the gate driving circuit 150 is set as the scanning gate line 110. However, the scanning gate line 110 may not be provided in the gate driving circuit 150 and the plural scanning gate lines 110 may be provided in the gate driving circuit 150.

In the scan mode in the fifth modification, all of the switching elements 262 are turned on or some switching elements 262 are turned on. The first read control unit 130 sequentially outputs the gate signal to the bypass line 260 where the switching element 262 is turned on and the charge that is accumulated in the pixels 102 is sequentially read in a row unit. If the gate signal is output to all of the bypass lines 260 where the switching elements are turned on, one cycle of the scan mode ends and a next cycle starts.

For example, in a case in which the switching elements 262 of all of the bypass lines 260 are turned on, the first read control unit 130 outputs the gate signal to the first bypass line 260 and reads the charge accumulated in the pixels 102 connected to the first scanning gate line 110 in a row unit. The first read control unit 130 outputs the gate signal to the second bypass line 260 and reads the charge accumulated in the pixels 102 connected to the second scanning gate line 110 in a row unit. As such, the first read control unit 130 sequentially outputs the gate signal from the first bypass line 260 to the twelfth bypass line 260 and sequentially reads the charge accumulated in the pixels 102 connected to the first to twelfth scanning gate lines 110 in a row unit. If the gate signal is output to the twelfth bypass line 260, one cycle of the scan mode ends and the gate signal is output to the first bypass line 260 at a next cycle.

That is, the electronic cassette 20 includes at least the plural pixels 102 that are arranged in a matrix, the plural TFTs 72 that are arranged in a matrix to read the electric signals accumulated in the plural pixels 102, the plural gate lines 110 that are connected to the TFTs 72 of each row and are arranged in parallel to the row direction, the plural gate driving circuits 150 that are connected to the plural gate lines 110, outputs the gate signals to the TFTs 72 of each row through the gate lines 110, and are arranged in parallel along the column direction, and the plural signal lines 112 that are arranged in parallel to the column direction to read the electric signals accumulated in the plural pixels 102.

To at least one gate line 110 among the plural gate lines 110, the bypass line 260 where the switching element 262 is provided is connected. That is, the electronic cassette 20 has one or more one bypass lines 260 that have the switching element 262 connected to at least one gate line 110 among the plural gate lines 110.

A gate of the TFT 72 is connected to the gate line 110 and a source thereof is connected to the pixel 102. A drain of the TFT 72 is connected to the signal line 112. If the driving signal a is input to each gate driving circuit 150, each gate driving circuit 150 sequentially selects the gate lines 110 connected to each gate driving circuit, outputs a gate signal to the selected gate line 110, turns on the TFT 72, and sequentially reads the electric signal accumulated in the pixels 102 connected to each gate driving circuit through the plural signal lines 112, in a row unit.

The first read control unit 130 executes the scan mode in which the switching element 262 of the bypass line 260 connected to the predetermined gate line (scanning gate line) 110 is turned on, the gate signal is output, and the electric signals accumulated in the pixels 102 connected to the predetermined gate line 110 are sequentially read in a unit of one row. The second read control unit 136 executes the sequential read mode in which the driving signal a is sequentially input to each gate driving circuit 150, each gate driving circuit 150 is sequentially driven, and the electric signals of the plural pixels 102 are sequentially read in a row unit.

In this case, the user operates the input unit 200 of the console 26 and selects the scanning gate line 110 used in the execution of the scan mode. The selected scanning gate line 110 becomes the predetermined gate line 110 and the pixels 102 that are connected to the selected scanning gate line 110 become the pixels 102 of the predetermined row. Since the user can previously recognize a region of the electronic cassette 20 where the radiation 16 is irradiated by the radiation source 34, the user can select the scanning gate line 110 that corresponds to the irradiation region of the radiation 16. Information that indicates the selected scanning gate line 110 is transmitted from the console 26 to the electronic cassette 20 through the system controller 24. When the scan mode is executed, the first read control unit 130 turns on the switching element 262 of the bypass line 260 that is connected to the scanning gate line 110 selected by the user. In a case in which the execution of the scan mode ends, the first read control unit 130 turns off all of the switching elements 262.

In the fifth modification, since the gate signal is output to only the selected scanning gate line 110 during the execution of the scan mode, a state of the pixels 102 other than the pixels 102 (predetermined pixels 102) that are connected to the selected scanning gate line 110 becomes an exposure state, during the execution of the scan mode. Therefore, the charge according to the irradiated radiation 16 can be accumulated without wasting the radiation 16 having image information. If the irradiation time passes from the timing of the start of irradiation of the radiation 16, the mode transits to the sequential read mode. Therefore, the noise of the radiation image can be decreased without executing the unnecessary exposure after the irradiation of the radiation 16 ends.

Since the user selects the scanning gate line 110 in a region where the radiation 16 is irradiated, the irradiation start determination unit 132 can determine the start of irradiation of the radiation 16 early and surely. Since the gate signal is output to only the selected scanning gate line 110, power consumption by the execution of the scan mode can be suppressed.

Similar to the sequential scan mode, in the scan mode in the fifth modification, the charge accumulated in the pixels 102 of one row may be read in time of 173 μsec. As such, since the charge accumulated in the pixels 102 of one row may be read in time of 173 μsec, determination precision of the start of irradiation of the radiation 16 is not lowered, even though the charge accumulated in the pixels 102 is not added. Since the number of scanning gate lines 110 is small, time of one cycle of the scan mode can be decreased, even though the charge accumulated in the pixels 102 of one row is read in the same time as that of the sequential read mode.

The large number of scanning gate lines 110 of the region where the possibility of the radiation 16 being irradiated is high or the region where the radiation is irradiated may be selected, and the small number of gate lines 110 of the region where the possibility of the radiation 16 being irradiated is low or the region where the radiation is not irradiated may be selected. In a case in which the scan mode is executed, the gate signal is output to only the selected scanning gate line 110. The region where the possibility of the radiation 16 being irradiated is high or the region where the radiation is irradiated may be designated by operating the input unit 200 of the console 26 by the user. In this case, the region where the possibility of the radiation 16 being irradiated is high or the region where the radiation is irradiated may be designated directly by the user or the control unit 212 of the system controller 24 may read the region according to the image capturing part and the diagnosis purpose selected by the user, from the table 218, and designate the region. The control unit 212 of the system controller 24 selects the gate lines 110 used in the execution of the scan mode, on the basis of the designated region, and transmits information indicating the selected gate line 110 to the electronic cassette 20.

(Sixth Modification)

In the fourth modification, the gate line 250, the TFT 252, and the pixel 254 for the scan mode are provided separately from the gate line 110, the TFT 72, and the pixel 102. However, by driving the predetermined gate driving circuit 150 used in the execution of the scan mode, the gate line 110, TFT 72, and pixel 102 of the region that is managed by the gate driving circuit 150 may be used for the scan mode.

When the scan mode is executed, the first read control unit 130 outputs the driving signal c to one predetermined gate driving circuit 150. The gate driving circuit 150 that receives the driving signal c sequentially reads the charge accumulated in the pixels 102 of the region managed by the gate driving circuit from the zero-th row to the 239-th row, in a row unit. Thereby, the electric signal of the digital signal is sequentially obtained in a row unit. In a case in which the irradiation start determination unit 132 determines that the value of the electric signal of the digital signal is more than the threshold value, the first read control unit 130 ends the execution of the scan mode. The first read control unit 130 repeats the scan mode until the scan start is determined. That is, in a case in which the end signal d is transmitted from the gate driving circuit 150, the driving signal c is output to the predetermined gate driving circuit 150 again. In this case, similar to the sequential scan mode, the read time of the charge accumulated in the pixels 102 of one row may be 173 μsec. Similar to the scan mode in the exemplary embodiment, the read time of the charge accumulated in the pixels 102 of one row may be 21 μsec.

The user operates the input unit 200 of the console 26 and selects the gate driving circuit 150 used in the execution of the scan mode. Since the user can previously recognize a region of the electronic cassette 20 where the radiation 16 is irradiated by the radiation source 34, the user can set the gate driving circuit 150 that executes the read of the pixels 102 corresponding to the irradiation region of the radiation 16. Information that indicates the gate driving circuit 150 selected by the user is transmitted from the console 26 to the electronic cassette 20 through the system controller 24. When the scan mode is executed, the first read control unit 130 outputs the driving signal c to the gate driving circuit 150 selected by the user as the predetermined gate driving circuit 150.

The user may select the plural gate driving circuits 150 that are used in the execution of the scan mode. In this case, the first read control unit 130 may simultaneously output the driving signal c to the selected gate driving circuits 150. That is, each gate driving circuits 150 may be simultaneously driven. If the first read control unit 130 receives the end signal d from one gate driving circuit 150, the first read control unit 130 may sequentially drive the predetermined gate driving circuits 150 such that the driving signal c is output to a next gate driving circuit 150.

In the sixth modification, since the gate driving circuit 150 other than the selected gate driving circuit 150 does not output the gate signal during the execution of the scan mode, a state of the pixels 102 other than the pixels 102 of the region where the charge is read by the selected gate driving circuit 150 transits to the exposure state during the execution of the scan mode. Therefore, the charge according to the irradiated radiation 16 can be accumulated without wasting the radiation 16 having the image information. If the irradiation time passes from the timing of the start of irradiation of the radiation 16, the mode transits to the sequential read mode. Therefore, the noise of the radiation image can be decreased without performing unnecessary exposure after the end of the irradiation of the radiation 16.

Since the user selects the gate driving circuit 150 to read the charge accumulated in the pixels 102 to be a region where the radiation 16 is irradiated, the irradiation start determination unit 132 can determine the start of irradiation of the radiation 16 early and surely. Since only the selected gate driving circuit 150 reads the charge accumulated in the pixels 102, power consumption by the execution of the scan mode can be suppressed.

(Seventh Modification)

In order to decrease consumption power, with respect to the electronic cassette 20 in a standby mode where image capturing is not scheduled soon, the scan mode preferably starts at appropriate timing immediately before image capturing.

Therefore, as illustrated in FIGS. 22 to 26, the electronic cassette 20 according to the seventh modification sequentially measures its movement amount MV and predicts whether an image can be captured at a current point in time, on the basis of a temporal characteristic of the movement amount MV. The electronic cassette 20 transits from a sleep state to a start state at a timing immediately before image capturing and executes the scan mode. At this time, communication through the system controller 24 is not needed.

Figure 22:
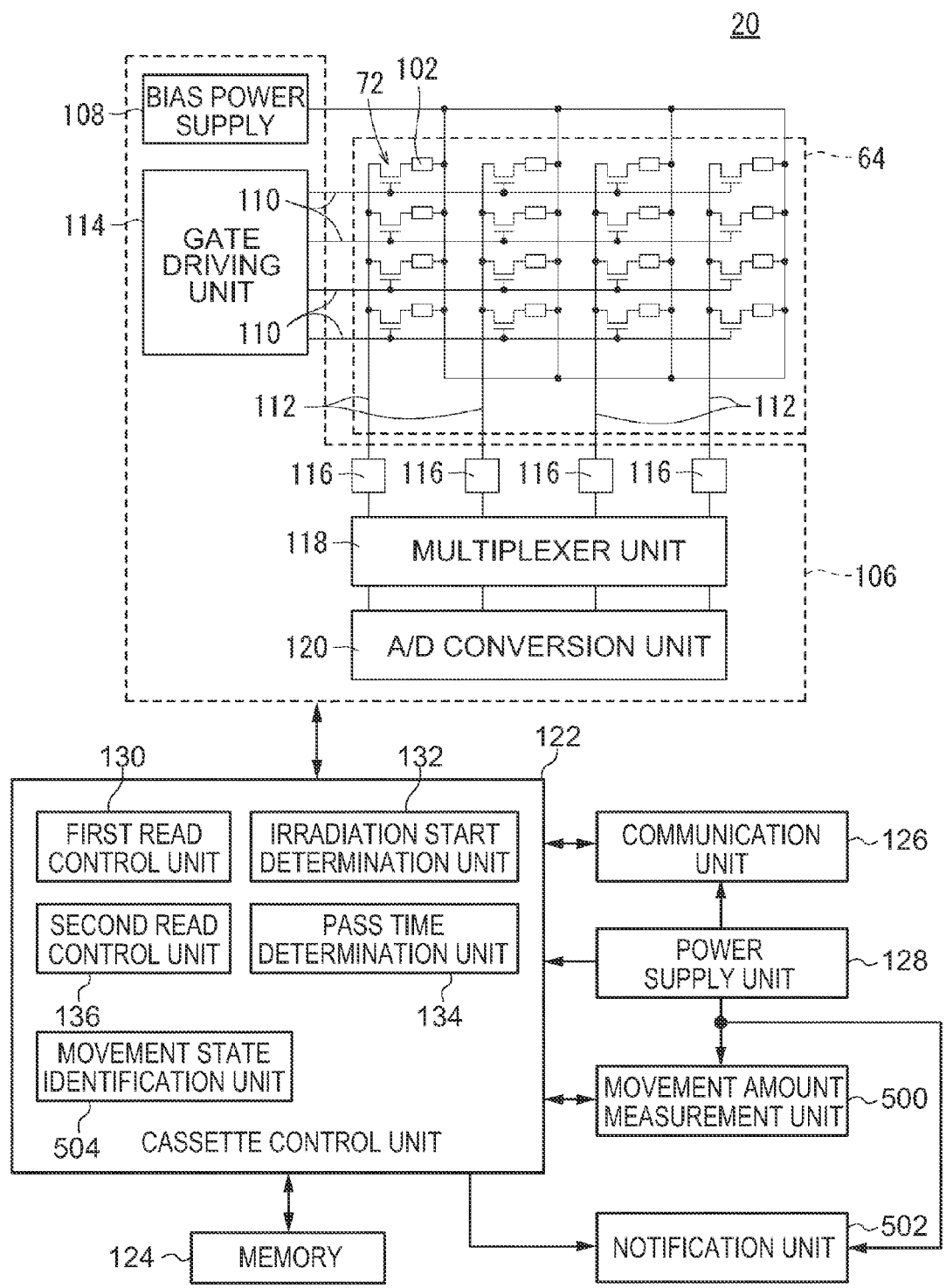
FIG. 22 is a schematic diagram illustrating the electric configuration of an electronic cassette according to a seventh modification.

FIG. 22 is a schematic diagram illustrating the electric configuration of the electronic cassette 20 according to the seventh modification.

The electronic cassette 20 further includes a movement amount measurement unit 500 that measures the movement amount MV of the radiation detector 66 and a notification unit (start/end notification unit) 502 that notifies a user of the change of an operation state of the electronic cassette 20.

The cassette control unit 122 further includes a movement state identification unit 504 that identifies a movement state of the radiation detector 66, in addition to the first read control unit 130, the irradiation start determination unit 132, the passage time determination unit 134, and the second read control unit 136.

Herein, terms of the "movement amount MV" and the "movement state" may be applied to the electronic cassette 20 as well as the radiation detector 66. This is because the radiation detector 66 is generally fixed to an inner portion of the electronic cassette 20 and is substantially a synonym for the electronic cassette 20.

The cassette control unit 122 is connected to the movement amount measurement unit 500 and the notification unit 502, in addition to the memory 124 and the communication unit 126. The power supply unit 128 supplies power to the movement amount measurement unit 500 and the notification unit 502, in addition to the cassette control unit 122, the memory 124, and the communication unit 126.

In the movement amount measurement unit 500, various measurers according to the measured movement amount MV (variable of one or more) may be used. If the movement amount MV is acceleration and/or angular velocity, any one of an acceleration sensor, an angular velocity sensor, or an inertial sensor (a sensor formed by combining the acceleration sensor and the angular velocity sensor) may be used as the movement amount measurement unit 500.

The acceleration sensor may adopt various types that include a piezoelectric type, a capacitive type, a servo type, and an air bubble type. As the angular velocity sensor, gyroscopes of various types that include a mechanical type, a fluid type, an optical type, and a vibration type may be used. The inertial sensor may adopt various types that include a platform type and a strap-down type.

Further, the movement amount MV may be calculated from the physical amount measured by the movement amount measurement unit 500. For example, plural images at different points of time may be captured using a camera incorporated in the electronic cassette 20 and a vector or a distance as the movement amount MV may be acquired using a known image processing technology. As an image capturing element, a photodiode array, a charge coupled device (CCD), a complementary metal oxide semiconductor (CMOS), and the like may be used.

The configuration of the notification unit 502 is not limited as long as the notification unit 502 is any unit that appeals to the five senses (the sensor of sight or the sensor of hearing) of the user. For example, a lamp, a speaker, a liquid crystal display panel, and the like may be used. The notification unit may not be provided in the electronic cassette 20 and information may be notified to the user through an external device (the console 26 or the display device 28 of FIG. 1).

The movement state identification unit 504 identifies whether the electronic cassette 20 is moved on a real space (hereinafter, referred to as moving state) or is stopped (hereinafter, referred to as static state), on the basis of the movement amount MV of the electronic cassette 20. The movement state identification unit 504 determines whether a transition from a sleep state to a start state (or a transition from the start state to the sleep state) is permitted, according to the acquired movement state (for example, history information)

of the electronic cassette 20, and transmits an electric signal that instructs the transition of the operation state of the electronic cassette 20.

Figure 23:
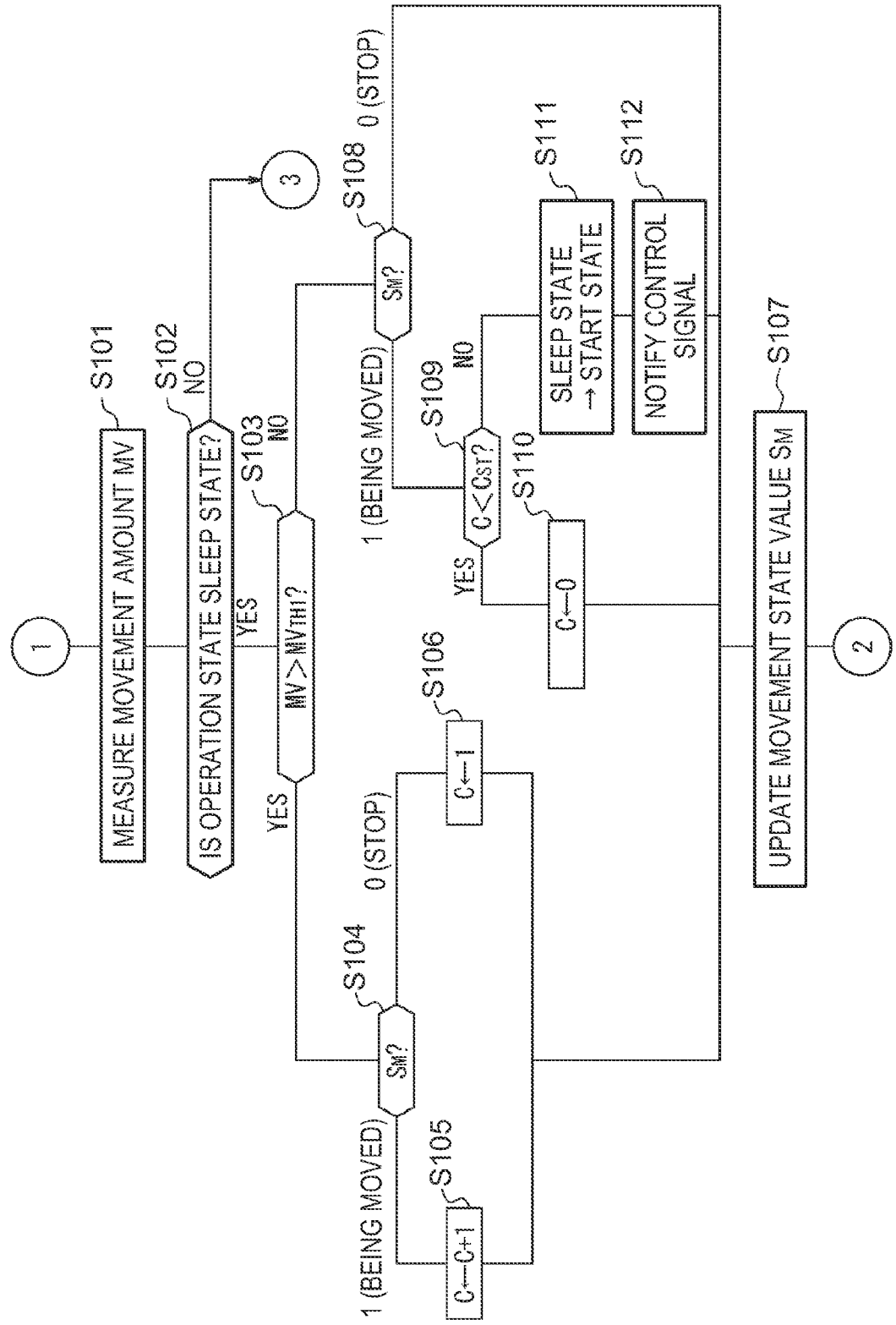
FIG. 23 is a flowchart illustrating an operation of the electronic cassette of FIG. 22.

FIG. 23 is a flowchart illustrating an operation of the electronic cassette 20 according to the seventh modification. The operation of FIG. 23 is executed by performing a timer interruption at a predetermined time interval (hereinafter, referred to as a time interval Δt), for example, in the flowchart of FIG. 12.

First, the movement amount measurement unit 500 measures the movement amount MV of the electronic cassette 20 at the time interval Δt (step S101). The movement amount MV may be any one of the acceleration, the angular velocity, the vector, the distance, and the like. In the seventh modification, in order to simplify the description, the movement amount MV is assumed as one variable (for example, scalar quantity of 0 or more).

Next, the movement state identification unit 504 determines whether the electronic cassette 20 is in the sleep state (step S102). If the electronic cassette 20 is in the sleep state, the movement state identification unit 504 executes step S103. The operation in a case in which it is determined that the electronic cassette 20 is in the start state will be described below (refer to FIG. 25).

Next, the movement state identification unit 504 compares the movement amount MV obtained from the movement amount measurement unit 500 and a predetermined threshold value $MV_{TH1}$ (a first threshold value and a second threshold value) (step S103). In this case, the threshold value $MV_{TH1}$ is a threshold value that is used to identify whether the state of the electronic cassette 20 at a current point in time is the moving state or the static state.

If a condition of $MV > MV_{TH1}$ (YES) is satisfied, the movement state identification unit 504 acquires a movement state value $S_M$ of the electronic cassette 20 and identifies a most recent movement state of the electronic cassette 20 (step S104). In this case, the movement state value $S_M$ is a variable that indicates the most recent movement state of the electronic cassette 20 (for example, at the time of previous measurement). In the seventh modification, if the movement state is the "moving state", $S_M$ is set to 1, and if the movement state is the "static state", $S_M$ is set to 0. The movement state value $S_M$ is not limited to a binary value (1 or 0) and values of three kinds or more may be used.

If the movement state value $S_M$ is 1 (moving state), the movement state identification unit 504 adds a value of a first counter C by 1 (step S105). Meanwhile, if the movement state value $S_M$ is 0, the movement state identification unit 504 sets the value of the first counter C to 1 (step S106). In this case, the value of the first counter C corresponds to the number of times of continuously measuring that the electronic cassette 20 is in the moving state ($S_M$=1) at a current point in time.

Next, the movement state identification unit 504 updates the movement state value $S_M$ (step S107). Specifically, the movement state identification unit 504 compares the movement amount MV at a current point in time measured in step S101 and the threshold value $MV_{TH1}$, determines the movement state value $S_M$ at a current point in time, and sets the determined movement state value $S_M$ as a new movement state value $S_M$.

Meanwhile, returning to step S103, if a condition of $MV \le MV_{TH1}$ (NO) is satisfied, the movement state identification unit 504 acquires a movement state value $S_M$ of the electronic cassette 20 and identifies a most recent movement state of the electronic cassette 20 (step S108).

If $S_M$=0 (static state), the movement state identification unit 504 updates the movement state value $S_M$ (step S107).

Meanwhile, if $S_M$=1 (moving state), the movement state identification unit 504 compares the value of the first counter C and a threshold value $C_{ST}$ (step S109).

If $C < C_{ST}$ (YES), the movement state identification unit 504 sets the value of the first counter C to 0 (step S110) and updates the movement state value $S_M$ (step S107). That is, since the number of times of continuously measuring that the electronic cassette 20 is in the moving state ($S_M$=1) is insufficient, the value of the first counter C is reset to 0.

Meanwhile, if $C \ge C_{ST}$ (NO), the moving state ($S_M$=1) has been maintained for longer than a first predetermined time ($C_{ST} \cdot \Delta t$) going back from a transition point in time of the operation state to the static state ($S_M$=0). At this time, an operation state of the electronic cassette 20 transits from the sleep state to the start state (step S111). At this time, the movement state identification unit 504 transmits a start signal and transmits a predetermined control signal to the notification unit 502. That is, the number of times of continuously measuring that the electronic cassette 20 is in the moving state ($S_M$=1) is sufficient and thus a transition of the electronic cassette 20 to the start state is permitted.

Next, the notification unit 502 receives a control signal from the movement state identification unit 504 and notifies the user of the control signal (step S122). Specifically, the control signal can be notified to the user through a lighting on/off operation by the lamp, an output operation of a beep sound by a speaker, a display operation of characters and symbols by the liquid crystal display panel, and the like. The movement state identification unit 504 updates the movement state value $S_M$ (step S107).

In this way, the electronic cassette 20 identifies the movement state on the basis of the movement amount MV and maintains the sleep state or transits from the sleep state to the start state.

Figure 24:
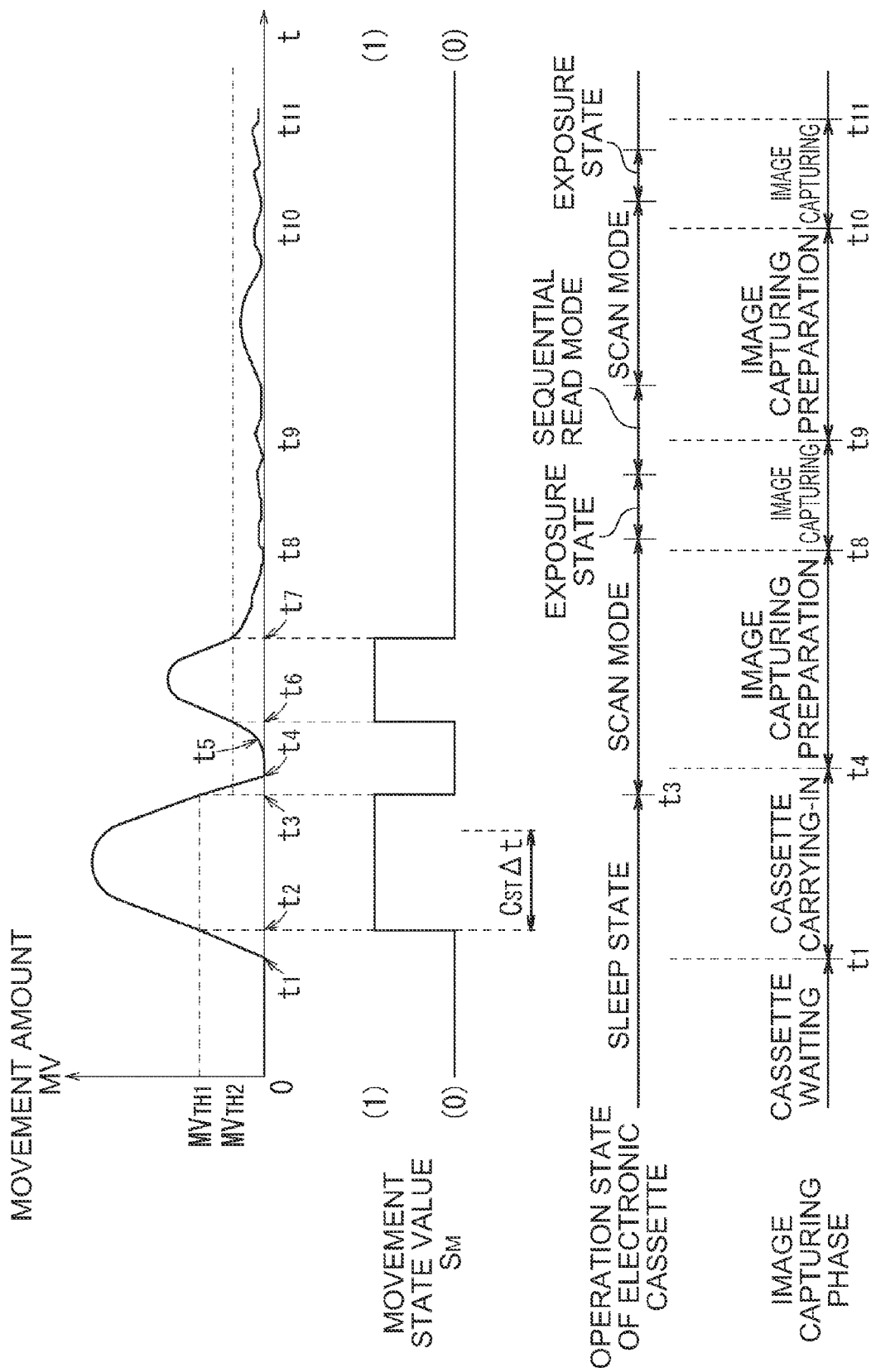
FIG. 24 is a schematic diagram illustrating time series of the operation of the electronic cassette of FIG. 22.

Next, an example of the operation of the electronic cassette 20 immediately before the radiation image capturing will be specifically described with reference to a schematic diagram of FIG. 24 illustrating time series.

First, the user places the electronic cassette 20 in a predetermined storage place and maintains the electronic cassette 20 in the standby state (time 0 to time t1). The movement amount MV that is measured in step S101 is always 0. At this time, by repeating the execution of steps S101, S102, S103, S108, and S107 of FIG. 23, the electronic cassette 20 maintains the sleep state.

Next, the user extracts the electronic cassette 20 from the storage place and carries the electronic cassette 20 in an image capturing field (time t1 to time t4). While the electronic cassette 20 is moving, the movement amount MV becomes a value that is more than 0. During a period from the time t2 when the movement amount MV is more than the threshold value $MV_{TH1}$ to the time t3 when the movement amount MV is less than the threshold value $MV_{TH1}$, the execution of steps S101, S102, S103, S104, S105, and S107 of FIG. 23 are repeated. At this time, since the value of the first counter C is sequentially added, the first counter C adopts a value that is more than the threshold value $C_{ST}$ at the time t3.

If the movement amount MV is first less than the threshold value $MV_{TH1}$ approximately at the time t3, steps S101, S102, S103, S108, S109, S111, S112, and S107 of FIG. 23 are executed. At this time, the operation state of the electronic cassette 20 transits from the sleep state to the start state. Then, the first read control unit 130 starts the scan mode.

As such, since the movement amount measurement unit 500 to measure the movement amount MV of the radiation detector 66 is provided, it can be predicted whether an image can be captured at a current point in time, using the movement amount MV. That is, a consumption power can be decreased by starting the scan mode at an appropriate timing immediately before the image capturing.

In this case, the scan mode is not limited to the read operation described in the exemplary embodiment or the fourth modification, and various methods may be adopted. For example, in the scan mode, the electric signals that are accumulated in the pixels 102 and 254 may be read by the number of times of reading smaller than the total number (in the exemplary embodiment, 2880 rows) of rows of the radiation detector 66, and the electric signals may be read using the sequential read mode described above.

The movement state identification unit 504 to identify the movement state value $S_M$ of the radiation detector 66 on the basis of the measured movement amount MV is further provided. Therefore, it can be precisely predicted whether an image can be captured at a current point in time using the electronic cassette 20.

If the movement state value $S_M$ of the electronic cassette 20 transits from the moving state ($S_M$=1) to the static state ($S_M$=0) and the moving state ($S_M$=1) has been maintained for longer than the first predetermined time ($C_{ST}\cdot\Delta t$) going back from the transition point in time, the scan mode of the electronic cassette 20 starts. If the electronic cassette 20 in the standby state receives the temporary shock and moves, a consumption power of the electronic cassette 20 can be further decreased by not executing the scan mode.

Figure 25:
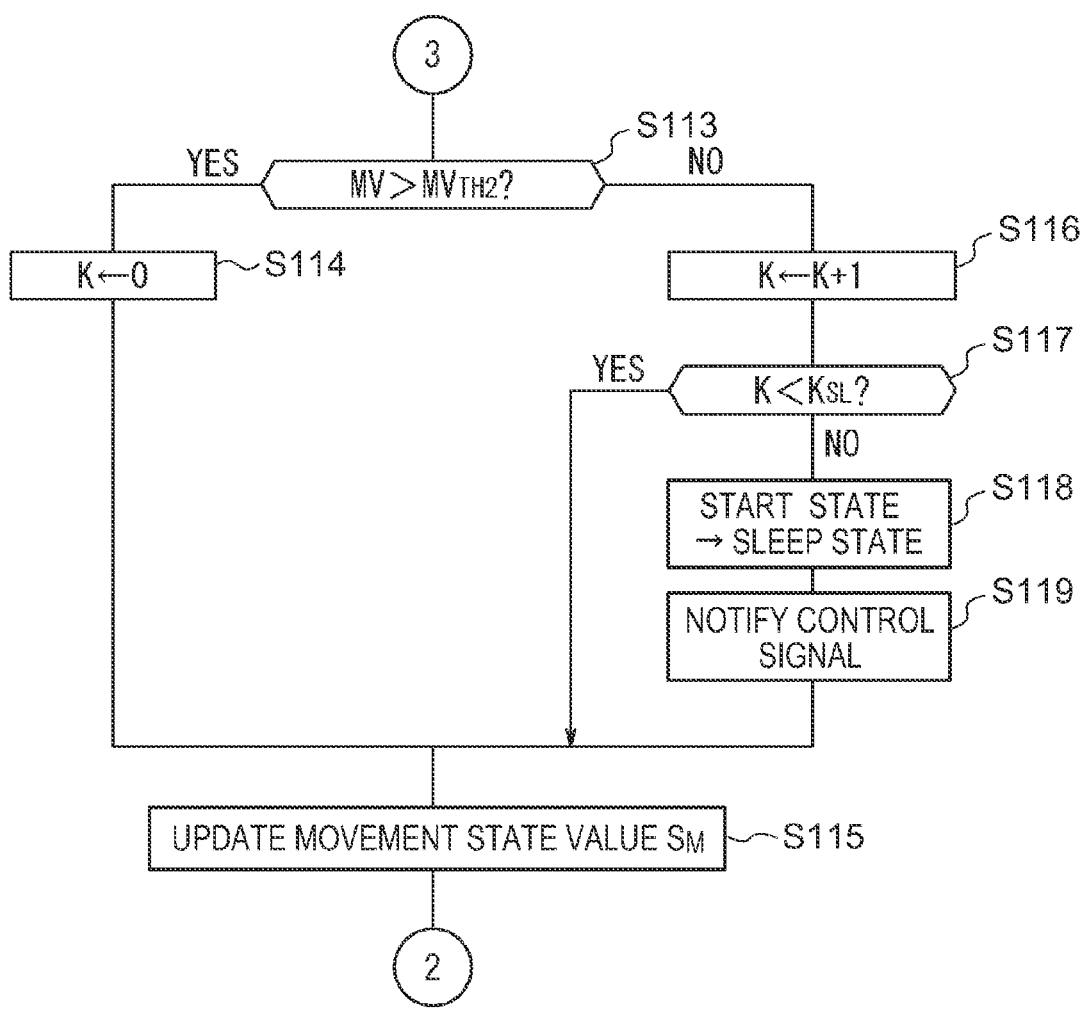
FIG. 25 is a flowchart illustrating an operation of the electronic cassette of FIG. 22.

Meanwhile, returning to step S102 of FIG. 23, if it is determined that the electronic cassette 20 is in the start state, an operation that is illustrated in the flowchart of FIG. 25 is executed.

First, the movement state identification unit 504 compares the movement amount MV obtained from the movement amount measurement unit 500 and a threshold value $MV_{TH2}$ (a first threshold value and a second threshold value) (step S113). In this case, the threshold value $MV_{TH2}$ is a threshold value that is used to identify whether a state of the electronic cassette 20 at a current point in time is the moving state or the static state. The threshold value $MV_{TH2}$ in the start state is set to be smaller than the threshold value $MV_{TH1}$ in the sleep state (refer to FIGS. 24 and 26).

If a condition of $MV>MV_{TH2}$ (YES) is satisfied, the movement state identification unit 504 sets a value of a second counter K to 0 (step S114). In this case, the value of the second counter K corresponds to the number of times of continuously measuring that the electronic cassette 20 is in the static state ($S_M$=0) at a current point in time. Then, the movement state identification unit 504 updates the movement state value $S_M$ (step S115).

Meanwhile, if a condition of $MV \leq MV_{TH2}$ (NO) is satisfied, the movement state identification unit 504 adds the value of the second counter K by 1 (step S116).

Next, the movement state identification unit 504 compares the value of the second counter K and a second threshold value $K_{SL}$ (step S117). If a condition of $K<K_{SL}$ (YES) is satisfied, the movement state identification unit 504 updates the movement state value $S_M$ (step S115). Meanwhile, if a condition of $K \geq K_{SL}$ (NO) is satisfied, an operation state of the electronic cassette 20 transits from the start state to the sleep state (step S118). At this time, the movement state identification unit 504 transmits a sleep signal and transmits a predetermined control signal to the notification unit 502. That is, the number of times of continuously measuring that the electronic cassette 20 is in the static state ($S_M$=0) is sufficient and a transition of the electronic cassette 20 to the sleep state is permitted.

Next, the notification unit 502 receives a control signal from the movement state identification unit 504 and notifies the user of the control signal (step S119). Specifically, the control signal can be notified to the user through a lighting on/off operation by the lamp, an output operation of a beep sound by a speaker, a display operation of characters and symbols by the liquid crystal display panel, and the like. The movement state identification unit 504 updates the movement state value $S_M$ (step S115).

In this way, the electronic cassette 20 identifies the movement state on the basis of the movement amount MV and maintains the sleep state or transits from the start state to the sleep state.

Figure 26:
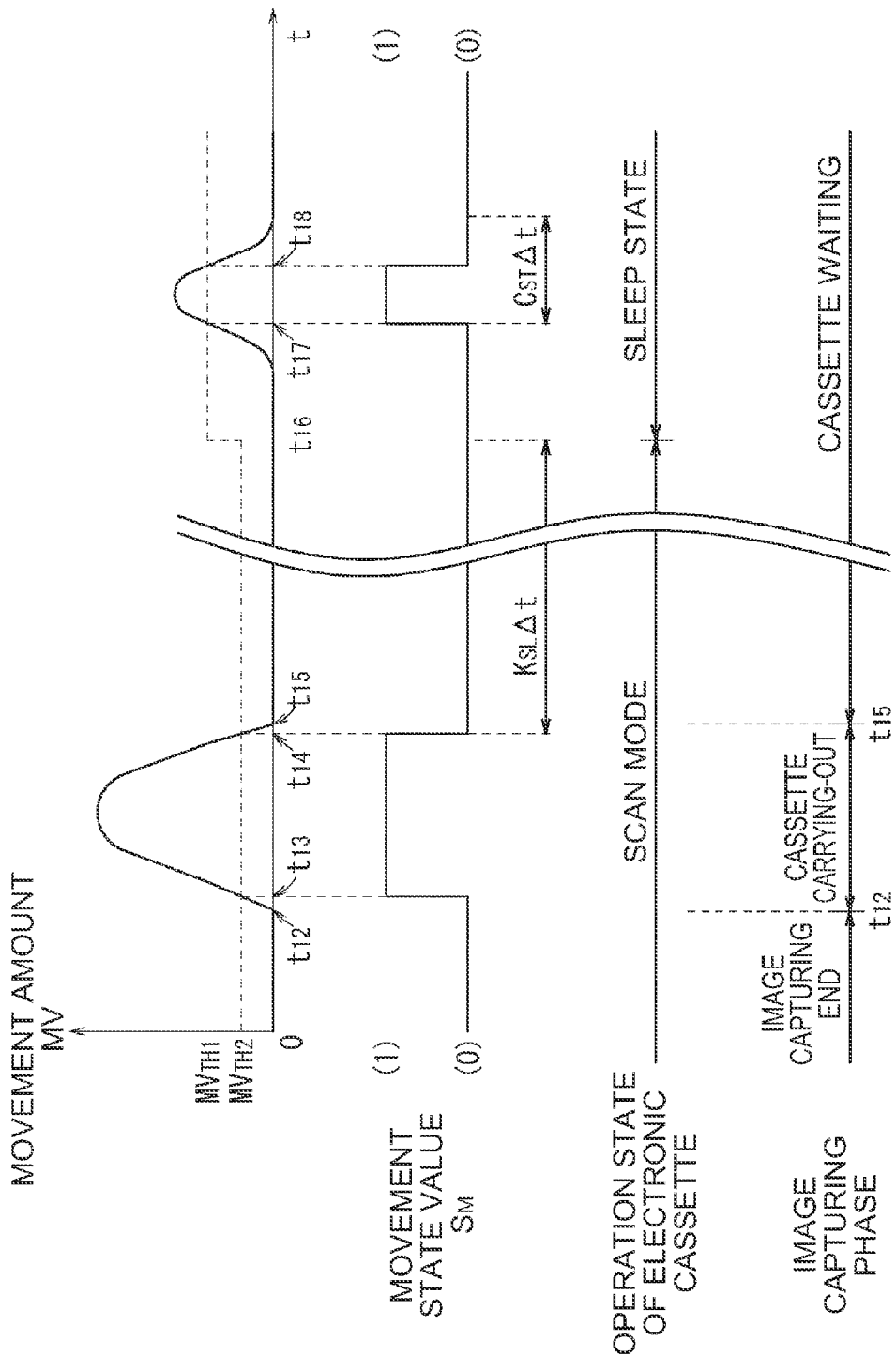
FIG. 26 is a schematic diagram illustrating time series of the operation of the electronic cassette of FIG. 22.

Next, an example of the operation of the electronic cassette 20 during capturing of a radiation image or immediately after the capturing of the radiation image will be specifically described with reference to schematic diagrams of FIGS. 24 and 26 illustrating time series.

As illustrated in FIG. 24, after carrying the electronic cassette 20 in the image capturing field (time t4), the user sequentially performs individual works such as an image capturing preparation (time t4 to time t8), image capturing (time t8 to time t9), an image capturing preparation (time t9 to time t10), and image capturing (time t10 to time t11).

For example, during a period from the time t6 to the time t7 during the image capturing preparation, the movement amount MV that is measured in step S101 is more than the threshold value $MV_{TH2}$. At this time, the execution of steps S101 and S102 of FIG. 23 and steps S113, S114, and S115 of FIG. 25 are repeated and the electronic cassette 20 maintains the start state.

During a period from the time t7 to the time t11, the movement amount MV that is measured in step S101 is less than the threshold value $MV_{TH2}$. At this time, the execution of steps S101 and S102 of FIG. 23 and steps S113, S116, S117, and S115 of FIG. 25 are repeated. However, a time period from the time t7 to the time t11 is assumed as relatively short time that is not more than the second predetermined time ($K_{SL} \cdot \Delta t$).

As illustrated in FIG. 26, after the radiation image capturing ends, the user carries the electronic cassette 20 and places the electronic cassette 20 in a predetermined storage place (time t12 to time t15). After the most recent time t14 when the movement amount MV is more than the threshold value $MV_{TH2}$, the execution of steps S101 and S102 of FIG. 23 and steps S113, S116, S117, and S115 of FIG. 25 are repeated. At this time, the value of the second counter K is sequentially added as time passes.

If the value of the second counter K is more than the predetermined threshold value $K_{SL}$, that is, the time is for longer than the second predetermined time ($K_{SL} \cdot \Delta t$) from the time t14 when the operation state transits to the static state, steps S101 and S102 of FIG. 23 and steps S113, S116, S117, S118, and S119 of FIG. 25 are executed. At this time, the operation state of the electronic cassette 20 transits from the start state to the sleep state. The first read control unit 130 ends the scan mode.

The threshold value $K_{SL}$ in the transition from the start state to the sleep state is set to be larger than the threshold value $C_{ST}$ in the transition from the sleep state to the start state. As a result, an unexpected transition (transition from the start state to the sleep state) can be prevented during use of the electronic cassette 20 (refer to the operation of the time t17 to the time 18 in FIG. 26).

The threshold value $MV_{TH2}$ in the start state is set to be smaller than the threshold value $MV_{TH1}$ in the sleep state. As a result, since the movement state can be easily identified as the moving state during the start of the electronic cassette 20, an unexpected transition (transition from the start state to the sleep state) can be prevented during use of the electronic cassette 20.

The threshold value (a first threshed value) to identify that the movement state of the electronic cassette 20 is the static state ($S_M=0$) may be different from the threshold value (a second threshed value) to identify that the movement state of the electronic cassette 20 is the moving state ($S_M=1$). For example, if the movement amount MV is the first threshold value or more and is the second threshold value or less, the movement state of the electronic cassette 20 may be defined as a "rocking state" ($S_M=2$). If the movement state of the electronic cassette 20 is the rocking state, the use state of the electronic cassette 20 may be unfixed, and this state may be used in start/end control of the scan mode as a state in a dead zone time.

The invention has been described using the exemplary embodiment. However, a technical range of the invention is not limited to the exemplary embodiment. It is apparent to those skilled in the art that the exemplary embodiment is variously changed or improved. Also, it is apparent from claims that exemplary embodiments where various changes and improvements are made can be included in the technical range of the invention.

Second Exemplary Embodiment

Hereinafter, the second exemplary embodiment of the invention will be described in detail with reference to the drawings. In this case, an example of the case where the invention is applied to a radiology information system that is a system to wholly manage image handled in a radiology department in a hospital will be described.

Figure 27:
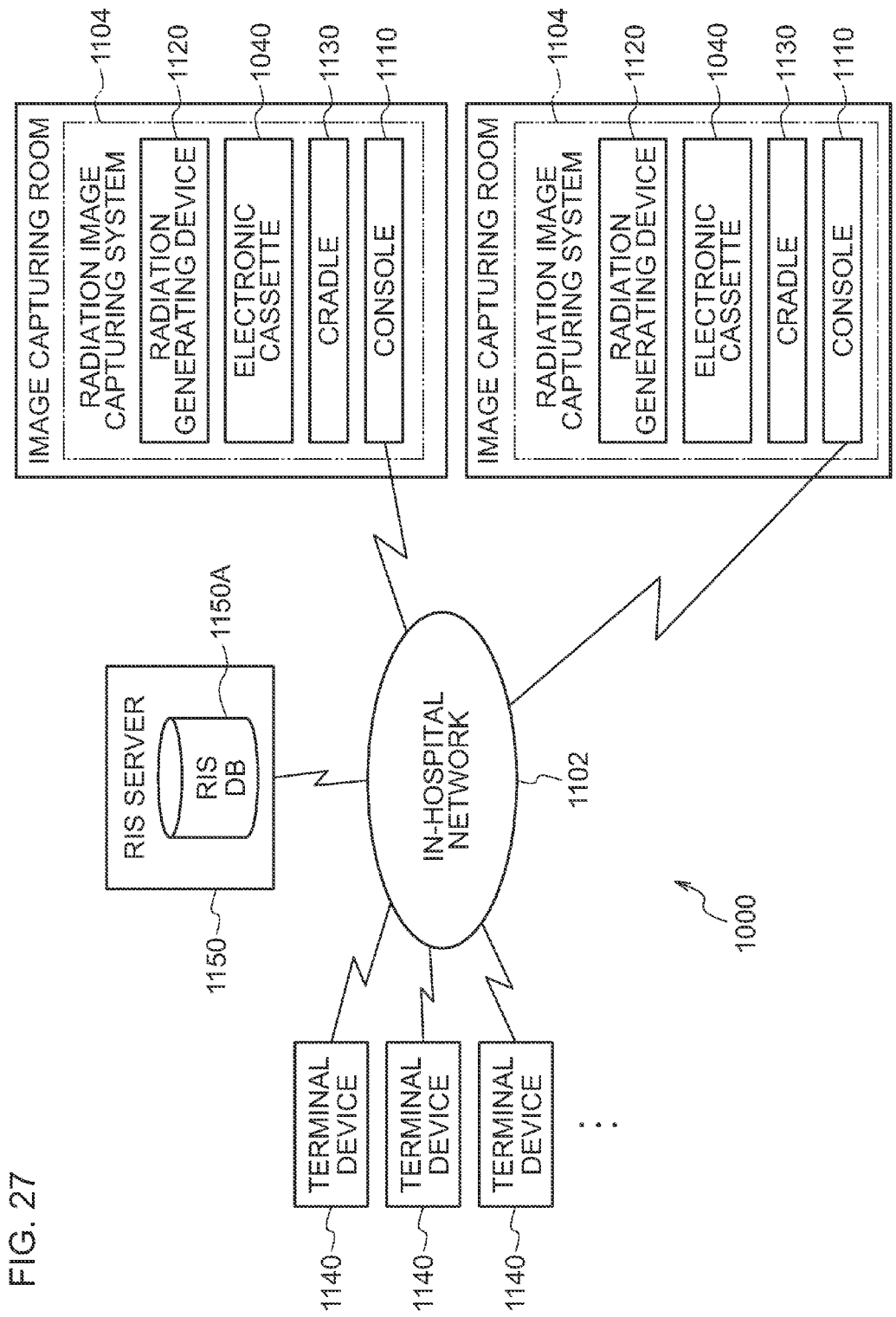
FIG. 27 is a block diagram illustrating the configuration of a radiation information system according to a second exemplary embodiment.

First, the configuration of a radiology information system (hereinafter, referred to as "RIS") 1100 according to this exemplary embodiment will be described, referring to FIG. 27.

The RIS 1100 is a system for carrying out information management such as scheduling of examinations/treatments and recording of diagnoses in the radiology department. The RIS 1110 structures a part of a hospital information system (hereinafter, referred to as "HIS").

The RIS 1100 has plural image capturing request terminal devices (hereinafter, referred to as "terminal devices") 114, an RIS server 1150, and radiation image capturing systems (hereinafter, referred to as "image capturing systems") 1104 that are individually set in radiation image capturing rooms (or operating rooms) within the hospital. The terminal devices 114, the RIS server 1150, and the radiation image capturing systems 1104 are connected to an in-hospital network 1102 that is configured using a wired or wireless local area network (LAN). The RIS 1100 forms a part of the HIS that is provided in the same hospital. An HIS server (not illustrated in the drawings) that manages the entire HIS is connected to the in-hospital network 1102.

The terminal device 1140 is for a doctor or a radiological technologist to carry out inputting and browsing of diagnostic information and reservations of facilities. Requests for capturing of radiation images and reservations for image capturing are also made through the terminal device 1140. Each of the terminal devices 1140 is configured to include a personal computer having a display device, and can communicate with the RIS server 1150 through the in-hospital network 1102.

The RIS server 1150 receives image capturing requests from the individual terminal devices 1140, and manages the image capturing schedule of radiation images in the image capturing systems 1104. The RIS server 1150 is configured to include a database 1150A.

The database 1150A includes information that is related to a patient, such as attribute information of the patient (subject) (a name, a sex, a birth date, an age, a blood type, a weight, and a patient identification (ID), a patient's history of past illness, a history of past examinations/treatments, and radiation images captured in the past, information that is related to the electronic cassette 1040 to be described below that is used in the image capturing system 1104, such as an identification number (ID information), a type, a size, sensitivity, a use start date, and the number of times of use, and environment information expressing an environments in which radiation images are captured by using the electronic cassette 1040, that is, an environment in which the electronic cassette 1040 is used (for example, a radiation image capturing room or an operating room).

The image capturing system 1104 performs capturing of radiation images by the operation of a doctor or a radiological technologist according to an instruction from the RIS server 1150. The image capturing system 1104 has a radiation generating device 1120 that irradiates radiation X (refer to FIG. 32) of a radiation dose according to exposure conditions onto the subject, from a radiation source 1121 (refer to FIG. 28), an electronic cassette 1040 that incorporates a radiation detector 1020 (refer to FIG. 32) that generates absorbs the radiation X transmitted through the image capturing part of the subject, generates the charge, and generates image information indicating a radiation image, on the basis of the generated charge amount, a cradle 1130 that charges a battery incorporated in the electronic cassette 1040, and a console 1110 that controls the electronic cassette 1040 and the radiation generating device 1120.

The console 1110 acquires various types of information included in the database 1150A, from the RIS server 1150, and stores the information in an HDD 1116 (refer to FIG. 34) to be described below. The console 1110 controls the electronic cassette 1040 and the radiation generating device 1120, using the information, if necessary.

Figure 28:
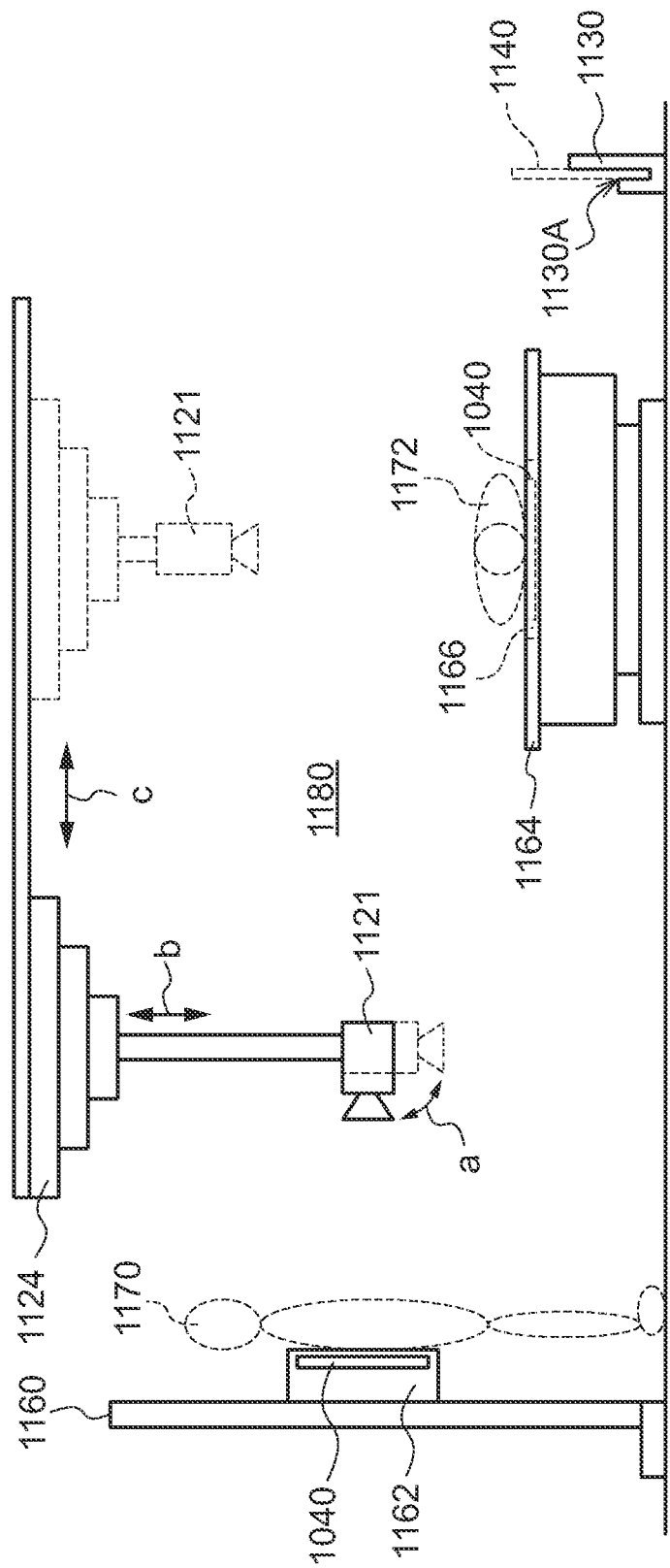
FIG. 28 is a side view illustrating an example of an arrangement state of each device in a radiation image capturing room of the radiation image capturing system according to the second exemplary embodiment.

FIG. 28 is a diagram illustrating an example of an arrangement state of each device in a radiation image capturing room 1108 of the image capturing system 1104 according to the second exemplary embodiment.

As illustrated in FIG. 28, a rack 1160 that is used when radiation image capturing in a standing state is performed, and a bed 1164 that is used when radiation image capturing in a lying state is performed are disposed in the radiation image capturing room 44. The space in front of the rack 1160 is an image capturing position 1170 for the subject when radiation image capturing in the standing state is performed. The space above the bed 1164 is an image capturing position 1172 for the subject when radiation image capturing in a lying state is performed.

In the rack 1160, a holding portion 1162 that holds the electronic cassette 1040 is provided. When radiation image capturing in the standing state is performed, the electronic cassette 1040 is held by the holding portion 1162. Likewise, in the bed 1164, a holding portion 1166 that holds the electronic cassette 1040 is provided. When radiation image capturing in the lying state is performed, the electronic cassette 1040 is held by the holding portion 1166.

In the radiation image capturing room 1180, a supporting/moving mechanism 1124 that supports the radiation source 1121 such that the radiation source 1121 is rotatable around a horizontal axis (direction of an arrow a in FIG. 28), is movable in a vertical direction (direction of an arrow b in FIG. 28), and is movable in a horizontal direction (direction of an arrow c in FIG. 28), is provided in the radiation image capturing room 44 in order to make both radiation image capturing in the standing state and radiation image capturing in the lying state possible by the radiation from the single radiation source 1121. In this case, the supporting/moving mechanism 1124 includes a driving source that rotates the radiation source 1121 around the horizontal axis, a driving source that moves the radiation source 1121 in the vertical direction, and a driving source that moves the radiation source 1121 in the horizontal direction (none of these driving sources is illustrated).

In the cradle 1130, a storing portion 1130A that can store the electronic cassette 1040 is formed.

A battery that is incorporated in the electronic cassette 1040 is charged in a state in which the electronic cassette 1040 is stored in the storing portion 1130A of the cradle 1130, when the electronic cassette 1040 is not used. When a radiation image is captured, the electronic cassette 1040 is extracted from the cradle 1130 by the radiographer. If the image capturing posture is the standing posture, the electronic cassette 1040 is held by the holding portion 1162 of the rack 1160. If the image capturing posture is the lying posture, the electronic cassette 1040 is held by the holding portion 1166 of the bed 1164.

In the image capturing system 1104 according to this exemplary embodiment, various types of information is transmitted and received between the radiation generating device 1120 and the console 1110 and between the electronic cassette 1040 and the console 1110, through the wireless communication.

The electronic cassette 1040 is not used only in a state in which the electronic cassette 1040 is held by the holding portion 1162 of the rack 1160 or the holding portion 1166 of the bed 1164. Since the electronic cassette 1040 is portable, the electronic cassette 1040 can be used in a state in which the electronic cassette 1040 is not held by the holding portion, when arms, legs and the like are imaged.

Figure 29:
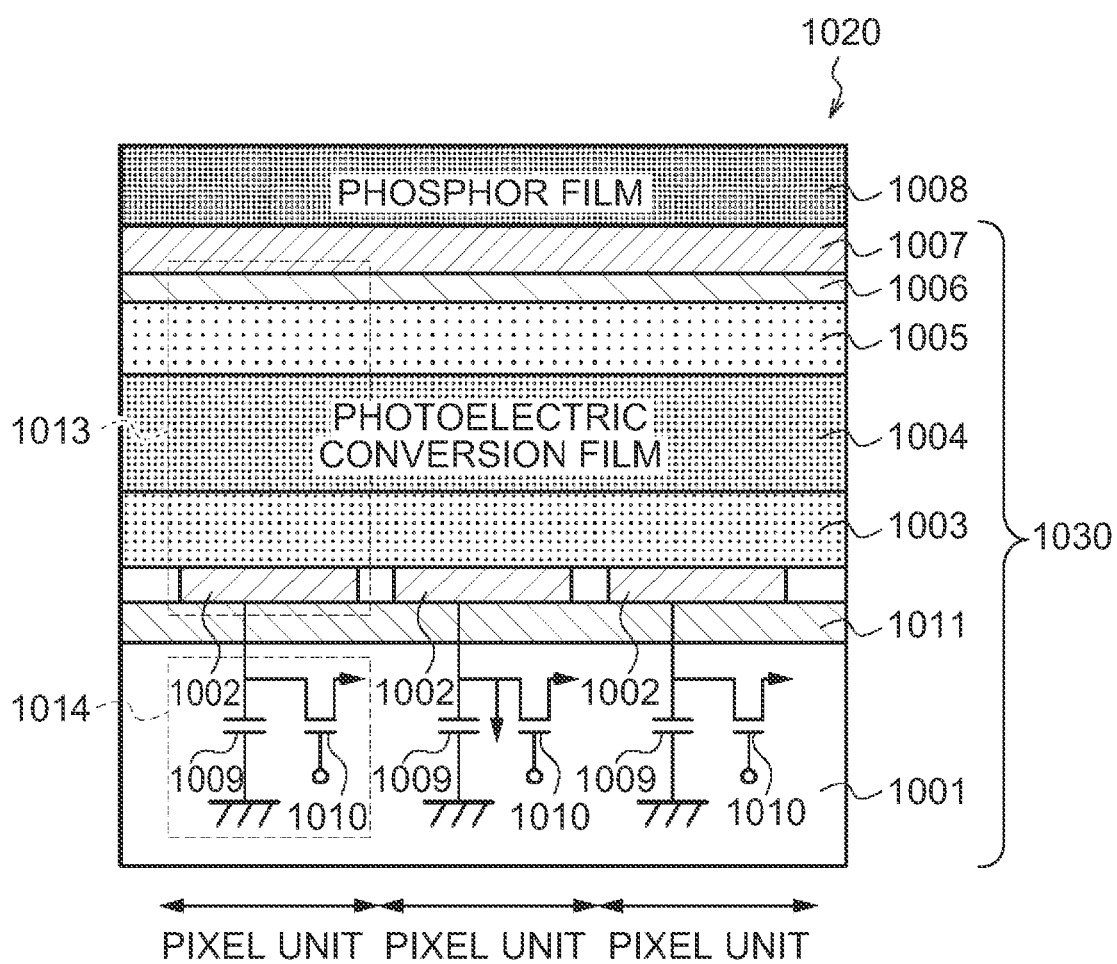
FIG. 29 is a cross-sectional view illustrating the schematic configuration of three pixels of a radiation detector according to the second exemplary embodiment.

Next, the configuration of the radiation detector 1020 according to this exemplary embodiment will be described. FIG. 29 is a cross-sectional view illustrating the schematic configuration of three pixels of the radiation detector 1020 according to the second exemplary embodiment.

As illustrated in FIG. 29, in the radiation detector 1020 according to this exemplary embodiment, a signal output 1014, a sensor unit 1013, and a scintillator 1008 are sequentially laminated on an insulating substrate 1001, and a pixel is configured by the signal output unit 1014 and the sensor unit 1013. The plural pixels are disposed on the substrate 1001 and the signal output unit 1014 and the sensor unit 1013 in each pixel are configured to overlap each other.

The scintillator 1008 is formed on the sensor unit 1013 with a transparent insulating film 1007 interposed therebetween, and has a phosphor that converts radiation incident from the upper side (the side opposite to the substrate 1001) or the lower side into light and emits the light. The provision of the scintillator 1008 makes it possible to absorb radiation transmitted through the subject and emit light.

It is preferable that the wavelength range of light emitted by the scintillator 1008 be a visible light range (wavelength of 360 nm to 830 nm). It is more preferable that the wavelength range of light include a green wavelength range in order to capture a monochromatic image using the radiation detector 1020.

Specifically, in a case in which image capturing is performed using X-rays as radiation, it is preferable that the phosphor used for the scintillator 1008 include cesium iodide (CsI). It is more preferable to use CsI (Ti) (cesium iodide in which thallium is added) having an emission spectrum of 420 nm to 600 nm during the emission of X-rays. The emission peak wavelength of CsI (Ti) in the visible light range is 565 nm.

The sensor unit 1013 has an upper electrode 1006, a lower electrode 1002, and a photoelectric conversion film 1004 provided between the upper and lower electrodes. The photoelectric conversion film 1004 is formed of an organic photoelectric conversion material that absorbs the light emitted from the scintillator 1008 and generates the charge.

The upper electrode 1006 needs to make light generated by the scintillator 1008 incident on the photoelectric conversion film 1004. Therefore, it is preferable that the upper electrode 1006 be made of a conductive material that is at least transparent with respect to the emission wavelength of the scintillator 1008. Specifically, it is preferable that the upper electrode 1006 be made of a transparent conducting oxide (TCO) having high transmittance with respect to visible light and a small resistance value. A metal thin film, such as an Au thin film, may be used as the upper electrode 1006. However, when the transmittance increases to 90% or more, the resistance value is likely to increase. Therefore, it is preferable that the upper electrode 1006 be made of TCO. For example, it is preferable that the upper electrode 1006 be made of ITO, IZO, AZO, FTO, $SnO_2$, $TiO_2$, or $ZnO_2$. It is most preferable that the upper electrode 1006 be made of ITO, in terms of a simple processing, low resistance, and transparency. One upper electrode 1006 may be common to all of the pixels or the upper electrode 1006 may be divided for each pixel.

The photoelectric conversion film 1004, includes the organic photoelectric conversion material, and absorbs light emitted from the scintillator 1008 and generates a charge corresponding to the absorbed light. When the photoelectric conversion film 1004 includes the organic photoelectric conversion material, the photoelectric conversion film 1004 has a sharp absorption spectrum in a visible light range, electromagnetic waves other than the light emitted from the scintillator 1008 is hardly absorbed by the photoelectric conversion film 1004, and noise that is generated by absorbing the radiation such as the X-rays by the photoelectric conversion film 1004 can be effectively suppressed.

It is preferable that the absorption peak wavelength of the organic photoelectric conversion material forming the photoelectric conversion film 1004 be close to the emission peak wavelength of the scintillator 1008 in order to most effectively absorb light emitted from the scintillator 1008. It is ideal that the absorption peak wavelength of the organic photoconductor is matched with the emission peak wavelength of the scintillator 1008. However, when the difference between the absorption peak wavelength and the emission peak wavelength is small, the light that is emitted from the scintillator 1008 can be sufficiently absorbed. Specifically, the difference between the absorption peak wavelength of the organic photoconductor and the emission peak wavelength of the scintillator 1008 with respect to radiation is preferably 10 nm or less and more preferably, 5 nm or less.

Examples of the organic photoelectric conversion material that can satisfy the above-mentioned conditions include a quinacridone-based organic compound and a phthalocyanine-based organic compound. For example, the absorption peak wavelength of quinacridone in the visible light range is 560 nm. Therefore, when quinacridone is used as the organic photoconductor and CsI (Ti) is used as the material forming the scintillator 1008, the difference between the peak wavelengths can be decreased to 5 nm or less and the amount of charge generated by the photoelectric conversion film 1004 can be substantially maximized.

Next, the photoelectric conversion film 1004 that can be applied to the radiation detector 1020 according to this exemplary embodiment will be described in detail.

An electromagnetic wave absorption/photoelectric conversion portion of the radiation detector 1020 according to this exemplary embodiment may be formed by an organic layer including a pair of electrodes 1002 and 1006 and the organic photoelectric conversion film 1004 interposed between the electrodes 1002 and 1006. Specifically, the organic layer may be formed by laminating or mixing, for example, an electromagnetic wave absorption portion, a photoelectric conversion portion, an electron transport portion, a hole transport portion, an electron blocking portion, a hole blocking portion, a crystallization prevention portion, an electrode, and an interlayer contact improvement portion.

It is preferable that the organic layer include an organic p-type compound or an organic n-type compound.

The organic p-type compound (semiconductor) is a donor-type organic compound (semiconductor) whose representative example is a hole-transport-type organic compound and means an organic compound which readily donates electrons. Specifically, in a case in which two organic materials contact each other during use, one organic compound with low ionization potential is the organic p-type semiconductor. Therefore, any organic compound may be used as the donor-type organic compound, as long as it has an electron donating property.

The organic n-type compound (semiconductor) is an acceptor-type organic compound (semiconductor) whose representative example is an electron-transport-type organic compound and means an organic compound which readily accepts electrons. Specifically, in a case in which two organic compounds contact each other during use, one organic compound with high electron affinity is the organic n-type semiconductor. Therefore, any organic compound may be used as the acceptor-type organic compound, as long as it has an electron accepting property.

Materials applicable to the organic p-type semiconductor and the organic n-type semiconductor and the configuration of the photoelectric conversion film 1004 have been described in detail in JP-A No. 2009-32854 and thus a detailed description thereof will not be repeated here. The photoelectric conversion film 1004 may be formed to include fullerene or carbon nanotube.

It is preferable that the thickness of the photoelectric conversion film 1004 be as large as possible in terms of the absorption of light from the scintillator 1008. However, when the thickness of the photoelectric conversion film 1004 is more than a predetermined value, the intensity of the electric field of the photoelectric conversion film 1004 generated by the bias voltage applied from both ends of the photoelectric conversion film 1004 is reduced, which makes it difficult to collect charge. Therefore, the thickness of the photoelectric conversion film 1004 is preferably from 30 nm to 300 nm, more preferably from 50 nm to 250 nm, and most preferably from 80 nm to 200 nm.

In the radiation detector 1020 shown in FIG. 29, one photoelectric conversion film 1004 is common to all of the pixels. However, the photoelectric conversion film 1004 may be divided for each pixel.

The lower electrode 1002 is a thin film that is divided for each pixel. The lower electrode 1002 may be appropriately made of a transparent or opaque conductive material, such as aluminum or silver.

The thickness of the lower electrode 1002 may be, for example, from 30 nm to 300 nm.

In the sensor unit 1013, a predetermined bias voltage can be applied between the upper electrode 1006 and the lower electrode 1002 to move one of the charges (a hole and an electron) generated from the photoelectric conversion film 1004 to the upper electrode 1006 and move the other charge to the lower electrode 1002. In the radiation detector 1020 according to this exemplary embodiment, a wiring line is connected to the upper electrode 1006 and the bias voltage is applied to the upper electrode 1006 through the wiring line. It is assumed that the polarity of the bias voltage is determined such that the electron generated in the photoelectric conversion film 1004 is moved to the upper electrode 1006 and the hole is moved to the lower electrode 1002. However, the polarity may be reversed.

The photoelectric conversion unit 1013 forming each pixel may include at least the lower electrode 1002, the photoelectric conversion film 1004, and the upper electrode 1006. In order to prevent an increase in dark current, it is preferable that at least one of the electron blocking film 1003 and the hole blocking film 1005 be provided, and it is more preferable that both the electron blocking film 1003 and the hole blocking film 1005 be provided.

The electron blocking film 1003 may be provided between the lower electrode 1002 and the photoelectric conversion film 1004. In a case in which the bias voltage is applied between the lower electrode 1002 and the upper electrode 1006, it is possible to prevent an increase in the dark current due to the injection of electrons from the lower electrode 1002 into the photoelectric conversion film 1004.

The electron blocking film 1003 may be made of an electron donating organic material.

In actuality, the material used for the electron blocking film 1003 may be selected according to a material forming the adjacent electrode and a material forming the adjacent photoelectric conversion film 1004. It is preferable that the material used for the electron blocking film 1003 have an electron affinity (Ea) that is at least 1.3 eV higher than the work function (Wf) of the material forming the adjacent electrode and have an ionization potential (Ip) equal to or less than that of the material forming the adjacent photoelectric conversion film 1004. Materials applicable as the electron donating organic material have been described in detail in JP-A No. 2009-32854 and thus a detailed description thereof will not be repeated here.

The thickness of the electron blocking film 1003 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 1013.

The hole blocking film 1005 may be provided between the photoelectric conversion film 1004 and the upper electrode 1006. In a case in which the bias voltage is applied between the lower electrode 1002 and the upper electrode 1006, it is possible to prevent an increase in the dark current due to the injection of holes from the upper electrode 1006 into the photoelectric conversion film 1004.

The hole blocking film 1005 may be made of an electron accepting organic material.

The thickness of the hole blocking film 1005 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 1013.

In actuality, the material used for the hole blocking film 1005 may be selected according to a material forming an adjacent electrode and a material forming an adjacent photoelectric conversion film 1004. It is preferable that the material used for the hole blocking film 318 have an ionization potential (Ip) that is at least 1.3 eV higher than the work function (Wf) of the material forming the adjacent electrode and have an electron affinity (Ea) equal to or more than that of the material forming the adjacent photoelectric conversion film 1004. Materials applicable as the electron accepting organic material have been described in detail in JP-A No. 2009-32854 and thus a detailed description thereof will not be repeated here.

Figure 30:
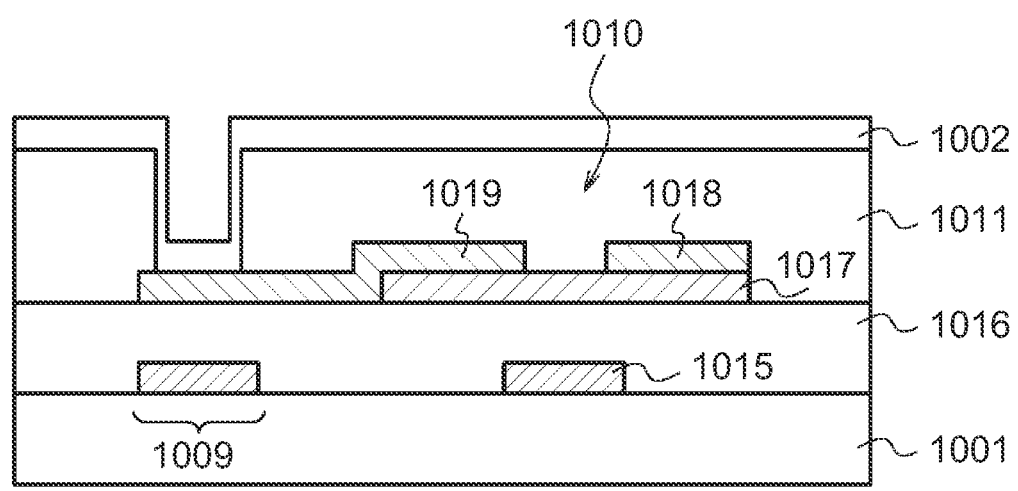
FIG. 30 is a lateral cross-sectional view illustrating the schematic configuration of a signal output unit of one pixel of the radiation detector according to the second exemplary embodiment.

In a case in which the bias voltage is set such that holes are moved to the upper electrode 1006 and electrons are moved to the lower electrode 1002, among the charges generated in the photoelectric conversion film 1004, the positions of the electron blocking film 1003 and the hole blocking film 1005 may be reversed. In addition, neither the electron blocking film 1003 nor the hole blocking film 1005 may be provided. When either the electron blocking film 1003 or the hole blocking film 1005 is provided, it is possible to a certain extent to obtain the effect of preventing the dark current. The signal output unit 1014 is provided on the surface of the substrate 1001 below the lower electrode 1002 of each pixel. FIG. 30 is a schematic diagram illustrating the structure of the signal output unit 1014.

As illustrated in FIG. 30, the signal output unit 1014 according to this exemplary embodiment has a capacitor 1009 that accumulates the charge moved to the lower electrode 1002 to correspond to the lower electrode 1002 and a field effect thin film transistor (hereinafter, simply referred to as TFT) 1010 that converts the charge accumulated in the capacitor 1009 into an electric signal and outputs the electric signal. A region in which the capacitor 1009 and the TFT 1010 are formed has a portion that overlaps the lower electrode 1002 in a plan view. By this configuration, the signal output unit 1014 and the sensor unit 1013 in each pixel overlap each other in the thickness direction. In order to minimize the plane area of the radiation detector 1020 (pixel), it is preferable that the region in which the storage capacitor 1009 and the TFT 1010 are formed be completely covered with the lower electrode 1002.

The capacitor 1009 is electrically connected to the corresponding lower electrode 1002 through a conductive line that is formed so as to pass through the insulating film 1011 provided between the substrate 1001 and the lower electrode 1002. In this way, the charge captured by the lower electrode 1002 can be moved to the capacitor 1009.

The TFT 1010 is formed by laminating a gate electrode 1015, a gate insulating film 1016, and an active layer (channel layer) 1017 and providing a source electrode 1018 and a drain electrode 1019 on the active layer 1017 with a predetermined gap therebetween.

The active layer 1017 may be made of, for example, amorphous silicon, an amorphous oxide, an organic semiconductor material, or carbon nanotubes. The material forming the active layer 1017 is not limited thereto.

An oxide (for example, an In—O-based oxide) including at least one of In, Ga, and Zn is preferable as the amorphous oxide that can form the active layer 1017. An oxide (for example, an In—Zn—O-based oxide, an In—Ga—O-based oxide, or a Ga—Zn—O-based oxide) including at least two of In, Ga, and Zn is more preferable as the amorphous oxide. An oxide including In, Ga, and Zn is most preferable as the amorphous oxide. As an In—Ga—Zn—O-based amorphous oxide, an amorphous oxide having a composition represented by $InGaO_3(ZnO)_m$ (m is a natural number smaller than 6) in a crystalline state is preferable, and $InGaZnO_4$ is more preferable.

A phthalocyanine compound, pentacene, or vanadyl phthalocyanine may be given as an example of the organic semiconductor material that can form the active layer 1017, but the organic semiconductor material is not limited thereto. The configuration of the phthalocyanine compound has been described in detail in JP-A No. 2009-212389 and thus a detailed description thereof will not be repeated here. The disclosure of JP-A No. 2009-212389 is incorporated by reference herein.

When the active layer 1017 of the TFT 1010 is made of an amorphous oxide, an organic semiconductor material, or carbon nanotubes, radiation, such as X-rays, is not absorbed. Even though the radiation is absorbed, a very small amount of radiation is absorbed. Therefore, it is possible to effectively prevent the generation of noise in the signal output unit 1014.

In a case in which the active layer 1017 is made of carbon nanotubes, it is possible to improve the switching speed of the TFT 1010 and form the TFT 1010 with low light absorptance in the visible light range. In addition, in a case in which the active layer 1017 is made of carbon nanotubes, even though a very small amount of metallic impurities is mixed with the active layer 324, the performance of the TFT 1010 is significantly reduced. Therefore, it is necessary to separate and extract carbon nanotubes with very high purity using, for example, centrifugal separation and form the active layer with the carbon nanotube.

All of the amorphous oxide forming the active layer 1017 of the TFT 1010, the organic semiconductor material, the carbon nanotubes, and the organic photoelectric conversion material forming the photoelectric conversion film 4 can be used to form a film at a low temperature. The substrate 1010 is not limited to a substrate with high heat resistance, such as a semiconductor substrate, a quartz substrate, or a glass substrate, but a flexible substrate, such as a plastic substrate, an aramid substrate, or a bio-nanofiber substrate may be used as the substrate 1010. Specifically, for example, a flexible substrate made of the following materials may be used: polyester, such as polyethylene terephthalate, polybutylene phthalate, or polyethylene naphthalate, polystyrene, polycarbonate, polyether sulfone, polyarylate, polyimide, polycycloolefin, norbornene resin, and poly(chlorotrifluoroethylene). When the flexible substrate made of plastic is used, it is possible to reduce the weight of the substrate. For example, this configuration has an advantage in portability.

In addition, for example, an insulating layer for ensuring an insulating property, a gas barrier layer for preventing the penetration of water or oxygen, and an undercoating layer for improving flatness or the adhesion of, for example, the electrode may be provided on the substrate 1001.

Since aramid can be applied to a high-temperature processing of 200 degrees or more, a transparent electrode material can be cured at a high temperature to have low resistance, and the aramid can respond to the automatic mounting of a driver IC including a solder reflow processing. In addition, the thermal expansion coefficient of aramid is close to that of ITO (indium tin oxide) or a glass substrate. Therefore, after an aramid substrate is manufactured, the warping of the aramid substrate is small and the aramid substrate is less likely to be cracked. In addition, aramid is capable of forming a substrate thinner than, for example, a glass substrate. Aramid may be laminated on a super-thin glass substrate to form the substrate.

The bio-nanofiber is a composite of a cellulose microfibril bundle generated by bacteria (Acetobacter Xylinum) (bacterial cellulose) and a transparent resin. The cellulose microfibril bundle has a width of 50 nm, a size of one-tenth of the visible light wavelength, high strength, high elasticity, and a low thermal expansion coefficient. A transparent resin, such as an acrylic resin or an epoxy resin, is impregnated into the bacterial cellulose and is then cured to obtain bio-nanofiber that has a light transmittance of about 90% at a wavelength of 500 nm while including 60 to 70% of fiber. The bio-nanofiber has a low thermal expansion coefficient (3 to 7 ppm) equal to that of a silicon crystal, strength (460 MPa) similar to that of iron, high elasticity (30 GPa), and flexibility. Therefore, the bio-nanofiber can form the substrate 1001 thinner than, for example, a glass substrate.

In this exemplary embodiment, the signal output unit 1014, the sensor unit 1013, and the transparent insulating film 1007 are sequentially formed on the TFT substrate 1030 and the scintillator 1008 is bonded to the TFT substrate 1030 by an adhesive resin with low light absorptance, thereby forming the radiation detector 1020.

Figure 31:
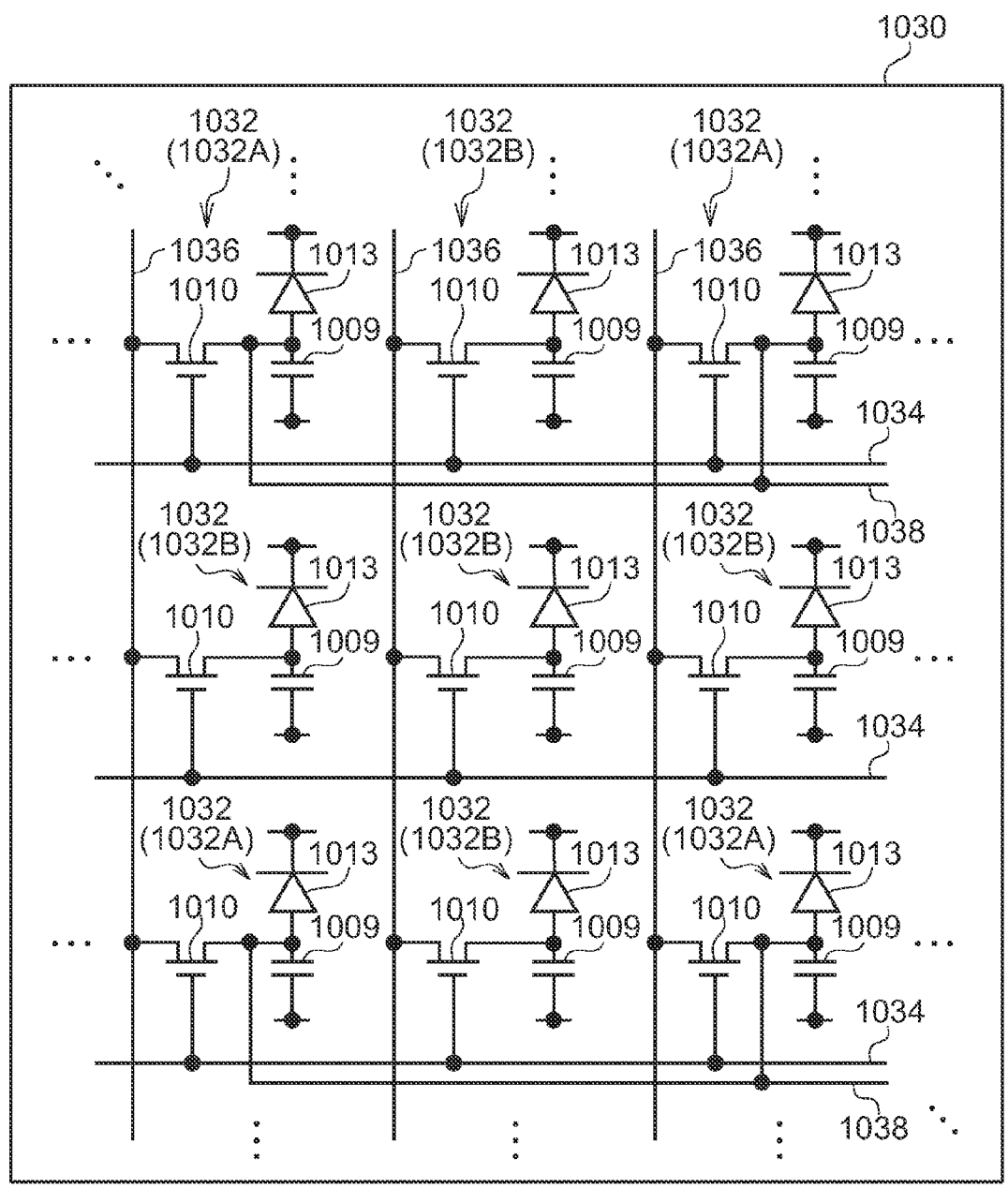
FIG. 31 is a plan view illustrating the configuration of the radiation detector according to the second exemplary embodiment.

As illustrated in FIG. 31, in the TFT substrate 1030, the pixels 1032 that include the sensor unit 1013, the capacitor 1009, and the TFT 1010 are provided to be two-dimensionally disposed in a constant direction (row direction of FIG. 31) and a direction (column direction of FIG. 31) crossing the constant direction.

In the radiation detector 1020, plural gate lines 1034 that extend in the constant direction (row direction) and turn on/off the TFTs 1010 and plural data lines 1036 that extend in the crossing direction (column direction) and read the charge through the TFTs 1010 in an ON state are provided.

The radiation detector 1020 is formed in a shape that is flat and has four sides at the outer edge in plan view, specifically, a rectangular shape.

In the radiation detector 1020 according to this exemplary embodiment, a part of the pixels 1032 is used to detect an irradiation state of the radiation, and radiation images are captured by the remaining pixels 1032. Hereinafter, the pixels 1032 to detect the irradiation state of the radiation are called radiation detecting pixels 1032A and the remaining pixels 1032 are called radiation image acquiring pixels 1032B.

In the radiation detector 1020 according to this exemplary embodiment, since the radiation images are captured by the radiation image acquiring pixels 1032B other than the radiation detecting pixels 1032A in the pixels 1032, pixel information of the radiation images at the arrangement position of the radiation detecting pixels 1032A cannot be obtained. For this reason, in this exemplary embodiment, the radiation detecting pixels 1032A are disposed to disperse, and the pixel information of the radiation images at the arrangement positions of the radiation detecting pixels 1032A is generated by performing interpolation using pixel information obtained by the radiation image acquiring pixels 1032B positioned around the radiation detecting pixels 1032A.

In the radiation detector 1020 according to this exemplary embodiment, as shown in FIG. 31, a direct read line 1038 that is connected to a connection portion of the capacitor 1009 and the TFT 1010 in the radiation detecting pixel 1032A and directly reads the charge that is accumulated in the capacitor 1009 extends in the constant direction (row direction). In the radiation detector 1020 according to this exemplary embodiment, one direct read line 1038 is allocated to the plural radiation detecting pixels 1032A arranged in the constant direction, and the connection portion of the capacitor 1009 and the TFT 1010 in the plural radiation detecting pixel 1032A is connected to the common (single) direct read line 1038.

Figure 32:
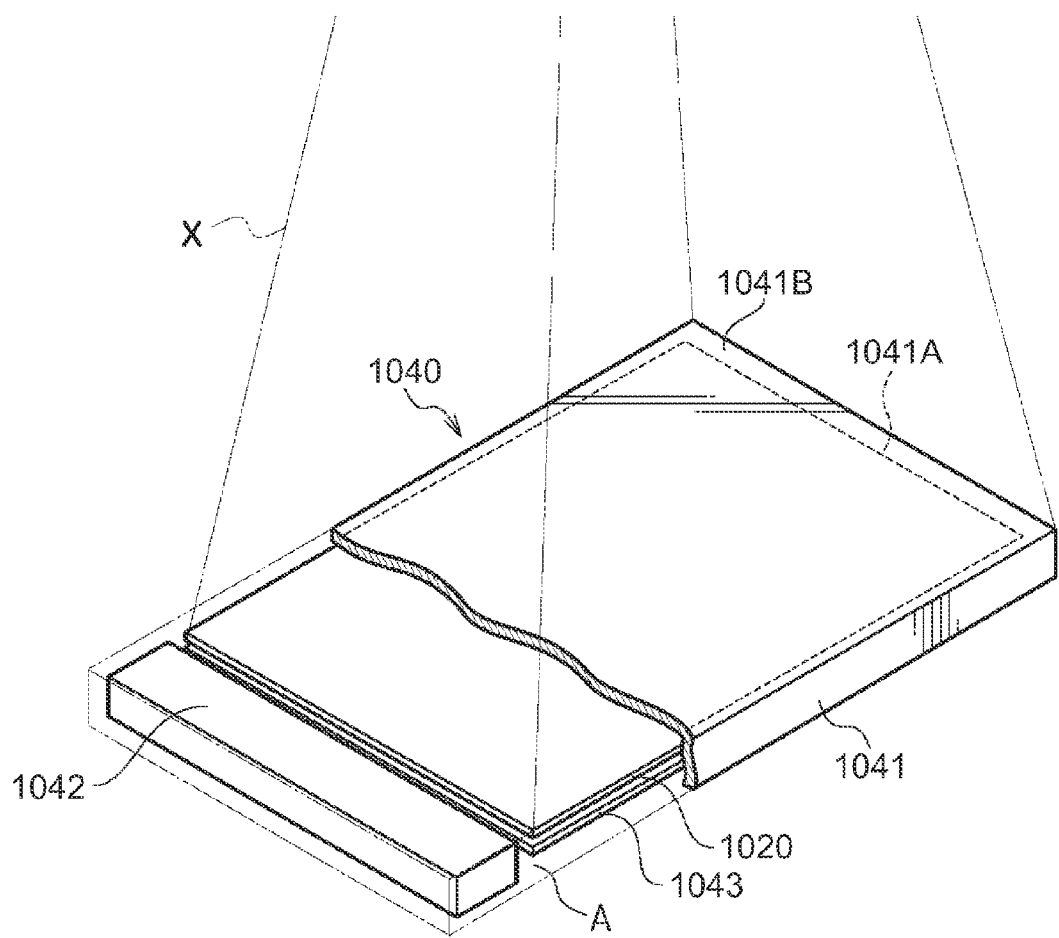
FIG. 32 is a perspective view illustrating the configuration of an electronic cassette according to the second exemplary embodiment.

Next, the configuration of the electronic cassette 1040 according to this exemplary embodiment will be described. FIG. 32 is a perspective view illustrating the configuration of the electronic cassette 1040 according to the second exemplary embodiment.

As illustrated in FIG. 32, the electronic cassette 1040 according to this exemplary embodiment includes a casing 1041 that is formed of a material transmitting the radiation, and is configured to have a waterproof property and a sealing property. In a case in which the electronic cassette 1040 is used in an operating room, blood or various germs may be attached to the electronic cassette 1040. Therefore, by configuring the electronic cassette 1040 to have a waterproof property and a sealing property and performing antiseptic washing the electronic cassette 1040 on the according to necessity, one electronic cassette 1040 may be repetitively used.

In the casing 1041, a space A that stores various components is formed. In the space A, the radiation detector 1020 that detects the radiation X transmitted through the subject from the side of the irradiation surface of the casing 1041 where the radiation X is irradiated, and a lead plate 1043 that absorbs back scattered rays of the radiation X are sequentially disposed.

In the electronic cassette 1040 according to this exemplary embodiment, a region of one flat surface of the casing 1041 that corresponds to the arrangement position becomes an image capturing region with a rectangular shape that can detect the radiation. A surface that has the image capturing region 1041A of the casing 1041 becomes a ceiling plate 1041B in the electronic cassette 1040. In the electronic cassette 1040 according to this exemplary embodiment, the radiation detector 1020 is disposed such that the TFT substrate 1030 becomes the ceiling plate 1041B, and is bonded to the inner surface (surface of the ceiling plate 1041B opposite to the surface on which the radiation is incident) of the ceiling plate 1041B in the casing 1041.

As illustrated in FIG. 32, on the side of one end of an inner part of the casing 1041, a case 1042 that stores a cassette control unit 1058 or a power supply unit (refer to FIG. 34) to be described below at the position (out of a range of the image capturing region 1041A) not overlapping the radiation detector 1020 is disposed.

The casing 1041 is made of carbon fiber, aluminum, magnesium, bionanofiber (cellulose microfibril), or composite material, to decrease the weight of the entire electronic cassette 1040.

As the composite material, for example, a reinforced fiber resin is used. Examples of the reinforced fiber resin include carbon and cellulose. Specifically, as the composite material, carbon fiber reinforced plastic (CFRP), a structure in which a foam material is sandwiched by the CFRP, or a structure where the CFRP is coated on a surface of the foam material is used. In this exemplary embodiment, the structure in which the foam material is sandwiched by the CFRP is used. Thereby, as compared with the case where the casing 1041 is configured in a carbon simple substance, strength (rigidity) of the casing 1041 can be heightened.

Figure 33:
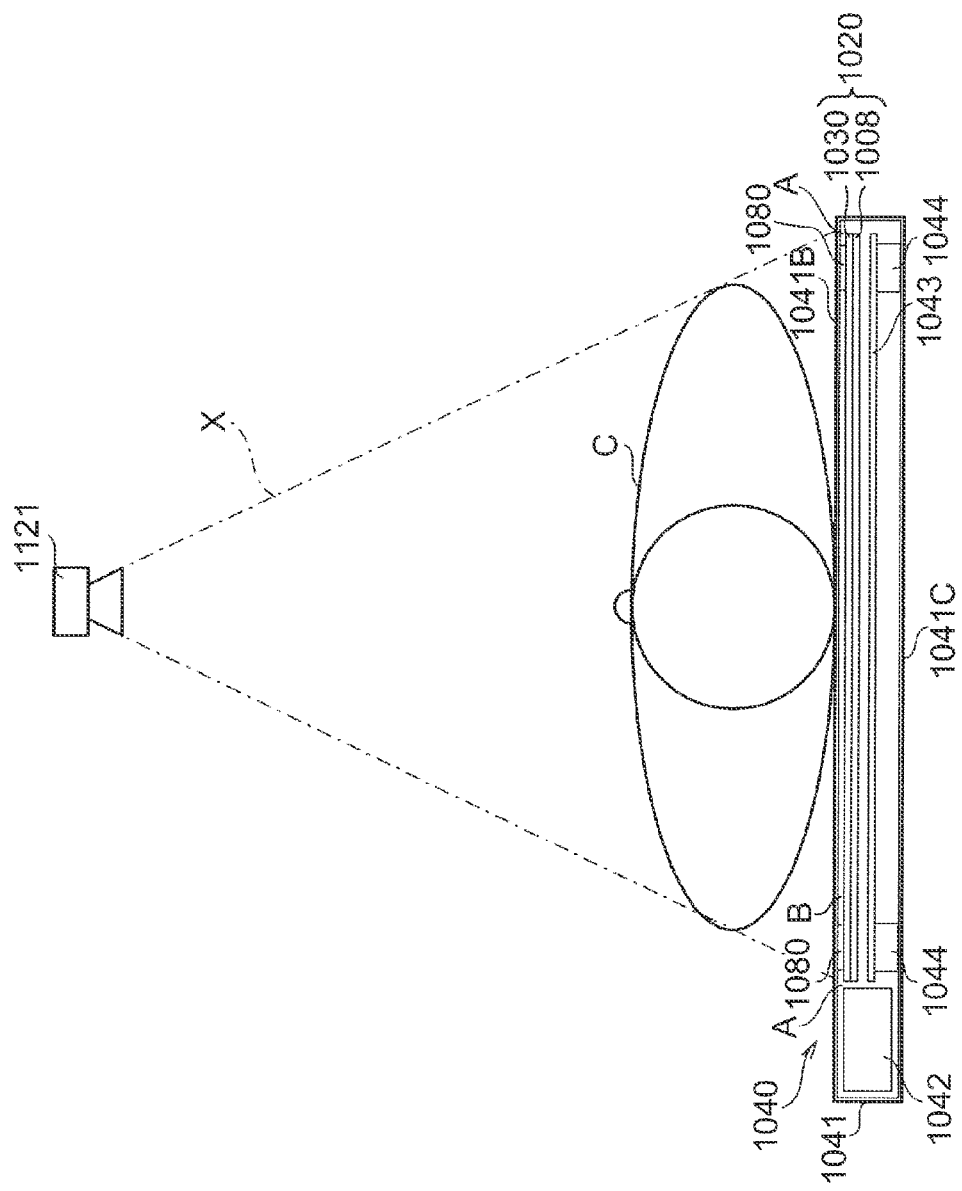
FIG. 33 is a lateral cross-sectional view illustrating the configuration of the electronic cassette according to the second exemplary embodiment.

As illustrated in FIG. 33, in the casing 1041, a support object 1044 that is disposed on an inner surface of a back surface portion 1041C that faces the ceiling plate 1041B, and the radiation detector 1020 and the lead plate 1043 are sequentially disposed in the irradiation direction of the radiation X, between the support object 1044 and the ceiling plate 1041. The support object 1044 is made of the foam material, in terms of reduction in the weight and removal of a dimension deviation, and supports the lead plate 1043.

As illustrated in FIG. 33, on the inner surface of the ceiling plate 1041B, an adhesive member 1080 that bonds the TFT substrate 1030 of the radiation detector 1020 to be separated is provided. As the adhesive member 1080, for example, a both-sided tape is used. In this case, the both-sided tape is formed such that the adhesive strength of one adhesive surface is stronger than the adhesive strength of the other adhesive surface.

Specifically, the surface having the weak adhesive strength (weak adhesive surface) is set to have 1.0 N/cm at 180° peeling adhesive strength. The surface having the strong adhesive strength (strong adhesive surface) contacts the ceiling plate 1041B and the weak adhesive surface contacts the TFT substrate 1030. Thereby, the thickness of the electronic cassette 1040 can be decreased, as compared with the case where the radiation detector 1020 is fixed to the ceiling plate 1041B by affixing method such as a screw. Even though the ceiling plate 1041B is deformed due to a shock or a load, the radiation detector 1020 follows deformation of the ceiling plate 1041B that has high rigidity. Therefore, only large curvature (moderate curve) is generated and the radiation detector 1020 is less likely to be damaged with local low curvature. The radiation detector 1020 contributes to improving the rigidity of the ceiling plate 1041B.

As such, in the electronic cassette 1040 according to this exemplary embodiment, since the radiation detector 1020 is bonded to the inner portion of the ceiling plate 1041B of the casing 1041, the casing 1041 is divided into two parts at the side of the ceiling plate 1041B and the side of the back surface portion 1041C. When the radiation detector 1020 is bonded to the ceiling plate 1041B or the radiation detector 1020 is separated from the ceiling plate 1041B, the casing 1041 is divided into two parts at the side of the ceiling plate 1041B and the side of the back surface portion 1041C.

In this exemplary embodiment, adhesion of the radiation detector 1020 with respect to the ceiling plate 1041B may be performed in a clean room. This reason is as follows. In a case in which a foreign material such as a metal piece absorbing the radiation is mixed between the radiation detector 1020 and the ceiling plate 1041B, the foreign material can be removed by separating the radiation detector 1020 from the ceiling plate 1041B.

Next, the configuration of a main portion of an electric system of the image capturing system 1104 according to this exemplary embodiment will be described with reference to FIG. 34.

Figure 34:
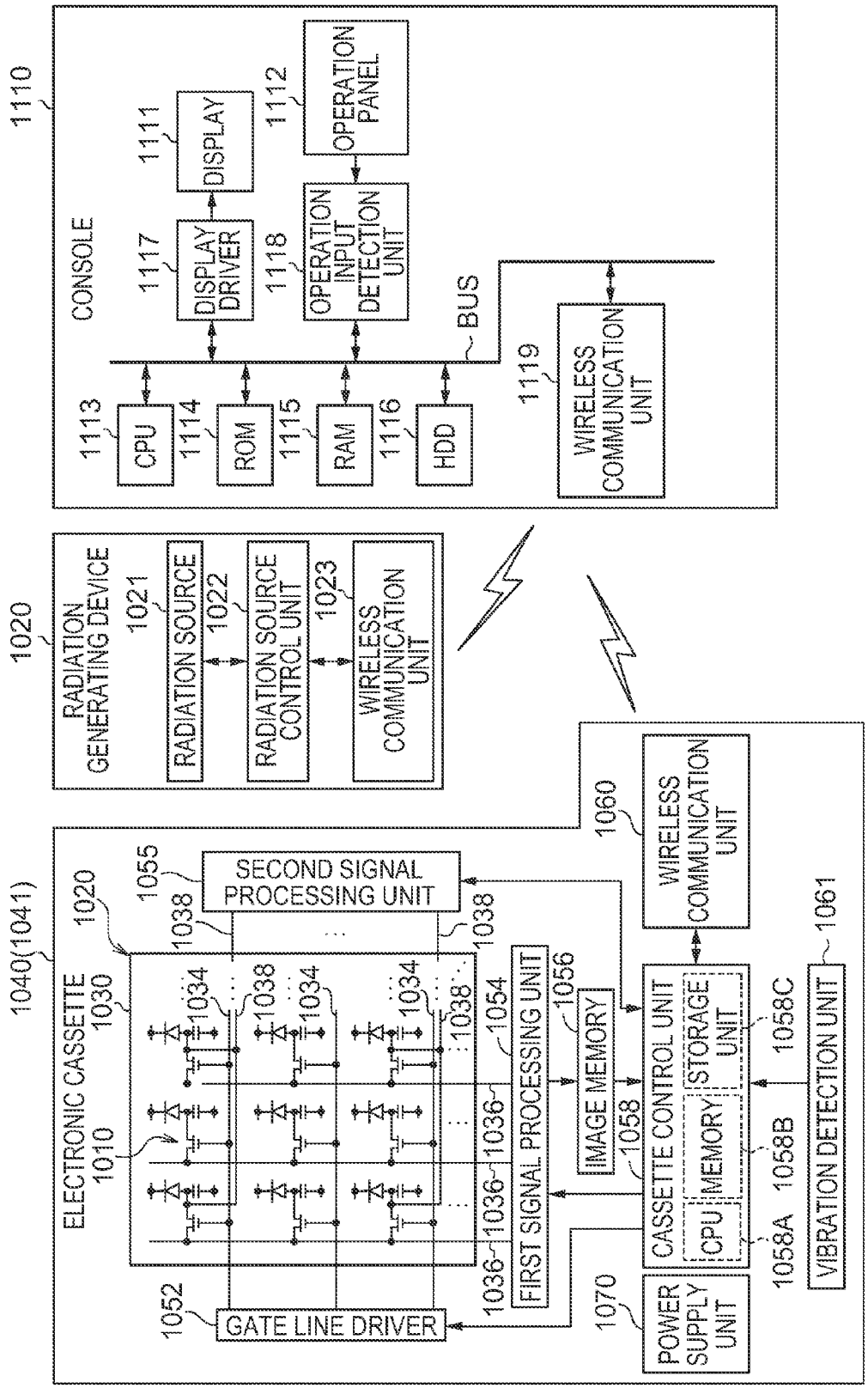
FIG. 34 is a block diagram illustrating the configuration of a main portion of an electric system of a radiation image capturing system according to the second exemplary embodiment.

As illustrated in FIG. 34, in the radiation detector 1020 that is incorporated in the electronic cassette 1040, a gate line driver 1052 is disposed on one side of two adjacent sides, and a first signal processing unit 1054 is disposed on the other side. Each of the gate lines 1034 of the TFT substrate 1030 is connected to the gate line driver 1052 and each of the data lines 1036 of the TFT substrate 1030 is connected to the first signal processing unit 1054.

The casing 1041 includes an image memory 1056, a cassette control unit 1058, and a wireless communication unit 1060 provided therein.

Each of the TFTs 1010 of the TFT substrate 1030 is sequentially turned on in a row unit by the signal supplied from the gate line driver 1052 through the gate line 1034. The charge that is read by the turned-on TFT 1010 is transmitted as an electric signal through the data line 36 and is input to the first signal processing unit 1054. Thereby, the charge is sequentially read in a row unit and a two-dimensional radiation image can be obtained.

Although not illustrated in the drawings, the first signal processing unit 1054 includes an amplifying circuit that amplifies an input electric signal and a sample-and-hold circuit, for each data line 1036. The electric signal that is transmitted through each data line 1036 is amplified by the amplifying circuit and is held in the sample-and-hold circuit. To the output side of the sample-and-hold circuit, a multiplexer and an analog/digital (A/D) converter are sequentially connected. The electric signal that is held in each sample-and-hold circuit is sequentially (serially) input to the multiplexer and is converted into digital image data by the A/D converter.

The image memory 1056 is connected to the first signal processing unit 1054 and the image data that is output form the A/D converter of the first signal processing unit 1054 is sequentially stored in the image memory 1056. The image memory 1056 has a storage capacity that can store image data of the predetermined amount. The image data that is obtained by image capturing is sequentially stored in the image memory 1056, whenever a radiation image is captured.

The image memory 1056 is connected to the cassette control unit 1058. The cassette control unit 1058 is configured to include a microcomputer. The cassette control unit 1058 includes a central processing unit (CPU) 1058A, a memory 1058B including a read only memory (ROM) and a random access memory (RAM), and a nonvolatile storage unit 1058C including a flash memory, and wholly controls the electronic cassette 1040.

The wireless communication unit 1060 is connected to the cassette control unit 1058. The wireless communication unit 1060 corresponds to the wireless local area network (LAN) standard exemplified by IEEE (Institute of Electrical and Electronics Engineers) 802.11a/b/g. The wireless communication section 1060 controls an exchange of various types of information with external devices by wireless communication. The cassette control unit 1058 can communicate wirelessly with the console 1110 which performs control relating to capturing of a radiation image, through the wireless communication section 1060, and can exchange various types of information with the console 1110. The disclose of the above standard is incorporated by reference herein.

In the electronic cassette 1040, the second signal processing unit 1055 is disposed on the side opposite to the gate line driver 1052 with the TFT substrate 1030 interposed therebetween, and each direct read line 1038 of the TFT substrate 1030 is connected to the second signal processing unit 1055.

The second signal processing unit 1055 includes an amplifier and an A/D converter that are provided for each direct read line 1038, and is connected to the cassette control unit 1058. Under the control from the cassette control unit 1058, the second signal processing unit 1055 performs sampling on each direct read signal 1038 with a predetermined cycle, converts an electric signal transmitted through each direct read line 1038 into digital data, and sequentially outputs the converted digital data to the cassette control unit 1058.

In the electronic cassette 1040, a vibration detection unit 1061 to detect vibration is provided. The vibration detection unit 1061 is connected to the cassette control unit 1058 and the cassette control unit 1058 can grasp a vibration state, on the basis of a detection state by the vibration detection unit 1061.

In the electronic cassette 1040, a power supply unit 1070 is provided. The various circuits or elements (the gate line driver 1052, the first signal processing unit 1054, the second signal processing unit 1055, the image memory 1056, the wireless communication unit 1060, the vibration detection unit 1061, the microcomputer functioning as the cassette control unit 1058, and the like) are operated by power supplied from the power supply unit 1070. The power supply unit 1070 incorporates a battery (a chargeable secondary battery) for the portability of the electronic cassette 1040, and a power is supplied from the charged battery to the various circuits and elements. In FIG. 34, wiring lines that connect the power supply unit 1070 and the various circuits or elements are omitted.

Meanwhile, the console 1110 is configured as a server/computer. The console 1110 includes a display 1111 that displays an operation menu, a captured radiation image, or the like and an operation panel 1112 that has plural keys and receives various types of information or operation instructions.

The console 1110 according to this exemplary embodiment includes a CPU 1113 that operates the entire device, a ROM 1114 that previously stores various programs including a control program, a RAM 1115 that temporarily stores various types of data, a hard disk drive (HDD) 1116 that stores and holds various types of data, a display driver 1117 that controls display of various types of information on the display 1111, and an operation input detection unit 1118 that detects an operation state with respect to the operation panel 1112. The console 1110 includes a wireless communication unit 1119 that exchanges various types of information such as exposure conditions to be described below, through the wireless communication, and exchanges various types of information such as image data with the electronic cassette 1040.

The CPU 1113, the ROM 1114, the RAM 1115, the HDD 1116, the display driver 1117, the operation input detection unit 1118, and the wireless communication unit 1119 are mutually connected through a system bus BUS. Therefore, the CPU 1113 can have access to the ROM 1114, the RAM 1115, and the HDD 1116, and can control display of various types of information with respect to the display 1111 through the display driver 1117 and an exchange of various types of information with the radiation generating device 1120 and the electronic cassette 1040 through the wireless communication unit 1119. The CPU 1113 can grasp an operation state of the user with respect to the operation panel 1112 through the operation input detection unit 1118.

The radiation generating unit 1120 includes a radiation source 1121, a wireless communication unit 1123 that exchanges various types of information such as exposure conditions with the console 1110, and a radiation source control unit 1122 that controls the radiation source 1121, on the basis of the received exposure conditions.

The radiation source control unit 1122 is configured to include a microcomputer and stores the received exposure conditions. The exposure conditions that are received from the console 1110 include information, such as a tube voltage and a tube current. The radiation source control unit 1122 makes the radiation source 1121 irradiate the radiation X, on the basis of the received exposure conditions.

Next, a function of the image capturing system 1104 according to this exemplary embodiment will be described.

In a case in which a radiation image is captured, the radiographer inputs image capturing conditions, such as the image capturing part, the image capturing posture, and holding state information indicating whether an image is captured in a state in which the electronic cassette 1040 is held by the holding portion 1162 of the rack 1160 or the holding portion 1166 of the bed 1164 and whether an image is captured in a state in which the electronic cassette 1040 is not held by the holding portion, to the console 1110 through the operation panel 1112, and inputs the exposure conditions, such as the tube voltage, the tube current, and the irradiation period. If the image capturing conditions and the exposure conditions are input, the console 1110 transmits the input image capturing conditions and exposure conditions to the electronic cassette 1040 through the wireless communication unit 1119 and transmits the exposure conditions to the radiation generating device 1120 through the wireless communication unit 1119.

If the radiation source control unit 1122 of the radiation generating device 1120 receives the exposure conditions from the console 1110, the radiation source control unit 1122 stores the received exposure conditions and performs an exposure preparation under the exposure conditions.

If the cassette control unit 1058 of the electronic cassette 1040 receives the image capturing conditions and the exposure conditions from the console 1110, the cassette control unit 1058 stores the received image capturing conditions and exposure conditions in the storage unit 1058C.

When the image capturing posture is the standing posture or the lying posture, the radiographer holds the electronic cassette 1040 by the holding portion 1162 of the corresponding rack 1160 or the corresponding holding portion 1166 of the bed 1164, positions the radiation source 1121 at the corresponding position, and then positions the subject at the predetermined image capturing position. Meanwhile, when radiation images are captured with respect to the arms, the legs, and the like to be the image capturing parts in a state in which the electronic cassette 1040 is not held by the holding portion, the radiographer positions the subject, the electronic cassette 1040, and the radiation source 1121 in a state in which the radiation images can be captured with respect to the image capturing parts.

If the image capturing preparation is completed, the radiographer performs an image capturing instruction operation to instruct image capturing, with respect to the operation panel 1112 of the console 1110.

If the image capturing instruction operation is performed with respect to the operation panel 1112, the console 1110 transmits instruction information to instruct an exposure start, to the radiation generating device 1120 and the electronic cassette 1040 through the wireless communication unit 1119.

In response to that, the radiation source 1121 emits the radiation X with the tube voltage and the tube current according to the exposure conditions received from the console 1110 by the radiation generating device 1120, during the irradiation period. The radiation X that is emitted from the radiation source 1121 reaches the electronic cassette 1040 after being transmitted through the subject. Thereby, in each pixel 1032 of the radiation detector 1020, the charge is generated.

In the electronic cassette 1040 according to this exemplary embodiment, the second signal processing unit 1055 samples an electric signal that is output from the radiation detecting pixel 1032A to each direct read line 1038, converts the electric signal into digital data, detects a start of irradiation of radiation on the basis of the converted digital data, and starts an image capturing operation of a radiation image at a timing when irradiation of the radiation starts. That is, the electronic cassette 1040 detects the irradiation of the radiation and starts the image capturing operation. Thereby, the image capturing system 1104 according to this exemplary embodiment can exchange information on the start of irradiation of radiation with the console 1110 and/or the radiation generating device 1120 and the electronic cassette 1040 and capture a radiation image without synchronizing a radiation irradiation operation from the radiation generating device 1120 and an image capturing operation in the electronic cassette 1140.

The electronic cassette 1040 detects the start of irradiation of radiation. Therefore, in a case in which an electric signal output to each direct read line 1038 is sampled by the second signal processing unit 1055 as needed, the power consumption increases.

In the electronic cassette 1040 according to this exemplary embodiment, a vibration state is grasped on the basis of the detection state by the vibration detection unit 1061. If the vibration is settled, the positioning of the electronic cassette 1040 is completed, it is determined that the image capturing preparation is completed, and sampling of each direct read line 1038 by the second signal processing unit 1055 starts.

The vibration detection unit 1061 may be configured using any one of an acceleration sensor, a gyro sensor, a strain gauge, a gravity sensor, a geomagnetism sensor, and the like that can detect the vibration.

If the acceleration is not detected or is settled within a constant value, the acceleration sensor and the gyro sensor can determine that the vibration is settled and the positioning or the image capturing preparation is completed. If the strain is removed or stabilized, the strain gauge can determine that the vibration is settled and the positioning or the image capturing preparation is completed. When the directions of the gravity and the geomagnetism are detected, if the directions of the gravity and the geomagnetism are stabilized, the gravity sensor or the geomagnetism sensor can determine that the vibration is settled and the positioning or the image capturing preparation is completed.

Figure 35:
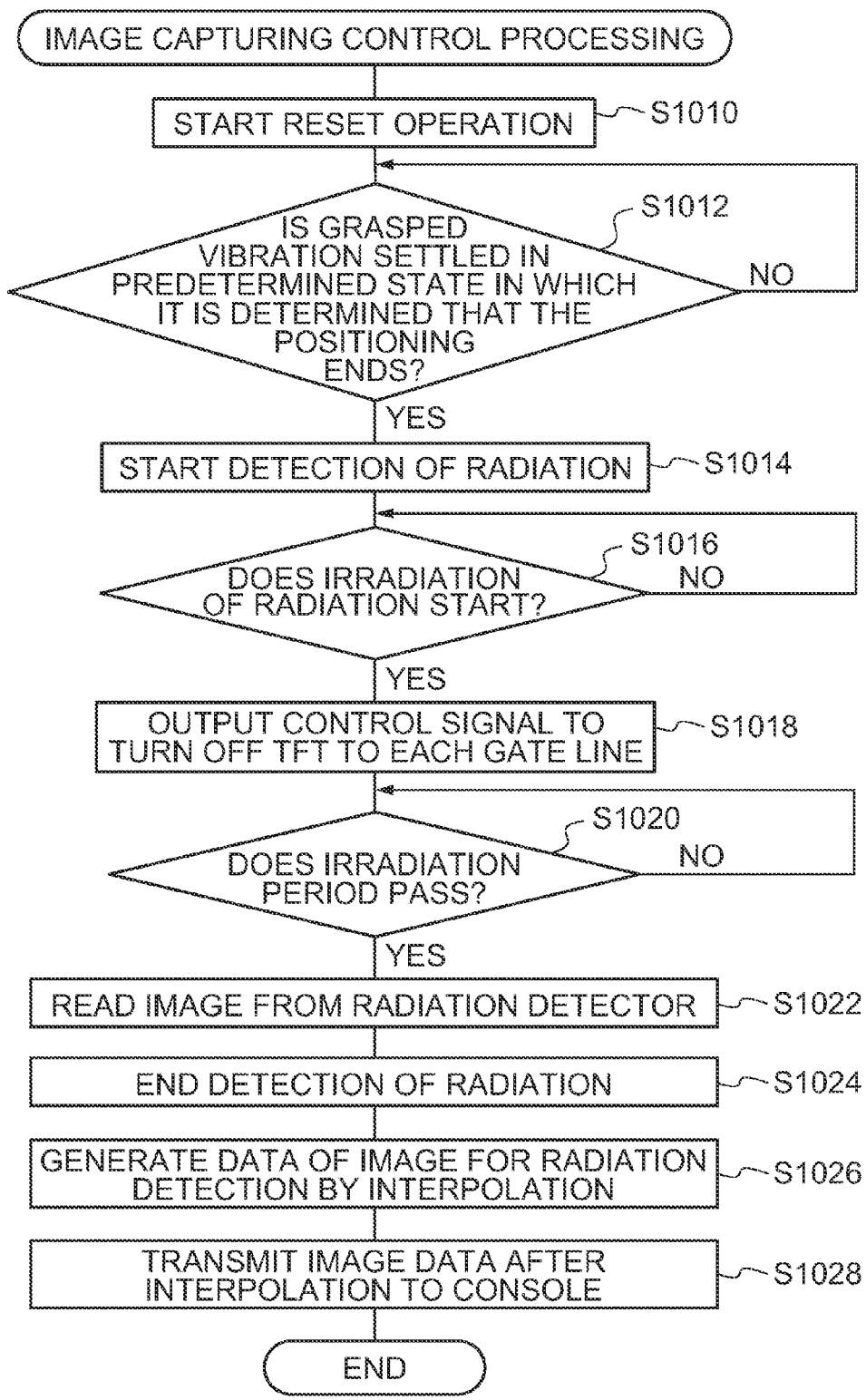
FIG. 35 is a flowchart illustrating a flow of a processing of an image capturing control processing program according to the second exemplary embodiment.

FIG. 35 is a flowchart illustrating a flow of a processing of an image capturing control processing program that is executed by a CPU 1058A of a cassette control unit 1058, when the image capturing conditions and the exposure conditions are received from the console 1110. The image capturing control processing program is previously stored in a predetermined region of a memory 1058B (ROM).

In step S1010 of FIG. 35, a reset operation in which the gate line driver 1052 is controlled and a control signal to turn on the TFTs 1010 is sequentially output from the gate line driver 1052 to each gate line 1034 starts.

Thereby, in the radiation detector 1020, the charge that is accumulated each one line sequentially in the capacitor 1009 of each pixel 1032 is output as an electric signal to each data line 1036, and the charge that is accumulated in the capacitor 1009 of each pixel 1032 by the dark current is removed. This operation is repeated.

In next step S1012, it is determined whether the vibration grasped on the basis of the detection state by the vibration detection unit 1061 is settled in a predetermined state in which it is determined that the positioning ends. If the determination result is YES, the processing proceeds to step S1014. If the determination result is NO, the processing proceeds to step S1012 again.

In a case in which an image is captured in a state in which the electronic cassette 1040 is held by the holding portion 1162 of the rack 1160 or the holding portion 166 of the bed 1164 and in a case in which an image is captured in a state in which the electronic cassette 1040 is not held by the holding portion, the magnitude of the vibration that is detected by the vibration detection unit 1061 by the positioning of the subject or the electronic cassette 1040 is different. The magnitude of the vibration that is detected by the vibration detection unit 1061 by the positioning in the state in which the electronic cassette is held by the holding portion is smaller than that in the state in which the electronic cassette is not held by the holding portion.

For this reason, conditions of a state in which it is determined that the positioning is completed may be changed by determining whether an image is captured in a state in which the electronic cassette 1040 is held by the holding portion or in a state in which the electronic cassette 1040 is not held by the holding portion, on the basis of holding state information included in the image capturing conditions.

For example, in a case in which it is determined that the positioning is completed when the change amount of a vibration value detected by the vibration detection unit 1061 for predetermined time (for example, 5 sec.) becomes a predetermined threshold value or less, the threshold value change when an image is captured in the state in which the electronic cassette 1040 is not held by the holding portion may be smaller than the threshold value change when an image is captured in the state in which the electronic cassette 1040 is held by the holding portion.

In next step S1014, sampling of each direct read line 1038 by the second signal processing unit 1055 starts.

Thereby, the second signal processing unit 1055 samples each direct read line 1038 with a predetermined cycle, converts the electric signal transmitted to each direct read line 1038 into digital data, and sequentially outputs the converted digital data to the cassette control unit 1058.

In next step S1016, each value of the digital data of each direct read line 1038 that is input from the second signal processing unit 1055 is compared with a predetermined radiation irradiation detecting threshold value, and the start of irradiation of radiation is detected according to whether a value of certain digital data becomes equal to or more than the radiation irradiation detecting threshold value. If the value of the certain digital data becomes equal to or more than the radiation irradiation detecting threshold value, it is determined that the irradiation of the radiation starts, and the processing proceeds to step S1018. If values of all digital data are less than the radiation irradiation detecting threshold value, the processing proceeds to step S1016 again and a waiting state of the start of irradiation of radiation is maintained.

In next step S1018, the gate line driver 1052 is controlled and a control signal to turn off the TFT 1010 of each pixel 1032 is output from the gate line driver 1052 to each gate line 1034. Thereby, the charge according to the irradiated radiation dose is accumulated in each pixel 32.

In next step S1020, it is determined whether an irradiation period shown by the exposure conditions passes from a point in time when the start of irradiation of radiation is detected in step S1016. If the determination result is YES, the processing proceeds to step S1022. If the determination result is NO, the processing proceeds to step S1020.

In next step S1022, the gate line driver 1052 is controlled and an ON signal is sequentially output from the gate line driver 1052 to each gate line 1034.

If an ON signal is input to each gate line 1034, the radiation detector 1020 sequentially turns on the TFT 1010 of each pixel 1032 connected to each gate line 1034 and the charge that is accumulated each one line sequentially in the capacitor 1009 of each pixel 1032 is output as an electric signal to each data line 1036. The electric signal that is output to each data line 1036 is converted into digital image data by the first signal processing unit 1054 and is stored in the image memory 1056. Thereby, image data that shows a radiation image based on each radiation detecting pixel 1032A of the radiation detector 1020 is stored in the image memory 1056.

In next step S1024, the sampling of each direct read line 1038 by the second signal processing unit 1055 is stopped.

In the radiation detector 1020 according to this exemplary embodiment, the radiation image acquiring pixels 1032B and radiation detecting pixels 1032A are provided. The radiation detecting pixel 1032A outputs the generated charge to the direct read line 1038. For this reason, in the radiation image that is shown by the image data, the pixel that corresponds to the radiation detecting pixel 1032A becomes a defective pixel.

In step S1026, interpolation processing is performed on the radiation image stored in the image memory 1056 and data of each pixel that corresponds to each radiation detecting pixel 1032A is generated from data of the radiation image acquiring pixel 1032B around the radiation detecting pixel 1032 by interpolation.

In next step S1028, the image data of the radiation image on which the interpolation processing is performed in step S1026 is transmitted to the console 1042 and the processing ends.

As illustrated in FIG. 33, in the electronic cassette 1040 according to this exemplary embodiment, the radiation detector 1020 is incorporated such that the radiation X is irradiated from the side of the TFT substrate 1030.

Figure 36:
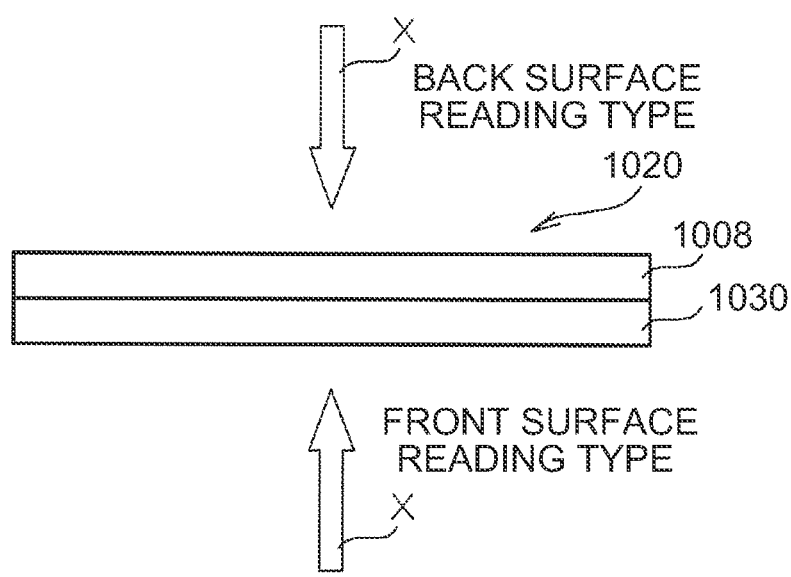
FIG. 36 is a lateral cross-sectional view illustrating a front surface reading type and a back surface reading type of a radiation image.

As illustrated in FIG. 36, in a case in which the radiation detector 1020 is configured in a so-called rear surface reading type in which the radiation is emitted from the side where the scintillator 1008 is formed and a radiation image is read by the TFT substrate 1030 provided on the side opposite to an incident surface of the radiation, high-intensity light is emitted from the side of the top surface (the side opposite to the TFT substrate 1030) of the scintillator 1008. In a case in which the radiation detector 1020 is configured in a so-called front surface reading type in which radiation is emitted from the side of the TFT substrate 1030 and a radiation image is read by the TFT substrate 1030 provided on the incident surface of the radiation, the radiation that is transmitted through the TFT substrate 1030 is incident on the scintillator 1008 and high-intensity light is emitted from the side of the scintillator 1008 close to the TFT substrate 1030. In each sensor unit 1013 provided on the TFT substrate 1030, the charge is generated by the light emitted from the scintillator 1008. Therefore, in the radiation detector 1020 of the front surface reading type, the emission position of the scintillator 1008 with respect to the TFT substrate 1030 is closer to that in the radiation detector 1020 of the rear surface reading type. As a result, in the radiation detector 1020 of the front surface reading type, the resolution of the radiation image that is obtained by image capturing is higher.

In the radiation detector 1020, the photoelectric conversion film 1004 is made of an organic photoelectric conversion material and the radiation is hardly absorbed by the photoelectric conversion film 1004. For this reason, in the radiation detector 1020 according to this exemplary embodiment, even in a case in which the radiation is transmitted through the TFT substrate 1030 in the front surface reading type, the amount of radiation absorbed by the photoelectric conversion film 1004 is small. Therefore, the reduction in sensitivity for the radiation can be suppressed. In the front surface reading type, the radiation transmits the TFT substrate 1030 and reaches the scintillator 1008. However, as such, in a case in which the photoelectric conversion film 1004 of the TFT substrate 1030 is made of an organic photoelectric conversion material, the radiation is hardly absorbed by the photoelectric conversion film 1004 and the attenuation of the radiation can be minimized. The radiation detector 1020 is suitable for the front surface reading type.

Both the amorphous oxide forming the active layer 1017 of the TFT 1010 and the organic photoelectric conversion material forming the photoelectric conversion film 1004 can be used to form a film at a low temperature. For this reason, the substrate 1001 can be made of a plastic resin, aramid, or bio-nanofiber that absorbs a small amount of radiation. Since the substrate 1001 formed in this way absorbs a small amount of radiation, the reduction in sensitivity for the radiation can be suppressed, even in a case in which the radiation is transmitted through the TFT substrate 1030 in the front surface reading type.

According to this exemplary embodiment, as illustrated in FIG. 33, the radiation detector 1020 is adhered to the ceiling plate 1041B in the casing 1041 such that the TFT substrate 1030 faces the ceiling plate 1041B. However, in a case in which the substrate 1001 is made of a plastic resin with high rigidity, aramid, or bio-nanofiber, the thickness of the ceiling plate 1041B of the casing 1041 can be decreased, because the radiation detector 1020 has high rigidity. In a case in which the substrate 1001 is made of a plastic resin with high rigidity, aramid, or bio-nanofiber, the radiation detector 1020 has flexibility. Therefore, even in a case in which an impact is applied to the image capturing region 1041A, the radiation detector 1020 is less likely to be damaged.

As described in detail above, in this exemplary embodiment, it is determined whether the image capturing preparation is completed according to whether the positioning is completed, the detection of the radiation starts if it is determined that the image capturing preparation is completed, and a radiation image is captured if the radiation is detected. Therefore, a radiographer's trouble can be saved, a power consumption can be suppressed, and a radiation image can be captured using irradiated radiation without synchronizing an irradiation timing of the radiation with the radiation generating device to irradiate the radiation.

In this exemplary embodiment, it is determined whether the positioning is completed on the basis of the vibration state. Therefore, the completion of the positioning can be detected with high precision and the radiation detection can start at an appropriate timing.

In this exemplary embodiment, the radiation detecting pixel 1032A functioning as the radiation detection unit is formed in the radiation detector 1020, and a unit for detecting the radiation does not need to be provided separately from the radiation detector 1020. Therefore, a manufacturing cost can be decreased.

In this exemplary embodiment, since the direct read line 1038 to read the accumulated charge from the plural radiation detecting pixels 1032A is provided, an irradiation state of the radiation can be detected, regardless of an image capturing operation of the radiation image. As a result, a radiation image can be captured at a high speed.

The invention is described using the exemplary embodiments. However, the technical scope of the invention is not limited to the scope described in the exemplary embodiments. Various changes and improvements may be made without departing from the spirit of the invention, and the changed and improved embodiments are also included in the technical scope of the invention.

The exemplary embodiments described above do not restrict the invention that is described in claims, and all combinations of the characteristics that are described in the exemplary embodiments are not essential in implementing the invention. The inventions of various steps are included in the exemplary embodiments described above and various inventions may be extracted by appropriately combining the plural components disclosed in the exemplary embodiments. The configuration where some components are removed may be extracted as the invention, as long as the same effect is obtained even though some components are removed from all of the components described in the exemplary embodiments.

Figure 37A:
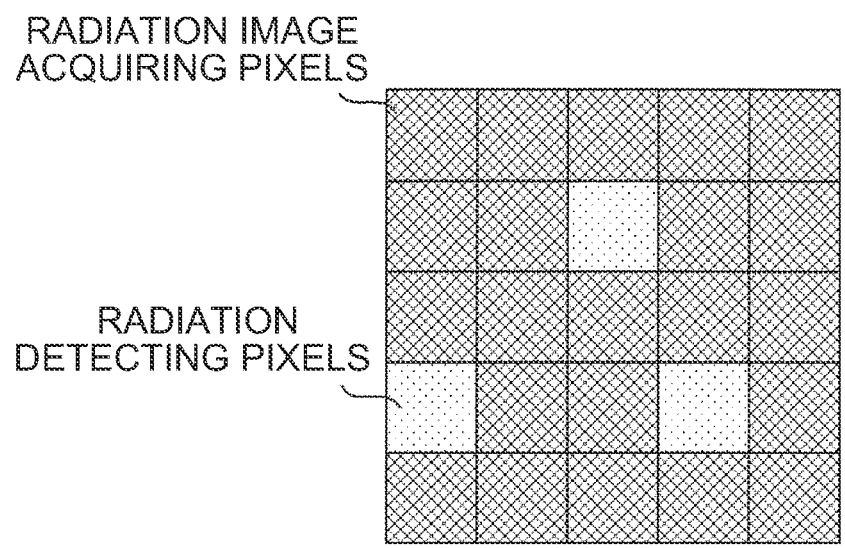
FIGS. 37A and 37B are plan views illustrating another example of the radiation detector according to the second exemplary embodiment.
Figure 37B:
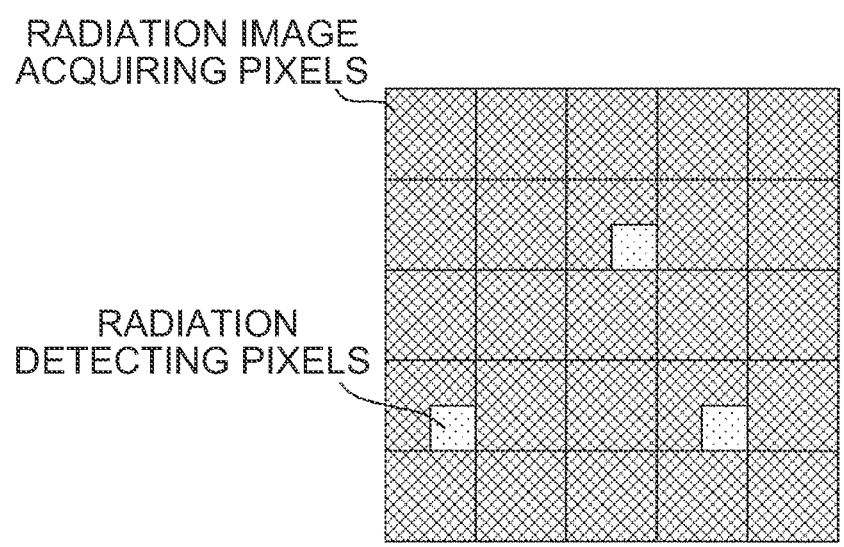

In this exemplary embodiments described above, as illustrated in FIG. 37A, the case where a part of the radiation image acquiring pixels 1032B is applied as the radiation detecting pixels 1032A is described. However, the invention is not limited thereto. For example, as illustrated in FIG. 37B, the radiation detecting pixels 1032A may be provided in the gaps of the radiation image acquiring pixels 1032B. In this case, since an area of the radiation image acquiring pixels 1032B corresponding to the provision positions of the radiation detecting pixels 1032A decreases, sensitivity of the pixels decreases. However, since the pixels can be used for detecting the radiation image, a quality of the radiation image can be improved. In order to detect the irradiation of the radiation, as disclosed in Japanese Patent Application Laid-Open No. 2010-264181, the bias current may be monitored and the irradiation of the radiation may be detected from the change of the bias current. An amplification current that is supplied to an amplification circuit incorporated in the first signal processing unit 1054 and amplifying an electric signal flowing through each data line 1036 may be monitored and the radiation irradiation may be detected from the change of the amplification current. Since a leakage current leaking from each pixel 1032 by the radiation irradiation also changes, the radiation irradiation may be detected from the change of the amplification current, by monitoring the leakage current leaking from each pixel 1032. All of the pixels 1032 that are two-dimensionally provided may be used as the radiation image acquiring pixels 1032B, radiation detection elements may be disposed between the pixels 1032, and the radiation irradiation may be detected from the detection result from the radiation detection elements. In the exemplary embodiment, the operation is described on the basis of FIG. 35. However, an operation order or contents may be appropriately modified as long as the same functions can be achieved. The disclosure of Japanese Patent Application Laid-Open No. 2010-264181 is incorporated herein by reference.

In the exemplary embodiments, the case where a part of the pixels 1032 provided in the radiation detector 1020 is used as the radiation detecting pixels 1032A is described. However, the invention is not limited thereto. For example, the radiation detecting pixels 1032A may be laminated in the radiation detector 1020 on a layer different from a layer of the pixels 1032 to form the radiation detection units. In this case, since the defective pixels are not generated, a quality of the radiation image can be improved as compared with the exemplary embodiment. The radiation detecting pixels 1032A or the radiation detection units may be configured to individually read the charge.

In the exemplary embodiments, the case where the charge is read from the radiation detector 1020 when the irradiation period shown by the exposure conditions passes from a point in time when the start of irradiation of radiation is detected is described. However, the invention is not limited. For example, after the start of irradiation of radiation is detected, the value of the digital data of the direct read line 1038 that becomes equal to or more than the threshold value for radiation irradiation detection may be continuously compared with the threshold value for the radiation irradiation detection, the radiation irradiation may end when the value of the digital data of the direct read line 1038 becomes less than the threshold value for radiation irradiation detection, and the charge may be read from the radiation detector 1020. For example, the console 1110 may transmit the exposure conditions and the radiation dose where the optimal density is obtained to the electronic cassette 40, and the electronic cassette 1040 may cumulatively store the value of the digital data of each direct read line 1038 which is input from the second signal processing unit 1055 after the start of irradiation of radiation is detected, notify the console 1110 of the end of the radiation irradiation, in a case in which a cumulative value of the radiation dose becomes a value of the radiation dose where the optimal density is obtained, and read the charge from the radiation detector 1020. In a case in which the end of the radiation irradiation is notified from the electronic cassette 1040, the console 1110 may control to stop the radiation irradiation from the radiation generating device 1120.

In the exemplary embodiments, a discharge of the charge that is accumulated in the radiation detecting pixel 1032A is not mentioned to avoid confusion. However, after discharging the charge accumulated in the radiation detecting pixel 1032A at a timing when the start of the radiation irradiation is detected, the end of the radiation irradiation may be detected. Thereby, the radiation dose can be prevented from being saturated when the end of the radiation irradiation is detected.

In the exemplary embodiments, the case where the sensor unit 1013 includes the organic photoelectric conversion material that receives light generated by the scintillator 1008 and generates the charge is described. However, the invention is not limited thereto. For example, the sensor unit 1013 that does not include the organic photoelectric conversion material may be applied.

In the exemplary embodiments, the case where the case 1042 to accommodate the cassette control unit 1058 and/or the power supply unit 1070 and the radiation detector 1020 are disposed in the casing 1041 of the electronic cassette 1040 not to overlap each other is described. However, the invention is not limited thereto. For example, the radiation detector 1020 and the cassette control unit 1058 and/or the power supply unit 1070 may be disposed to overlap each other.

In the exemplary embodiments, the case where the wireless communication is performed between the electronic cassette 1040 and the console 1110 and between the radiation generating device 1120 and the console 1110 is described. However, the invention is not limited thereto. For example, wired communication may be performed between at least one of the electronic cassette 1040 and the console 1110 and the radiation generating device 1120 and the console 1110.

In the exemplary embodiments, the case where the vibration is detected by the vibration detection unit 1061 is described. However, the invention is not limited thereto. For example, the vibration may be detected using the radiation detector 1020. Since the charge is generated or the amount of current flowing is changed by the vibration, the radiation detector 1020 can detect the vibration by monitoring a signal from the radiation detector 1020 and/or the amount of current flowing. For example, in the sensor unit 1013, the bias voltage is applied between the upper electrode 1006 and the lower electrode 1002, but the bias voltage is changed by the vibration. A voltage detection unit that detects the bias voltage may be provided and the vibration may be detected from the change of the bias voltage detected by the voltage detection unit. The amount of charge that is accumulated in the sensor unit 1013 by the dark current is changed by the vibration. The vibration may be detected from the change of the amount of charge read from each radiation image acquiring pixel 1032B by the reset operation. Similar to the detection of the radiation irradiation, the vibration may be detected from the change of the charge of the radiation detecting pixel 1032A or the change of the amplification current with respect to the amplification circuit incorporated in the first signal processing unit 1054. In a case in which the radiation detecting pixels 1032A or the radiation detection units to detect the radiation are configured to individually read the charge, all of the radiation detecting pixels 1032A or the radiation detection units do not need to be turned on to detect the completion of the positioning. When the vibration is detected, a part of the radiation detecting pixels 1032A or the radiation detection units may be turned on. After the completion of the positioning is determined, all of the radiation detecting pixels 1032A or the radiation detection units may be turned on to transit to a detection state of the radiation irradiation state. In a case in which the radiation irradiation is detected, all of the radiation detecting pixels 1032A or the radiation detection units do not need to be turned on and only a part of the radiation detecting pixels 1032A or the radiation detection units according to the image capturing part may be turned on.

In the exemplary embodiments, the case where an ON signal is output from the gate line driver 1052 to each gate line 1034, a radiation image is read, and the radiation detection is stopped at a timing when the image capturing ends is described. However, the invention is not limited thereto. For example, in a case in which the vibration is detected again by the vibration detection unit 1061 and it is determined that the image capturing is prepared, the radiation detection may be stopped.

The detection of the vibration using the radiation detector 1020 and the detection of the vibration using the vibration detection unit 1061 such as the acceleration sensor may be performed concurrently. As a result, even if the vibration is generated after the completion of the positioning is determined, the charge is generated in the radiation detecting pixel 1032A by the vibration, the electric signal flows to the direct read line 1038, and the radiation irradiation is erroneously detected, an erroneous detection can be prevented by concurrently using the detection of the vibration using the vibration detection unit 1061.

In the exemplary embodiments, the case where sampling of each direct read line 1038 by the second signal processing unit 1055 starts if the vibration is settled is described. However, the invention is not limited thereto. For example, when the electronic cassette 1040 is not used, the electronic cassette 1040 charges an incorporated battery in a state where the electronic cassette is accommodated in the accommodation unit 1130A of the cradle 1130. When a radiation image is captured, the electronic cassette 1040 is extracted from the cradle 1130 by the radiological technologist. Therefore, sampling of each direct read line 1038 may start at an extraction timing of the electronic cassette 1040 from the cradle 1130. When it is detected whether the electronic cassette 1040 is extracted from the cradle 1130, for example, a sensor may be provided in the electronic cassette 1040 and it may be detected whether the electronic cassette 1040 is accommodated in the accommodation unit 1130A. In a case in which the electronic cassette 1040 is accommodated in the accommodation unit 1130A and charging is performed by a terminal contact, the extraction of the electronic cassette 1040 from the cradle 1130 may be detected according to whether the terminal contacts. In a case in which the electronic cassette 1040 is accommodated in the accommodation unit 1030A and charging is performed through wireless feeding, the extraction of the electronic cassette 1040 from the cradle 1130 may be detected according to whether feeding is made.

In the exemplary embodiments, the case where the X-rays are applied as the radiation is described. However, the invention is not limited thereto. For example, other radiation such as gamma rays may be adopted.

The configuration (refer to FIG. 27) of the RIS 100, the configuration (refer to FIG. 28) of the radiation image capturing room, the configuration (refer to FIGS. 29 to 33) of the electronic cassette 1040, and the configuration (refer to FIG. 34) of the image capturing system 1104 that are described in the exemplary embodiments are exemplary, and unnecessary parts may be removed, new parts may be added, or a connection state and the like may be changed in a range that does not depart from the scope of the invention.

The configuration of the initial information that is described in the exemplary embodiments is also exemplary, and unnecessary information may be deleted or new information may be added in a range that does not depart from the scope of the invention.

The flow (refer to FIG. 35) of the processing of the image capturing control processing program that is described in the exemplary embodiments is also exemplary, and unnecessary steps may be removed, new steps may be added, or a processing sequence may be changed in a range that does not depart from the scope of the invention.

According to a first aspect, there is provided a radiation image capturing device which includes: an image capturing unit that captures a radiation image using irradiated radiation; a radiation detection unit that detects the radiation; a determination unit that determines whether image capturing preparation is completed; and a control unit that starts detection of the radiation by the radiation detection unit, in a case in which the determination unit determines that the image capturing preparation is completed, and controls the image capturing unit to capture a radiation image, in a case in which the radiation detection unit detects the radiation.

As such, according to the radiation image capturing device of the first aspect, it is determined whether the image capturing preparation is completed. In a case in which it is determined that the image capturing preparation is completed, detection of the radiation starts, and, in a case in which the radiation is detected by the radiation detection unit, a radiation image is captured. Therefore, radiographer's trouble can be saved, power consumption can be suppressed, and a radiation image can be captured using irradiated radiation without synchronizing an irradiation timing of the radiation with the radiation generating device to irradiate the radiation.

According to a second aspect, in the first aspect, the radiation image capturing device may further include a vibration detection unit that detects vibration, and the determination unit may determine that the image capturing preparation is completed, in a case in which the vibration detected by the vibration detection unit has settled to a predetermined state in which it is determined that positioning has ended.

According to a third aspect, in the second aspect, the vibration detection unit may be an acceleration sensor, a gyro sensor, a strain gauge, a gravity sensor, or a geomagnetism sensor.

According to a fourth aspect, in the second aspect, the image capturing unit may include a radiation detector which include plural sensor units in which a bias voltage is applied and the charge is generated by the radiation or light obtained by converting the radiation, and the vibration detection unit may detect the vibration on the basis of at least one of the change in the bias voltage and a change in an amount of dark current accumulated in the sensor units.

According to a fifth aspect, in the second aspect, the vibration detection unit may be a gravity sensor or a geomagnetism sensor and detect the vibration on the basis of a change in a gravity direction detected by the gravity sensor or a geomagnetic direction detected by the geomagnetism sensor.

According to a sixth aspect, in any one of the fifteenth to nineteenth aspects, the control unit may stop detection of the radiation by the radiation detector, after capturing of the radiation image by the image capturing unit ends or in a case in which the determination unit determines that image capturing preparation is completed.

According to a seventh aspect, the device according to the first aspect may further include: an image capturing panel including a plurality of pixels that convert radiation, which is emitted from a radiation source and is transmitted through the subject, into electric signals and accumulate the electric signals, and that are arranged in a matrix; and a movement amount measurement unit that measures a movement amount of the image capturing panel; and the determination unit may determine that the image capturing preparation is completed according to the movement amount measured by the movement amount measurement unit, and the control unit may further include a read control unit that starts a read mode which reads the electric signals accumulated in the pixels, according to the movement amount measured by the movement amount measurement unit, ends reading of the electric signals in a case in which values of the electric signals read in the read mode become more than a threshold value which is arbitrarily set, and transits the image capturing panel to an exposure state.

According to an eighth aspect, in the seventh aspect, the radiation image capturing device may further include a movement state identification unit that identifies a movement state of the image capturing panel, on the basis of the movement amount measured by the movement amount measurement unit, and the read control unit may start the read mode according to the movement state identified by the movement state identification unit.

According to a ninth aspect, in the eighth aspect, the movement state identification unit may identify the movement state as a static state in a case in which the movement amount is less than a first threshold value and identify the movement state as a moving state in a case in which the movement amount is more than a second threshold value (a value that is not less than the first threshold value), and the read control unit may start the read mode in a case in which the movement state of the image capturing panel transits from the moving state to the static state.

According to a tenth aspect, in the eighth aspect, the read control unit may start the read mode in a case in which the movement state of the image capturing panel transits from the moving state to the static state and the moving state has been maintained for longer than first predetermined time going back from a point in time of the transition.

According to a eleventh aspect, in the eighth aspect, the read control unit may end the read mode in a case in which the movement state of the image capturing panel is the static state and the static state has been maintained for longer than a second predetermined time going back from a current point in time.

According to a twelfth aspect, in the seventh aspect, the radiation image capturing device may further include a start/end notification unit that notifies that the read mode has started and/or ended.

According to a thirteenth aspect, in the seventh aspect, the movement amount measurement unit may include an acceleration sensor.

According to a fourteenth aspect, in the seventh aspect, the movement amount measurement unit may include a gyroscope.

According to a fifteenth aspect, in the seventh aspect, the movement amount measurement unit may include a camera.

According to the seventh to fifteenth aspects, it is determined whether irradiation of the radiation starts on the basis of the electric signal read from the pixels by execution of the read mode. When it is determined that the irradiation of the radiation starts, the reading of the charge ends and an operation state transits to an accumulation state. Therefore, an image capturing timing does not need to be synchronized and a cost decreases. Since the read mode is executed until it is determined that the irradiation of the radiation starts, unnecessary charge accumulated in the pixels can be removed, and noise of a radiation image can be decreased. Since the movement amount of the image capturing panel is measured, it can be predicted whether an image can be captured at a current point in time, using the movement amount of the electronic cassette. That is, a consumption power can be decreased by starting the read mode at an appropriate timing immediately before the image capturing.

According to a sixteenth aspect, there is provided a radiation image capturing method which includes: determining whether image capturing preparation is completed; starting detection of radiation by a radiation detector which detects the radiation, in a case in which it is determined that the image capturing preparation is completed; and controlling an image capturing unit to capture a radiation image, in a case in which the radiation is detected by the radiation detector.

Radiographer's trouble can be saved, power consumption can be suppressed, and a radiation image can be captured using irradiated radiation without synchronizing an irradiation timing of the radiation with the radiation generating device to irradiate the radiation.

According to an aspect, there is provided a radiation image capturing device which includes: an image capturing panel including a plurality of pixels that convert radiation, which is emitted from a radiation source and is transmitted through a subject, into electric signals and accumulate the electric signals, and that are arranged in a matrix; a movement amount measurement unit that measures a movement amount of the image capturing panel; and a read control unit that starts a read mode which reads the electric signals accumulated in the pixels, according to the movement amount measured by the movement amount measurement unit, ends reading of the electric signals in a case in which values of the electric signals read in the read mode become more than a threshold value which is arbitrarily set, and transits the image capturing panel to an exposure state.

The radiation image capturing device may further include a movement state identification unit that identifies a movement state of the image capturing panel, on the basis of the movement amount measured by the movement amount measurement unit, and the read control unit may start the read mode according to the movement state identified by the movement state identification unit.

The movement state identification unit may identify the movement state as a static state in a case in which the movement amount is less than a first threshold value and identify the movement state as a moving state in a case in which the movement amount is more than a second threshold value (a value that is not less than the first threshold value), and the read control unit may start the read mode in a case in which the movement state of the image capturing panel transits from the moving state to the static state.

The read control unit may start the read mode in a case in which the movement state of the image capturing panel transits from the moving state to the static state and the moving state has been maintained for longer than first predetermined time going back from a point in time of the transition.

The read control unit may end the read mode in a case in which the movement state of the image capturing panel is the static state and the static state has been maintained for longer than a second predetermined time going back from a current point in time.

The radiation image capturing device may further include a start/end notification unit that notifies that the read mode has started and/or ended.

The movement amount measurement unit may include an acceleration sensor.

The movement amount measurement unit may include a gyroscope.

The movement amount measurement unit may include a camera.

In the read mode, the electric signals that are accumulated in the pixels may be read by the number of times of reading that is less than the total number of rows of the image capturing panel.

In the read mode, the electric signals that are accumulated in the plural pixels may be simultaneously read in a unit of plural rows.

In the read mode, the electric signals that are accumulated in the pixels of a predetermined row may be read.

A radiation image capturing system may include the radiation image capturing device of the above mentioned aspects, and the radiation source that irradiates the radiation.

According to another aspect, there is provided a radiation image capturing method of capturing a radiation image using an image capturing panel which include a plurality of pixels that convert radiation emitted from a radiation source and transmitted through a subject into electric signals and accumulate the electric signals, and that are arranged in a matrix, the radiation image capturing method which includes: measuring a movement amount of the image capturing panel; starting a read mode which reads the electric signals accumulated in the pixels, according to the measured movement amount; and ending reading of the electric signals in a case in which values of the electric signals read in the read mode become more than a threshold value which is arbitrarily set, and transiting the image capturing panel to an exposure state.

It is determined whether irradiation of the radiation starts on the basis of the electric signal read from the pixels by execution of the read mode. When it is determined that the irradiation of the radiation starts, the reading of the charge ends and an operation state transits to an accumulation state. Therefore, an image capturing timing does not need to be synchronized and a cost decreases. Since the read mode is executed until it is determined that the irradiation of the radiation starts, unnecessary charge accumulated in the pixels can be removed, and noise of a radiation image can be decreased. Since the movement amount of the image capturing panel is measured, it can be predicted whether an image can be captured at a current point in time, using the movement amount of the electronic cassette. That is, a consumption power can be decreased by starting the read mode at an appropriate timing immediately before the image capturing.

According to another aspect, there is provided a non-transitory computer readable medium storing a radiation image capturing control program causing a computer to execute a processing, the processing which includes: determining whether image capturing preparation is completed; starting detection of radiation by a radiation detector which detects the radiation, in a case in which it is determined that the image capturing preparation is completed; and controlling an image capturing unit to capture a radiation image, in a case in which the radiation is detected by the radiation detector.

Radiographer's trouble can be saved, power consumption can be suppressed, and a radiation image can be captured using irradiated radiation without synchronizing an irradiation timing of the radiation with the radiation generating device to irradiate the radiation.

Embodiments of the invention are described above, but the invention is not limited to the embodiments as will be clear to those skilled in the art.

What is claimed is:

1. A radiation image capturing device comprising:
   an image capturing unit that captures a radiation image using irradiated radiation;
   a radiation detection unit that detects the radiation;
   a determination unit that determines whether image capturing preparation is completed;
   a control unit that starts detection of the radiation by the radiation detection unit, in a case in which the determination unit determines that the image capturing preparation is completed, and controls the image capturing unit to capture a radiation image, in a case in which the radiation detection unit detects the radiation;
   an image capturing panel comprising a plurality of pixels that convert radiation, which is emitted from a radiation source and is transmitted through the subject, into electric signals and accumulate the electric signals, and that are arranged in a matrix; and
   a movement amount measurement unit that measures a movement amount of the image capturing panel;
   wherein the determination unit determines that the image capturing preparation is completed according to the movement amount measured by the movement amount measurement unit, and
   wherein the control unit further comprises a read control unit that starts a read mode which reads the electric signals accumulated in the pixels, according to the movement amount measured by the movement amount measurement unit, ends reading of the electric signals in a case in which values of the electric signals read in the read mode become more than a threshold value which is arbitrarily set, and transitions the image capturing panel to an exposure state.

2. The radiation image capturing device of claim 1, further comprising:
   a movement state identification unit that identifies a movement state of the image capturing panel, on the basis of the movement amount measured by the movement amount measurement unit,
   wherein the read control unit starts the read mode according to the movement state identified by the movement state identification unit.

3. The radiation image capturing device of claim 2, wherein
   the movement state identification unit identifies the movement state as a static state in a case in which the movement amount is less than a first threshold value and identifies the movement state as a moving state in a case in which the movement amount is more than a second threshold value, the second threshold value being a value that is not less than the first threshold value, and
   the read control unit starts the read mode in a case in which the movement state of the image capturing panel transitions from the moving state to the static state.

4. The radiation image capturing device of claim 2, wherein
   the read control unit starts the read mode in a case in which the movement state of the image capturing panel transitions from a moving state to a static state and the moving state has been maintained for longer than a first predetermined time period going back from a point in time of the transition.

5. The radiation image capturing device of claim 2, wherein
   the read control unit ends the read mode in a case in which the movement state of the image capturing panel is a static state and the static state has been maintained for longer than a second predetermined time period going back from a current point in time.

6. The radiation image capturing device of claim 1, further comprising:
   a start/end notification unit that notifies that the read mode has started, ended, or a combination thereof.

7. The radiation image capturing device of claim 1, wherein
   the movement amount measurement unit comprises an acceleration sensor.

8. The radiation image capturing device of claim 1, wherein
   the movement amount measurement unit comprises a gyroscope.

9. The radiation image capturing device of claim 1, wherein
   the movement amount measurement unit comprises a camera.

10. A radiation image capturing method comprising:
   determining whether image capturing preparation is completed;
   starting detection of radiation by a radiation detector which detects the radiation, in a case in which it is determined that the image capturing preparation is completed; and
   controlling an image capturing unit to capture a radiation image, in a case in which the radiation is detected by the radiation detector,
   wherein determining whether image capturing preparation is completed further comprises determining that the image capturing preparation is completed according to a movement amount of an image capturing panel which comprises a plurality of pixels that convert radiation, which is emitted from a radiation source and is transmitted through a subject, into electric signals and accumulate the electric signals, and that are arranged in a matrix,
   starting detection of radiation by a radiation detector which detects the radiation in a case in which it is determined that the image capturing preparation is completed further comprises starting a read mode which reads the electric signals accumulated in the pixels, according to the measured movement amount, and
   controlling an image capturing unit to capture a radiation image in a case in which the radiation is detected by the radiation detector further comprises ending reading of the electric signals in a case in which values of the electric signals read in the read mode become more than a threshold value which is arbitrarily set, and transitions the image capturing panel to an exposure state.

* * * * *